United States Patent [19]
Bujard et al.

[11] Patent Number: 6,136,954
[45] Date of Patent: Oct. 24, 2000

[54] TETRACYCLINE-INDUCIBLE TRANSCRIPTIONAL ACTIVATOR FUSION PROTEINS

[75] Inventors: Hermann Bujard, Heidelberg, Germany; Manfred Gossen, El Cerrito, Calif.

[73] Assignees: BASF Aktiengesellschaft, Worcester, Mass.; Knoll Aktiengesellschaft, Germany

[21] Appl. No.: 09/162,184

[22] Filed: Sep. 28, 1998

Related U.S. Application Data

[63] Continuation of application No. 08/485,978, Jun. 7, 1995, Pat. No. 5,814,618, which is a continuation-in-part of application No. 08/383,754, Feb. 3, 1995, Pat. No. 5,789,156, which is a continuation-in-part of application No. 08/275,876, Jul. 15, 1994, Pat. No. 5,654,168, which is a continuation-in-part of application No. 08/270,637, Jul. 1, 1994, abandoned, and a continuation-in-part of application No. 08/260,452, Jun. 14, 1994, Pat. No. 5,650,298, which is a continuation-in-part of application No. 08/076,327, Jun. 14, 1993, abandoned, and a continuation-in-part of application No. 08/076,726, Jun. 14, 1993, Pat. No. 5,464,758.

[51] Int. Cl.$^7$ ............................ C07K 14/00; C12N 15/11
[52] U.S. Cl. ........................................... 530/350; 536/23.4
[58] Field of Search ............................ 530/350; 536/23.4

[56] References Cited

U.S. PATENT DOCUMENTS

| | | | |
|---|---|---|---|
| 4,833,080 | 5/1989 | Brent et al. ............................ | 435/69.7 |
| 5,221,778 | 6/1993 | Byrne et al. ............................. | 800/21 |

FOREIGN PATENT DOCUMENTS

| | | |
|---|---|---|
| 0 332 416 | 9/1989 | European Pat. Off. . |
| 0 455 424 A3 | 11/1991 | European Pat. Off. . |
| 0 455 687 B1 | 11/1991 | European Pat. Off. . |
| 0 494 724 A2 | 7/1992 | European Pat. Off. . |
| WO 91/19784 | 12/1991 | WIPO . |
| WO 91/19796 | 12/1991 | WIPO . |
| WO 92/11874 | 7/1992 | WIPO . |
| WO 92/20808 | 11/1992 | WIPO . |
| WO 93/04169 | 3/1993 | WIPO . |
| WO 93/23431 | 11/1993 | WIPO . |
| WO 94/04672 | 3/1994 | WIPO . |
| WO 94/18317 | 8/1994 | WIPO . |

OTHER PUBLICATIONS

Gossen et al. Tight control of gene expression in mammalian cells by tetracycline–responsive promoters. Proc. Nat. Acad. Sci. USA vol. 89 pp. 5547–5551, 1992.

Ackland–Berglund, C.E. and Lieb, D.A. (1995) "Efficacy of Tetracycline–Controlled Gene Expression Is Influenced by Cell Type" *Bio Techniques* 18(2):196–200.

Agarwal, M.L. et al., "p53 Controls Both the $G_2$/M and the $G_1$ Cell Cycle Checkpoints and Mediates Reversible Growth Arrest in Human fibroblasts," *Proc. Natl. Acad. Sci. USA*, 92: pp. 8493–8497 (1995).

Altschmied, L. et al., (1988) "A threonine to alanine exchange at position 40 of Tet repressor alters the recognition of the sixth base pair of tet operator from GC to AT", *The EMBO Journal*, 7(12):4011–4017.

Baim, S.B., et al., (1991) "A chimeric mammalian transactivator based on the lac repressor that is regulated by temperature and isopropyl β–D–thiogalactopyranoside", *Proceedings of the National Academy of Science* 88: 5072–5076.

Baniahmad, A. et al. (1992) "A Transferable Silencing Domain Is Present In the Thyroid Hormone Receptor, In the v–erbA Oncogene Product and In the Retinoic Acid Receptor" *The EMBO Journal* 11(3):1015–1023.

Bergman, M. et al. "Overexpressed Csk Tyrosine Kinase Is Localized in Focal Adhesions, Causes Reorganization of $α_v β_5$ Integrin, and Interferes with HeLa Cell Spreading", *Molecular and Cellular Biology*, 15, No. 2, pp. 711–722 (1995).

Boshart, M., et al., (1985) "A Very Strong Enhancer Is Located Upstream of an Immediate Early Gene of Human Cytomegalovirus", *Cell* 41(2):521–530.

Bradley, A., (1991) "Modifying the mammalian genome by gene targeting", *Current Opinion in Biotechnology* 2: 832–829.

Brent, R. and M. Ptashne (1984) "A Bacterial Repressor Protein or a Yeast Transcriptional Terinator Can Block Upstream Activation of A Yeast Gene" *Nature* 312:612–615.

Brent R. and M. Ptashne (1985) "A Eukaryotic Transcriptional Activator Bearing the DNA Specificity of a Prokaryotic Repressor" *Cell* 43:729–736.

Brown, M., et al., (1987) "lac Repressor Can Regulate Expression from a Hybrid SV40 Early Promoter Containing a lac Operator in Animal Cells", *Cell.* 49:603–612.

(List continued on next page.)

*Primary Examiner*—John S. Brusca
*Attorney, Agent, or Firm*—Giulio A. DeConti, Jr.; Elizabeth A. Hanley; Lahive & Cockfield, LLP

[57] ABSTRACT

Methods of regulating gene expression in subjects using tetracycline-responsive fusion proteins are disclosed. In one embodiment, the method involves introducing into a cell the subject a nucleic acid molecule encoding a fusion protein which inhibits transcription, the fusion protein comprising a first polypeptide which binds to a tet operator sequence, operatively linked to a heterologous second polypeptide which inhibits transcription in eukaryotic cells; and modulating the concentration of a tetracycline, or analogue thereof, in the subject. The first polypeptide can binds to a tet operator sequence in the absence, but not the presence, of tetracycline. Alternatively, the first polypeptide can binds to a tet operator sequence in the presence, but not the absence, of tetracycline. In another embodiment, the method of the invention involves obtaining a cell from a subject, introducing into the cell a first nucleic acid molecule which operatively links a gene to at least one tet operator sequence, introducing into the cell a second nucleic acid molecule encoding an inhibitory fusion protein of the invention to form a modified cell, administering the modified cell to the subject and modulating the concentration of a tetracycline, or analogue thereof, in the subject. The first and second nucleic acid molecules can be linked or can be separate molecules.

11 Claims, 15 Drawing Sheets

OTHER PUBLICATIONS

Buckbinder L. et al. (1994) "Gene Regulation by Temperature-Sensitive p53 Mutants: Identification of p53 response genes" *Proc. Natl. Acad. Sci. USA* 91:10640–10644.

Capecchi, M.R., (1989) "Altering the Genome by Homologous Recombination", *Science* 244:1288–1292.

Cayrol, C. et al. "Identification of Cellular Target Genes of the Epstein–Barr Virus Transactivator Zta: Activation of Transforming Growth Factor βigh3 (TGF–βigh3) and TGF–β1", *Journal of Virology*, 69, No. 7, pp. 4206–4212, (1995).

Chen, Y.Q. et al. "Tumor Suppression by p21$^{WAF11}$", *Cancer Research*, 55, pp. 4536–4539, (1995).

Courey, A.J., and Tjian, R., (1988) "Analysis of Sp1 In Vivo Reveals Multiple Transcriptional Domains, Including a Novel Glutamine–Rich Activation Motif", *Cell* 55:887–898.

Cowell, "Repression versus activation in the control of gene transcription," *Trends in Biochemical Sciences*, 19:1, 38–42 (1994).

Degenkolb, J. et al. "Structural Requirements of Tetracycline–Tet Repressor Interaction: Determination of Equilibrium Binding Constants for Tetracycline Analogs with the Tet Repressor" *Antimicrobial Agents and Chemotherapy* 35(8):1591–1595 (1991).

Deuschle, U., et al., (1989) "Regulated expression of foreign genes in mammalian cells under the control of coliphage T3 RNA polymerase and lac repressor", *Proceedings of the National Academy of Science* 86:5400–5404.

Deuschle et al., "Tetracycline–reversible silencing of eukaryotic promoters," *Mol. Cell. Biol.*, 15:4, 1907–1914 (1995).

Dhawan, J. et al. "Tetracycline–Regulated Gene Expression Following Direct Gene Transfer into Mouse Skeletal Muscle", *Somatic Cell and Molecular Genetics*, 21, No. 4, pp. 233–240, (1995).

Efrat, S. et al. "Conditional Transformation of a Pancreatic β–Cell Line Derived From Transgenic Mice Expressing A Tetracycline–Regulated Oncogene" *Proc. Natl. Acad. Sci. USA*, 92, pp. 3576–3580 (1995).

Epstein–Baak, R., et al., (1992) "Inducible Transformation of Cells from Transgenic Mice Expressing SV40 under Lac Operon Control", *Cell Growth & Differentiation* 3:127–134.

Fieck, A., et al., (1992) "Modifications of the *E. Coli* Lac Repressor for Expression in Eukaryoitic Cells: Effect of Nuclear Signal Sequence on Protein Activity and Nuclear Documentation", *Nucleic Acid Research* 20:1785–1791.

Figge, J., et al., (1988) "Stringent Regulation of Stably Integrated Chloramphenicol Acetyl Transferase Genes by *E. coli* lac Repressor in Monkey Cells", *Cell* 52:713–722.

Fishman G. et al. (1994) "Tetracycline–Regulated Cardiac Gene Expression in Vivo" *J. Clin. Invest.* 93:1864–1868.

Furth P. (1994) "Temporal Control of Gene Expression in Transgenic Mice By A Tetracycline–Responsive Promoter" *Proc. Natl. Acad. Sci. USA* 91:9302–9306.

Gatz et al. "Stringent repression and homogeneous de–repression by tetracycline of a modified CaMV 35S promoter in intact transgenic tobacco plants," *The Plant Journal*, 2:3, 397–404 (1992).

Gatz, C. et al. "Regulation of a modified CaMV 35S Promoter by the Tn 10–encoder Tet Receptro in Transgenic Tobacco" *Mol. Gen. Genet.* 227(2):229–237 (1991).

Gatz, C. and P. Quail "Tn10–Encoded tet Repressor Can Regulate and Operator–Containing Plant Promoter" *Proc. Natl. Acad. Sci. USA* 85:1394–1397 (1988).

Gjetting, T. et al. "Regulated Expression of the Retinoblastoma Susceptibility Gene in Mammary Carcinoma Cells Restores Cyclin D1 Expression and $G_1$–Phase Control", *Biol. Chem. Hoppe–Seyler*, 376, pp. 441–446 (1995).

Gossen M. and B. Hermann (1993) "Anhydrotetracycline, A Novel Effector of Tetracycline Controlled Gene Expression Systems In Eukaryotic Cells" *Nucleic Acids Research* 21(18):4411–4412.

Gossen, M., et al., (1993) "Control of gene activity in higher eukaryotic cells by prokaryotic regulatory elements", *TIBS* 18(12):471–475.

Gossen et al., "Exploiting prokaryotic elements for the control of gene activity in higher eukaryotics," Keystone Symposium on Gene Therapy and Molecular Medicine, Steamboat Springs, Colorado, *Journal of Cellular Biochemistry*, Supplement 0 (21A), Abstract No. C6–220, 355 (1995).

Gossen et al. (1994) "Inducible Gene Expression Systems For Higher Eukaryotic Cells" *Current Opinion in Biotechnology* 5:516–520.

Gossen, M., and Bujard, H., (1992) "Tight control of gene expression in mammalian cells by tetracycline–responsive promoters", *Proceedings of the National Academy of Science* 89:5547–5551.

Gossen et al., "Transcriptional activation by tetracyclines in mammalian cells," *Science*, 268:5218, 1766–1769 (1995).

Haase, S.B. et al. "Transcription Inhibits the Replication of Autonomously Replicating Plasmids in Human Cells", *Molecular and Cellular Biology*, 14, No. 4, pp. 2516–2524 (1994).

Hecht, B., et al., (1993) "Noninducible Tet Repressor Mutations Map from the Operator Motif to the C Terminus", *Journal of Bacteriology* 175(4).

Hennighausen, L. et al. "Conditional Gene Expression in Secretory Tissues and Skin of Transgenic Mice Using the MMTV–LTR and the Tetracycline Responsive System", *Journal of Cellular Biochemistry*, 59, pp. 463–472, (1995).

Herschbach B. and A. Johnson (1993) "Transcriptional Repression In Eukaryotes" *Annu. Rev. Cell Biol.* 9:479–509.

Hillen, W., and Schollmeier, K., (1983) "Nucleotide sequence of the Tn10 encoded tetracycline resistance gene", *Nucleic Acid Research* 11(2):525–539.

Hinrichs, W., et al., (1994) "Structure of the Tet Repressor–Tetracycline Complex and Regulation of Antibiotic Resistance", *Science* 264:418–420.

Howe, J.R. et al. "The Responsiveness of a Tetracycline-–Sensitive Expression System Differs in Different Cell Lines", *The Journal of Biological Chemistry*, 270, No. 23, pp. 14168–14174, (1995).

Hu, M.C–T and Davidson, N., (1987) "The Inducible lac Operator–Repressor System Is Functional in Mammalian Cells", *Cell* 46:555–566.

Labow, M.A., et al., (1990) "Conversion of the lac Repressor into an Allosterically Regulated Transcriptional Activator for Mammalian Cells", *Molecular and Cellular Biology* 10(7):3343–3356.

Liang et al., "Enhanced and switchable expression systems for gene–transfer," Keystone Symposium on Gene Therapy and Molecular Medicine, Steamboat Springs, Colorado, *Journal of Cellular Biochemistry*, Supplement 0 (21A), Abstract No. C6–220, 379 (1995).

Licht, J. et al. (1990) "Drosophila Krüppel Protein is a Transcriptional Repressor" *Nature* 346:76–79.

Mansour, S.L. et al. "Disruption of the Proto–Oncogene int–2 in Mouse Enbryo–Derived Stem Cells: a General Strategy for Targeting Mutations to Non–Selectable Genes" *Nature* 336:348–352 (1988).

Mermod N. et al. "The Proline–Rich Transcriptional Activator of CT/NF–I Is Distinct fom the Replication and DNA Binding Domain" *Cell* 58:741–753 (1989).

Miller, K. et al. "The Function of Inducible Promoter Systems in F9 Embryonal Carcinoma Cells", *Experimental Cell Research*, 218, pp. 144–150, (1995).

Passman, R.S. et al., "Regulated Expression of Foreign Genes In Vivo After Germline Transfer", *J. Clin. Invest.*, 94, pp. 2421–2425 (1994).

Pescini R. et al. (1994) "Inducible Inhibition of Eukaryotic Gene Expression" *Biochemical and Biophysical Research Communications* 202(3):1664–1667.

Postle, K., et al., (1984) "Nucleotide sequence of the repressor gene of the TN10 tetracycline resistance determinant", *Nucleic Acid Research* 12(12):4849–4863.

Renkawitz R. (1990) "Transcriptional Repression In Eukaryotes" *TIG* 6(6):192–193.

Resnitzky D. (1994) "Acceleration of the G1/S Phase Transition by Expression of Cyclins D1 and E with an Inducible System" *Molecular and Cellular Biology* 14(3):1669–1679.

Sauer, F. and H. Jäckle (1993) "Dimerization and the Control of Transcription by Krüppel" *Nature* 364:454–457.

Seipel, K., et al., (1992) "Different activation domains stimulate transcription from remote ('enhancer') and proximal ('promoter') positions", *The EMBO Journal* 11(13):4961–4968.

Smithies, O., et al., (1985) "Insertion of DNA sequences into the human chromosomal β–globin locus by homologous recombination", *Nature* 317:pp. 230–234.

Sopher, B.L. et al., "Cytotoxicity Mediated By Conditional Expression of a Carboxyl–Terminal Derivative of the β–Amyloid Precursor Protein", *Molecular Brain Research*, 26, pp. 207–217, (1994).

Tovar, K., et al., (1988) "Identification and nucleotide sequence of the class E tet regulatory elements and operator and inducer binding of the encoded purified Tet repressor", *Mol. Gen. Genet.* 215:76–80.

Triezenberg, S.J., et al., (1988) "Functional dissection of VP16, the trans–activator of herpes simplex virus immediate early gene expression", *Genes & Development* 2:718–729.

Unger, B., et al., (1984) "Nucleotide sequence of the gene, protein purification and characterization of the pSC101–encoded tetracycline resistance–gene–repressor", *Gene.* 31:103–108.

Unger, B., et al., (1984) "Nucleotide sequence of the repressor gene of the RA1 tetracycline resistance determinant: structural and functional comparison with three related Tet repressor genes", *Nucleic Acid Research* 12(20):7693–7703.

Waters, S.H, et al., (1983) "The tetracycline resistance determinants of RP1 and Tn1721: nucleotide sequence analysis", *Nucleic Acid Research* 11(17):6089–6105.

Weinmann P. et al. (1994) "A Chimeric Transactivator Allows Tetracycline–Responsive Gene Expression in Whole Plants", *The Plant Journal* 5(4):559–569.

Wimmel A. et al. (1994) "Inducible Acceleration of G1 Progression Through Tetracycline–Regulated Expression of Human Cyclin E" *Oncogene* 9:995–997.

Wissmann, A. et al. "Selection for Tn10 Tet Repressor Binding to tet Operator in *Escherichia coli*: Isolation of Temperature–Sensitive Mutants and and combinatorial Mutagenesis in the DNA Binding Motif" *Genetics* 128:225–232 (1991).

Wu, Z. et al. "Conditional Ectopic Expression of C/EBPβ in NIH–3T3 Cells Induces PPARγ and Stimulates Adipogenesis", *Genes & Development*, 9, pp. 2350–2363, (1995).

Wyborski, D.L., and Short, J.M., (1991) "Analysis of Inducers of the *E. Coli* Lac Repressor System in Mammalian Cells and Whole Animals", *Nucleic Acid Research* 19:4647–4653.

Yarranton G. (1992) "Inducible Vectors For Expression In Mamalian Cells" *Current Opinion in Biotechnology* 3:506–511.

MSRLDKSKVINSALELLNEVGIEGLTTRKLAQKLGVEQPTLYWHVKNKRALLDALAIEMLDRH   63  B
MA--NRES--DA--G----T--DE-------------I-----------------V-I-A--       D
MTK-QPNT--RA--D------VD--------ER---Q--A----FR-----------EA--AEN     A
MNK-QREA--RT--G---D--M-------R-ER---Q--A----F------------EA--TIN     C
MTK---GT--AAG--------MDS-------ER-K-Q--A----FQ----------PEA--RER     G
MA--SLDD--SM--T--DSE-L---------S-KI---------R--QT-MNM-SEAI-AK-       E
```

```
              ┌──────┐    ┌────┐     ┌─────┐
              │  5   │    │ 6  │     │  7  │
         ─────┴──────┴────┴────┴─────┴─────┴───
●● ●  ●    ●  ●●  ●  ●●●●●●●●●●●●●  ● ●● ●● ●●

HTHFCPLEGESWQDFLRNNAKSFRCALLSHRDGAKVHLGTRPTEKQYETLENQLAFLCQQGFS  126  B
-DYSL-AA-----S------M---R---RY---------D----Q-V-T--R-MTEN---         D
---SV-RADDD-RS--IG--R---Q---AY----RI-A----GAP-M--ADA--R---EA---      A
---ST-RDDDD-RS--KG--C---R---AY----RI-A----AAP-M-KADA--R---DA---      C
--RSL-E-N-D-RV--KE--L---T----Y----RI-A------PNFG-A-T-IR---AE--C      G
--RSA--PT----Q--QE--L---K---V-----RL-I--S--PP-F-QA-A--RC--DA---      E
```

```
         ┌────────────┐             ┌─────┐
         │     8      │             │  9  │
      ───┴────────────┴─────────────┴─────┴───
           ● ●  ●● ●●●●●●  ●●   ●●      ● ●● ●●●

LENALYALSAVGHFTLGCVLEDQEHQVAKEERE     TPTTDSMPPLLRQAIELFDHQGA   182  B
-RDG---I---S-----A---Q---TA-LTD-P     AAPDENL-----E-LQIM-SDDG   182  D
AGD-VN--MTISY--V-A---E-AGDSESG--GG    -VEQAPLS----A--DA--EA-P   183  A
AGD-T---M-ISY--V-A---Q-ASEADA---GEDQL-TSAST--AR-QS-MKIVYEA-P    186  C
PKR-VW--R--S-YVV-S---Q-ASDAD   --VPDRPDVSEQAPSSF-HVLFHELETD-M   184  G
V-E--FI-QSIS-----A--E-ATNQIENNHV      I-AA----QE-FNIQARTS-      179  E
```

```
         ┌──────────┐
         │    10    │
      ───┴──────────┴───
              ●

EPAFLFGLELIICGLEKQLKCESGS             207  B
-Q---H---SL-R-F-V--TALLQIVGGDKLIIPFC   218  D
DA--EQ--AV-VD--A-RRLVVRNVEGPRKGDD      216  A
DA--ER--A---G----MRLTTNDIEVLKNVDE      219  C
DA--N---DSL-A-F-RLRAAVLATD             210  G
-M--H---KSL-F-FSA--DEKKHTPIEDGNK       211  E
```

5' <u>GAATTC</u>GGGG
  EcoRI    +75

CCGCGGAGGCTGGATCGGTCCCGGTGTCTTCTATGGAGGTCAAAACAGCGTGGA

+1
                    ←──────┐
                           C                                    P<sub>hCMV*</sub>-3
TGGCGTCTCCAGGCGATCTGACGGTTCACTAAACGAGCTCTGCTTATATAGG
                                                        -31

*tet O*
TC ( *GAGTTTACCACTCCCTATCAGTGATAGAGAAAAGTGAAAGTC* )<sub>7</sub>GAGC
     ──────────────────────→←─────────

P<sub>hCMV*</sub>-1
TCGGTACCCGGGTCGAGTAGGCGTGTACGGTGGGAGGCCTATATAAGCAGAG
           -53

CTCGTTTAGTGAACCGTCAGATCGCCTGGAGACGCCATCCACGCTGTTTTGA
                        └──→
                         +1

CCTCCATAGAAGACACCGGGACCGATCCAGCCTCCGCGGCCCC<u>GAATTC</u> 3'
                                        +75    EcoRI

TETRACYCLINE-INDUCIBLE TRANSCRIPTIONAL ACTIVATOR FUSION PROTEINS

RELATED APPLICATIONS

This application is a continuation of U.S. Ser. No. 08/485,978, filed Jun. 7, 1995, U.S. Pat. No. 5,814,618, which is a continuation-in-part of U.S. Ser. No. 08/383,754, filed Feb. 3, 1995, now U.S. Pat. No. 5,789,156, which is a continuation-in-part of U.S. Ser. No. 08/275,876, filed Jul. 15, 1994, now U.S. Pat. No. 5,654,168, which is a continuation-in-part of U.S. Ser. No. 08/270,637, filed Jul. 1, 1994, now abandoned. U.S. Ser. No. 08/485,978 is also a continuation-in-part of U.S. Ser. No. 08/260,452, filed Jun. 14, 1994, now U.S. Pat. No. 5,650,298, which is a continuation-in-part of U.S. Ser. No. 08/076,327, filed Jun. 14, 1993, now abandoned. U.S. Ser. No. 08/485,978 is also a continuation-in-part of Ser. No. 08/076,726, filed Jun. 14, 1993, now U.S. Pat. No. 5,464,758. The entire contents of each of these applications are incorporated herein by reference.

BACKGROUND OF THE INVENTION

Functional analysis of cellular proteins is greatly facilitated through changes in the expression level of the corresponding gene for subsequent analysis of the accompanying phenotype. For this approach, an inducible expression system controlled by an external stimulus is desirable. Ideally such a system would not only mediate an "on/off" status for gene expression but would also permit limited expression of a gene at a defined level.

Attempts to control gene activity have been made using various inducible eukaryotic promoters, such as those responsive to heavy metal ions (Mayo et al. (1982) *Cell* 29:99–108; Brinster et al. (1982) *Nature* 296:39–42; Searle et al. (1985) *Mol. Cell. Biol.* 5:1480–1489), heat shock (Nouer et al. (1991) in *Heat Shock Response*, e.d. Nouer, L., CRC, Boca Raton, Fla., pp167–220) or hormones (Lee et al. (1981) *Nature* 294:228–232; Hynes et al. (1981) *Proc. Natl. Acad. Sci. USA* 78:2038–2042; Klock et al. (1987) *Nature* 329:734–736; Israel & Kaufman (1989) *Nucl. Acids Res.* 17:2589–2604). However, these systems have generally suffered from one or both of the following problems: (1) the inducer (e,g, heavy metal ions, heat shock or steroid hormones) evokes pleiotropic effects, which can complicate analyses, and (2) many promoter systems exhibit high levels of basal activity in the non-induced state, which prevents shut-off the regulated gene and results in modest induction factors.

An approach to circumventing these limitations is to introduce regulatory elements from evolutionarily distant species such as *E. coli* into higher eukaryotic cells with the anticipation that effectors which modulate such regulatory circuits will be inert to eukaryotic cellular physiology and, consequently, will not elicit pleiotropic effects in eukaryotic cells. For example, the Lac repressor (lacR)/operator/inducer system of *E. coli* functions in eukaryotic cells and has been used to regulate gene expression by three different approaches: (1) prevention of transcription initiation by properly placed lac operators at promoter sites (Hu & Davidson (1987) *Cell* 48:555–566; Brown et al. (1987) *Cell* 49:603–612; Figge et al. (1988) *Cell* 52:713–722; Fuerst et al. (1989) *Proc. Natl. Acad. Sci. USA* 86:2549–2553: Deuschle et al. (1989) *Proc. Natl. Acad. Sci. USA* 86:5400–5405); (2) blockage of transcribing RNA polymerase II during elongation by a LacR/operator complex (Deuschle et al. (1990) *Science* 248:480–483); and (3) activation of a promoter responsive to a fusion between LacR and the activation domain of herpes simples virus (HSV) virion protein 16 (VP16) (Labow et al. (1990) *Mol. Cell. Biol.* 10:3343–3356; Baim et al. (1991) *Proc. Natl. Acad. Sci. USA* 88:5072–5076).

In one version of the Lac system, expression of lac operator-linked sequences is constitutively activated by a LacR-VP16 fusion protein and is turned off in the presence of isopropyl-β-D-thiogalactopyranoside (IPTG) (Labow et al. (1990), cited supra). In another version of the system, a lacR-VP16 variant is used which binds to lac operators in the presence of IPTG, which can be enhanced by increasing the temperature of the cells (Baim et al.(1991), cited supra). The utility of these lac systems in eukaryotic cells is limited, in part, because IPTG acts slowly and inefficiently in eukaryotic cells and must be used at concentrations which approach cytotoxic levels. Alternatively, use of a temperature shift to induce gene expression is likely to elicit pleiotropic effects in the cells. Thus, there is a need for a more efficient inducible regulatory system which exhibits rapid and high level induction of gene expression and in which the inducer is tolerated by eukaryotic cells without cytotoxicity or pleiotropic effects.

Components of the tetracycline (Tc) resistance system of *E. coli* have also been found to function in eukaryotic cells and have been used to regulate gene expression. For example, the Tet repressor (TetR), which binds to tet operator sequences in the absence of tetracycline and represses gene transcription, has been expressed in plant cells at sufficiently high concentrations to repress transcription from a promoter containing tet operator sequences (Gatz, C. et al. (1992) *Plant J.* 2:397–404). However, very high intracellular concentrations of TetR are necessary to keep gene expression down-regulated in cells, which may not be achievable in many situations, thus leading to "leakiness" in the system.

In other studies, TetR has been fused to the activation domain of VP16 to create a tetracycline-controlled transcriptional activator (tTA) (Gossen, M. and Bujard, H. (1992) *Proc. Natl. Acad. Sci. USA* 89:5547–5551). The tTA fusion protein is regulated by tetracycline in the same manner as TetR, i.e., tTA binds to tet operator sequences in the absence of tetracycline but not in the presence of tetracycline. Thus, in this system, in the continuous presence of Tc, gene expression is kept off, and to induce transcription, Tc is removed.

SUMMARY OF THE INVENTION

This invention pertains to a regulatory system which utilizes components of the Tet repressor/operator/inducer system of prokaryotes to regulate gene expression in eukaryotic cells. In particular, this invention provides tetracycline-regulated fusion proteins which are useful for regulating expression, in a highly controlled manner, of a gene linked to one or more tet operator sequences. The invention further provides methods for using the regulatory system of the invention for regulating expression of a tet operator-linked gene in a cell of a subject. In a preferred embodiment, the method involves introducing into the cell a nucleic acid molecule encoding a fusion protein which inhibits transcription, the fusion protein comprising a first polypeptide which binds to a tet operator sequence, operatively linked to a heterologous second polypeptide which inhibits transcription in eukaryotic cells; and modulating the concentration of a tetracycline, or analogue thereof, in the subject. As used herein, the term "heterologous" used in reference to the second polypeptide is intended to indicate that the second polypeptide is derived from a different protein than the first polypeptide.

In one embodiment, the first polypeptide of the fusion protein binds to a tet operator sequences in the absence, but not the presence, of tetracycline. In another embodiment, the first polypeptide of the fusion protein binds to a tet operator sequences in the presence, but not the absence, of tetracycline.

The nucleic acid molecule encoding the fusion protein can be integrated randomly in a chromosome of the cell or, alternatively, at a predetermined location within a chromosome of the cell. Moreover, the nucleic acid molecule encoding the fusion protein can be introduced into the cell ex vivo and then administered to the subject.

The methods of the invention allow for regulation of a gene which is an endogenous gene of the cell which has been operatively linked to at least one tet operator sequence. Alternatively, the tet operator-linked gene can be an exogenous gene which has been introduced into the cells.

In another embodiment, the method involves obtaining a cell from a subject, modifying the cell ex vivo to contain one or more of the aforementioned nucleic acid molecules, administering the modified cell to the subject and modulating the concentration of a tetracycline, or analogue thereof, in the subject.

BRIEF DESCRIPTION OF THE DRAWINGS

FIG. 4 shows the amino acid sequences of various classes of Tet repressors, illustrating the homology between the amino acid sequences of different classes of Tet repressors, as compared to class B Tet repressors (e.g., Tn10-derived). Amino acid positions in other classes of Tet repressors that are identical to class B are indicated by a dash. The amino acid sequence of the class B repressor is set forth in SEQ ID NO:29; the class D repressor amino acid sequence is set forth in SEQ ID NO:30; the class A repressor amino acid sequence is set forth in SEQ ID NO:31, the class C repressor amino acid sequence is set forth in SEQ ID NO:32; the class G repressor is set forth in SEQ ID NO:33; and the class E repressor amino acid sequence is set forth in SEQ ID NO:34.

FIG. 5 shows the nucleotide sequences of tet operators of different classes: class A (SEQ ID NO: 11), class B (SEQ ID NO: 12), class C (SEQ ID NO: 13), class D (SEQ ID NO: 14) and class E (SEQ ID NO: 15).

FIG. 7A (SEQ ID NO: 6) shows the nucleotide sequence of a bidirectional promoter region for coordinate regulation of two genes of interest by a tetracycline-regulated transcriptional activator.

FIG. 9A illustrates self-regulation of expression of a wild-type Tet repressor-containing transactivator fusion protein that binds to tet operators in the absence of Tc. FIG. 9B illustrates self-regulation of expression of a mutated Tet repressor-containing transactivator fusion protein that binds to tet operators in the presence of Tc.

DETAILED DESCRIPTION OF THE INVENTION

Figure 1:
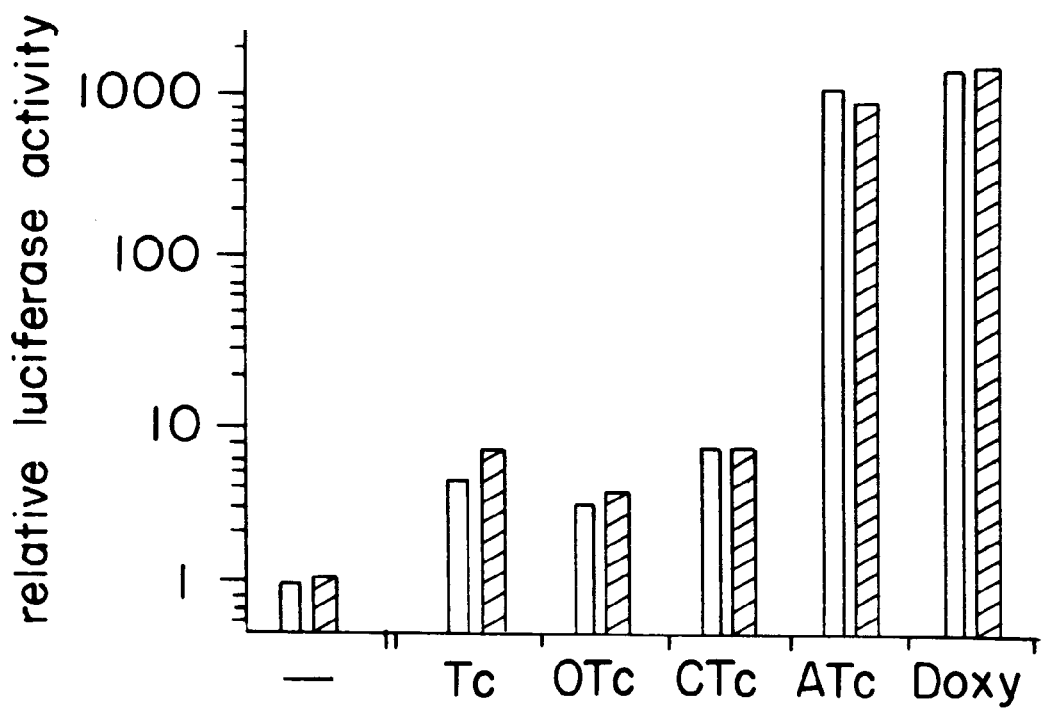
FIG. 1 is a bar graph depicting the stimulation of luciferase activity in HR5-C11 cells by tetracycline and different tetracycline analogues (1 μg/ml f.c.). Cells were grown in the absence (−) or presence of the indicated tetracyclines for 3 days before luciferase activity was determined. Each solid and hatched bar represents the luciferase activity of a single culture dish.

This invention pertains to nucleic acid molecules and proteins which can be used to regulate the expression of genes in eukaryotic cells or animals in a highly controlled manner. Regulation of gene expression by the system of the invention involves at least two components: A gene which is operatively linked to a regulatory sequence and a protein which, in either the presence or absence of an inducible agent, binds to the regulatory sequence and either activates or inhibits transcription of the gene. The system of the invention utilizes components of the Tet repressor/operator/ inducer system of prokaryotes to stimulate gene expression in eukaryotic cells.

Various aspects of the invention pertain to fusion proteins which are capable of either activating or inhibiting gene transcription when bound to tet operator (tetO) sequences, but which bind to tet operator sequences only in the presence or, alternatively, in the absence of tetracycline, or an analogue thereof. Thus, in a host cell, transcription of a gene operatively linked to a tet operator sequence(s) is stimulated or inhibited by a fusion protein of the invention by altering the concentration of tetracycline (or analogue) in contact with the host cell (e.g., adding or removing tetracycline from a culture medium, or administering or ceasing to administer tetracycline to a host organism, etc.).

The invention further pertains to target transcription units for regulation by the fusion protein of the invention. In addition to allowing for regulation of a single tet-operator linked gene of interest, the invention also provides novel transcription units containing two or more genes to be transcribed that can be regulated in either a coordinate or independent manner by a transactivator fusion protein of the invention. Methods for stimulating or inhibiting transcription of a gene using tetracycline (or analogues thereof), and kits which contain the components of the regulatory system described herein, are also encompassed by the invention.

In the following subsections, the nucleic acids and proteins comprising the components of the inducible regulatory system of the invention, and their interrelationship, are discussed in greater detail. The subsections are as follows:

I. Tetracycline-Inducible Transcriptional Activators
  A. The first polypeptide of the transactivator fusion protein
  B. The second polypeptide of the transactivator fusion protein
  C. A third polypeptide of the transactivator fusion protein
II. Expression of a Transactivator Fusion Protein
  A. Expression vectors
  B. Host cells
  C. Introduction of nucleic acid into host cells
  D. Transgenic Organisms
  E. Homologous Recombinant Organisms
III. Target Transcription Units Regulated by a Tetracycline-Inducible Transactivator
  A. Regulation of expression of tet operator-linked nucleotide sequences
  B. Coordinate regulation of two nucleotide sequences
  C. Independent regulation of mulitple nucleotide sequences
  D. Combined coordinate and independent regulation of multiple nucleotide sequences
IV. Tetracycline-Regulated Transcriptional Inhibitors
  A. The first polypeptide of the transcritional inhibitor fusion protein
  B. The second polypeptide of the transcritional inhibitor fusion protein
  C. A third polypeptide of the transcritional inhibitor fusion protein
  D. Expression of the transcriptional inhibitor fusion protein
V. Kits of the Invention
VI. Regulation of Gene Expression by Tetracycline or Analogues Thereof
  A. Stimulation of gene expression by transactivator fusion proteins
  B. Inhibition of gene expression by transcriptional inhibitor fusion proteins
  C. Combined positive and negative regulation of gene expression
VII. Applications of the Invention
  A. Gene Therapy
  B. Production of Proteins in Vitro
  C. Production of Proteins in Vivo
  D. Animal Models of Human Disease
  E. Production of Stable Cell Lines for Cloning
I. Tetracycline-Inducible Transcriptional Activators In the inducible regulatory system of the invention, transcription of a gene is activated by a transcriptional activator protein, also referred to herein simply as a transactivator. The transactivator of the invention is a fusion protein. One aspect of the invention thus pertains to fusion proteins and nucleic acids (e.g., DNA) encoding fusion proteins. The term "fusion protein" is intended to describe at least two polypeptides, typically from different sources, which are operatively linked. With regard to the polypeptides, the term "operatively linked" is intended to mean that the two polypeptides are connected in manner such that each polypeptide can serve its intended function. Typically, the two polypeptides are covalently attached through peptide bonds. The fusion protein is preferably produced by standard recombinant DNA techniques. For example, a DNA molecule encoding the first polypeptide is ligated to another DNA molecule encoding the second polypeptide, and the resultant hybrid DNA molecule is expressed in a host cell to produce the fusion protein. The DNA molecules are ligated to each other in a 5' to 3' orientation such that, after ligation, the translational frame of the encoded polypeptides is not altered (i.e., the DNA molecules are ligated to each other in-frame).

A. The First Polypeptide of the Transactivator Fusion Protein

The transactivator fusion protein of the invention is composed, in part, of a first polypeptide which binds to a tet operator sequence in the presence of tetracycline (Tc), or an analogue thereof. The first polypeptide of the fusion protein is preferably a mutated Tet repressor. The term "mutated Tet repressor" is intended to include polypeptides having an amino acid sequence which is similar to a wild-type Tet repressor but which has at least one amino acid difference from the wild-type Tet repressor. The term "wild-type Tet repressor" is intended to describe a protein occurring in nature which represses transcription from tet operator sequences in prokaryotic cells in the absence of Tc. The amino acid difference(s) between a mutated Tet repressor and a wild-type Tet repressor may be substitution of one or more amino acids, deletion of one or more amino acids or addition of one or more amino acids. The mutated Tet repressor of the invention has the following functional properties: 1) the polypeptide can bind to a tet operator sequence, i.e., it retains the DNA binding specificity of a wild-type Tet repressor; and 2) it is regulated in a reverse manner by tetracycline than a wild-type Tet repressor, i.e., the mutated Tet repressor binds to a tet operator sequence only the presence of Tc (or Tc analogue) rather than in the absence of Tc.

In a preferred embodiment, a mutated Tet repressor having the functional properties described above is created by substitution of amino acid residues in the sequence of a wild-type Tet repressor. For example, as described in Example 1, a Tn10-derived Tet repressor having amino acid substitutions at amino acid positions 71, 95, 101 and 102 has the desired functional properties and thus can be used as the first polypeptide in the transactivator fusion protein of the invention. The amino acid sequence of this mutated Tet repressor is shown in SEQ ID NO: 2 (positions 1–207). In one embodiment of the mutated Tet repressor, position 71 is mutated from glutamic acid to lysine, position 95 is mutated from aspartic acid to asparagine, position 101 is mutated from leucine to serine and position 102 is mutated from glycine to aspartic acid, although the invention is not limited to these particular mutations. Mutation of fewer than all four of these amino acid positions may be sufficient to achieve a Tet repressor with the desired functional properties. Accordingly, a Tet repressor is preferably mutated at at least one of these positions. Other amino acid substitutions, deletions or additions at these or other amino acid positions which retain the desired functional properties of the mutated Tet repressor are within the scope of the invention. The crystal structure of a Tet repressor-tetracycline complex, as described in Hinrichs, W. et al. (1994) *Science* 264:418–420, can be used for rational design of mutated Tet repressors. Based upon this structure, amino acid position 71 is located outside the tetracycline binding pocket, suggesting mutation at this site may not be necessary to achieve the desired functional properties of a mutated Tet repressor of the invention. In contrast, amino acid positions 95, 101 and 102 are located within the conserved tetracycline binding pocket. Thus, the tetracycline binding pocket of a Tet repressor may be targeted for mutation to create a mutated Tet repressor of the invention.

Additional mutated Tet repressors for incorporation into a fusion protein of the invention can be created according to the teachings of the invention. A number of different classes of Tet repressors have been described, e.g., A, B, C, D and E (of which the Tn10-encoded repressor is a class B repressor). The amino acid sequences of the different classes of Tet repressors share a high degree of homology (i.e., 40–60% across the length of the proteins), including in the region encompassing the above-described mutations. The amino acid sequences of various classes of Tet repressors are shown and compared in FIG. 4, and are also described in Tovar, K. et al. (1988) *Mol. Gen. Genet.* 215:76–80. Accordingly, equivalent mutations to those described above for the Tn10-derived Tet repressor can be made in other classes of Tet repressors for inclusion in a fusion protein of the invention. For example, amino acid position 95, which is an aspartic acid in all five repressor classes, can be mutated to asparagine in any class of repressor. Similarly, position 102, which is glycine in all five repressor classes, can be mutated to aspartic acid in any class of repressor. Additional suitable equivalent mutations will be apparent to those skilled in the art and can be created and tested for functionality by procedures described herein. Nucleotide and amino acid sequences of Tet repressors of the A, C, D and E classes are disclosed in Waters, S. H. et al. (1983) *Nucl. Acids Res* 11:6089–6105, Unger, B. et al. (1984) *Gene* 31: 103–108, Unger, B. et al. (1984) *Nucl Acids Res.* 12:7693–7703 and Tovar, K. et al. (1988) *Mol. Gen. Genet.* 215:76–80, respectively. These wild-type sequences can be mutated according to the teachings of the invention for use in the inducible regulatory system described herein.

Alternative to the above-described mutations, additional suitable mutated Tet repressors (i.e., having the desired functional properties described above) can be created by mutagenesis of a wild type Tet repressor and selection as described in Example 1. The nucleotide and amino acid sequences of wild-type class B Tet repressors are disclosed in Hillen, W. and Schollmeier, K. (1983) *Nucl. Acids Res.* 11:525–539 and Postle, K. et al. (1984) *Nucl. Acids Res.* 12:4849–4863. The nucleotide and amino acid sequences of wild-type class A, C, D and E type repressors are cited above. A mutated Tet repressor can be created and selected, for example as follows: a nucleic acid (e.g., DNA) encoding a wild-type Tet repressor is subjected to random mutagenesis and the resultant mutated nucleic acids are incorporated into an expression vector and introduced into a host cell for screening. A screening assay is used which allows for selection of a Tet repressor which binds to a tet operator sequence only in the presence of tetracycline. For example, a library of mutated nucleic acids in an expression vector can be introduced into an *E. coli* strain in which tet operator sequences control the expression of a gene encoding a Lac repressor and the Lac repressor controls the expression of a gene encoding an selectable marker (e.g., drug resistance). Binding of a Tet repressor to tet operator sequences in the bacteria will inhibit expression of the Lac repressor, thereby inducing expression of the selectable marker gene. Cells expressing the marker gene are selected based upon the selectable phenotype (e.g., drug resistance). For wild-type Tet repressors, expression of the selectable marker gene will occur in the absence of Tc. A nucleic acid encoding a mutated Tet repressor is selected using this system based upon the ability of the nucleic acid to induce expression of the selectable marker gene in the bacteria only in the presence of Tc.

A first polypeptide of the transactivator fusion protein (e.g., the mutated Tet repressor) has the property of binding specifically to a tet operator sequence. Each class of Tet repressor has a corresponding target tet operator sequence. Accordingly, the term "tet operator sequence" is intended to encompass all classes of tet operator sequences, e.g. class A, B, C, D, and E. Nucleotide sequences of these five classes of tet operators are shown in FIG. 5 and SEQ ID NOs: 11–15, and are described in Waters, S. H. et al. (1983) cited supra, Hillen, W. and Schollenmeier, K. (1983) cited supra, Stüber, D. and Bujard, H. (1981) *Proc. Natl. Acad. Sci. USA* 78:167–171, Unger, B. et al. (1984) cited supra and Tovar, K. et al. (1988) cited supra. In a preferred embodiment, the mutated Tet repressor is a Tn10-encoded repressor (i.e., class B) and the tet operator sequence is a class B tet operator sequence. Alternatively, a mutated class A Tet repressor can be used with a class A tet operator sequence, and so on for the other classes of Tet repressor/operators.

Another approach for creating a mutated Tet repressor which binds to a class A tet operator is to further mutate the already mutated Tn10-derived Tet repressor described herein (a class B repressor) such that it no longer binds efficiently to a class B type operator but instead binds efficiently to a class A type operator. It has been found that nucleotide position 6 of class A or B type operators is the critical nucleotide for recognition of the operator by its complimentary repressor (position 6 is a G/C pair in class B operators and an A/T pair in class A operators) (see Wissman et al. (1988) *J. Mol. Biol.* 202:397–406). It has also been found that amino acid position 40 of a class A or class B Tet repressor is the critical amino acid residue for recognition of position 6 of the operator (amino acid position 40 is a threonine in class B repressors but is an alanine in class A repressors). It still further has been found that substitution of Thr40 of a class B repressor with Ala alters its binding specificity such that the repressor can now bind a class A operator (similarly, substitution of Ala40 of a class A repressor with Thr alters its binding specificity such that the repressor can now bind a class B operator) (see Altschmied et al. (1988) *EMBO J.* 7:4011–4017). Accordingly, one can alter the binding specificity of the mutated Tn10-derived Tet repressor disclosed herein by additionally changing amino acid residue 40 from Thr to Ala by standard molecular biology techniques (e.g., site directed mutagenesis).

A mutated Tet repressor having specific mutations (e.g., at positions 71, 95, 101 and/or 102, as described above) can be created by introducing nucleotide changes into a nucleic acid encoding a wild-type repressor by standard molecular biology techniques, e.g. site directed mutagenesis or PCR-mediated mutagenesis using oligonucleotide primers incorporating the nucleotide mutations. Alternatively, when a mutated Tet repressor is identified by selection from a library, the mutated nucleic acid can be recovered from the library vector. To create a transactivator fusion protein of the invention, a nucleic acid encoding a mutated Tet repressor is then ligated in-frame to another nucleic acid encoding a transcriptional activation domain and the fusion construct is incorporated into a recombinant expression vector. The transactivator fusion protein can be expressed by introducing the recombinant expression vector into a host cell or animal.

B. The Second Polypeptide of the Transactivator Fusion Protein

The first polypeptide of the transactivator fusion protein is operatively linked to a second polypeptide which directly or indirectly activates transcription in eukaryotic cells. To operatively link the first and second polypeptides, typically nucleotide sequences encoding the first and second polypeptides are ligated to each other in-frame to create a chimeric gene encoding a fusion protein, although the first and second polypeptides can be operatively linked by other means that preserve the function of each polypeptide (e.g., chemically crosslinked). In a preferred embodiment, the second polypeptide of the transactivator itself possesses transcriptional activation activity (i.e., the second polypeptide directly activates transcription). In another embodiment, the second polypeptide activates transcription by an indirect mechanim, through recruitment of a transcriptional activation protein to interact with the fusion protein. Accordingly, the term "a polypeptide which activates transcription in eukaryotic cells" as used herein is intended to include polypeptides which either directly or indirectly activates transcription.

Polypeptides which can function to activate transcription in eukaryotic cells are well known in the art. In particular, transcriptional activation domains of many DNA binding proteins have been described and have been shown to retain their activation function when the domain is transferred to a heterologous protein. A preferred polypeptide for use in the fusion protein of the invention is the herpes simplex virus virion protein 16 (referred to herein as VP16, the amino acid sequence of which is disclosed in Triezenberg, S. J. et al. (1988) *Genes Dev.* 2:718–729). In one embodiment, about 127 of the C-terminal amino acids of VP16 are used. For example, a polypeptide having an amino acid sequence shown in SEQ ID NO: 2 (positions 208–335) can be used as the second polypeptide in the fusion protein. In another embodiment, at least one copy of about 11 amino acids from the C-terminal region of VP16 which retain transcriptional activation ability is used as the second polypeptide. Preferably, a dimer of this region (i.e., about 22 amino acids) is used. Suitable C-terminal peptide portions of VP16 are described in Seipel, K. et al. (*EMBO J.* (1992) 13:4961–4968). For example, a dimer of a peptide having an amino acid sequence shown in SEQ ID NO: 4 (encoded by a nucleotide sequence shown in SEQ ID NO: 3) can be used as the second polypeptide in the fusion protein.

Other polypeptides with transcriptional activation ability in eukaryotic cells can be used in the fusion protein of the invention. Transcriptional activation domains found within various proteins have been grouped into categories based upon similar structural features. Types of transcriptional activation domains include acidic transcription activation domains, proline-rich transcription activation domains, serine/threonine-rich transcription activation domains and glutamine-rich transcription activation domains. Examples of acidic transcriptional activation domains include the VP16 regions already described and amino acid residues 753–881 of GAL4. Examples of proline-rich activation domains include amino acid residues 399–499 of CTF/NF1 and amino acid residues 31–76 of AP2. Examples of serine/threonine-rich transcription activation domains include amino acid residues 1–427 of ITF1 and amino acid residues 2–451 of ITF2. Examples of glutamine-rich activation domains include amino acid residues 175–269 of Oct1 and amino acid residues 132–243 of Sp1. The amino acid sequences of each of the above described regions, and of other useful transcriptional activation domains, are disclosed in Seipel, K. et al. (*EMBO J.* (1992) 13:4961–4968).

In addition to previously described transcriptional activation domains, novel transcriptional activation domains, which can be identified by standard techniques, are within the scope of the invention. The transcriptional activation ability of a polypeptide can be assayed by linking the polypeptide to another polypeptide having DNA binding activity and determining the amount of transcription of a target sequence that is stimulated by the fusion protein. For example, a standard assay used in the art utilizes a fusion protein of a putative transcriptional activation domain and a GAL4 DNA binding domain (e.g., amino acid residues 1–93). This fusion protein is then used to stimulate expression of a reporter gene linked to GAL4 binding sites (see e.g., Seipel, K. et al. (1992) *EMBO J.* 11:4961–4968 and references cited therein).

In another embodiment, the second polypeptide of the fusion protein indirectly activates transcription by recruiting a transcriptional activator to interact with the fusion protein. For example, a mutated tetR of the invention can be fused to a polypeptide domain (e.g., a dimerization domain) capable of mediating a protein-protein interaction with a transcriptional activator protein, such as an endogenous activator present in a host cell. It has been demonstrated that functional associations between DNA binding domains and transactivation domains need not be covalent (see e.g., Fields and Song (1989) *Nature* 340:245–247; Chien et al. (1991) *Proc. Natl. Acad. Sci. USA* 88:9578–9582; Gyuris et al. (1993) *Cell* 75:791–803; and Zervos, A. S. (1993) *Cell* 72:223–232). Accordingly, the second polypeptide of the fusion protein may not directly activate transcription but rather may form a stable interaction with an endogenous polypeptide bearing a compatible protein-protein interaction domain and transactivation domain. Examples of suitable interaction (or dimerization) domains include leucine zippers (Landschulz et al. (1989) *Science* 243:1681–1688), helix-loop-helix domains (Murre, C. et al. (1989) *Cell* 58:537–544) and zinc finger domains (Frankel, A. D. et al. (1988) *Science* 240:70–73). Interaction of a dimerization domain present in the fusion protein with an endogenous nuclear factor results in recruitment of the transactivation domain of the nuclear factor to the fusion protein, and thereby to a tet operator sequence to which the fusion protein is bound.

C. A Third Polypeptide of the Transactivator Fusion Protein

In addition to a mutated Tet repressor and a transcriptional activation domain, a fusion protein of the invention can contain an operatively linked third polypeptide which promotes transport of the fusion protein to a cell nucleus. Amino acid sequences which, when included in a protein, function to promote transport of the protein to the nucleus are known in the art and are termed nuclear localization signals (NLS). Nuclear localization signals typically are composed of a stretch of basic amino acids. When attached to a heterologous protein (e.g., a fusion protein of the invention), the nuclear localization signal promotes transport of the protein to a cell nucleus. The nuclear localization signal is attached to a heterologous protein such that it is exposed on the protein surface and does not interfere with the function of the protein. Preferably, the NLS is attached to one end of the protein, e.g. the N-terminus. The amino acid sequence of a non-limiting Example of an NLS that can be included in a fusion protein of the invention is shown in SEQ ID NO: 5. Preferably, a nucleic acid encoding the nuclear localization signal is spliced by standard recombinant DNA techniques in-frame to the nucleic acid encoding the fusion protein (e.g., at the 5' end).

The plasmid pUHD17-1 (described in further detail in Example 1), which comprises a transactivator of the invention having the nucleotide sequence shown in SEQ ID NO: 1, has been deposited on Jul. 8, 1994 under the provisions of the Budapest Treaty at the Deutsche Sammlung Von Mikroorganismen und ZellKulturen GmbH (DSM) in Braunschweig, Germany and assigned deposit number DSM 9279.

II. Expression of a Transactivator Fusion Protein

A. Expression Vectors

A nucleic acid of the invention encoding a transactivator fusion protein, as described above, can be incorporated into a recombinant expression vector in a form suitable for expression of the fusion protein in a host cell. The term "in a form suitable for expression of the fusion protein in a host cell" is intended to mean that the recombinant expression vector includes one or more regulatory sequences operatively linked to the nucleic acid encoding the fusion protein in a manner which allows for transcription of the nucleic acid into mRNA and translation of the mRNA into the fusion protein. The term "regulatory sequence" is art-recognized and intended to include promoters, enhancers and other expression control elements (e.g., polyadenylation signals). Such regulatory sequences are known to those skilled in the art and are described in Goeddel, *Gene Expression Technology: Methods in Enzymology* 185, Academic Press, San Diego, Calif. (1990). It should be understood that the design of the expression vector may depend on such factors as the choice of the host cell to be transfected and/or the amount of fusion protein to be expressed.

When used in mammalian cells, a recombinant expression vector's control functions are often provided by viral genetic material. For example, commonly used promoters are derived from polyoma, Adenovirus 2, cytomegalovirus and Simian Virus 40. Use of viral regulatory elements to direct expression of the fusion protein can allow for high level constitutive expression of the fusion protein in a variety of host cells. In a preferred recombinant expression vector, the sequences encoding the fusion protein are flanked upstream (i.e., 5') by the human cytomegalovirus IE promoter and downstream (i.e., 3') by an SV40 poly(A) signal. For example, an expression vector similar to that described in Example 1 can be used. The human cytomegalovirus IE promoter is described in Boshart et al. (1985) *Cell* 41:521–530. Other ubiquitously expressing promoters which can be used include the HSV-Tk promoter (disclosed in McKnight et al. (1984) *Cell* 37:253–262) and β-actin promoters (e.g., the human β-actin promoter as described by Ng et al. (1985) *Mol. Cell. Biol.* 5:2720–2732).

Alternatively, the regulatory sequences of the recombinant expression vector can direct expression of the fusion protein preferentially in a particular cell type, i.e., tissue-specific regulatory elements can be used. Non-limiting examples of tissue-specific promoters which can be used include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

Figure 9A:
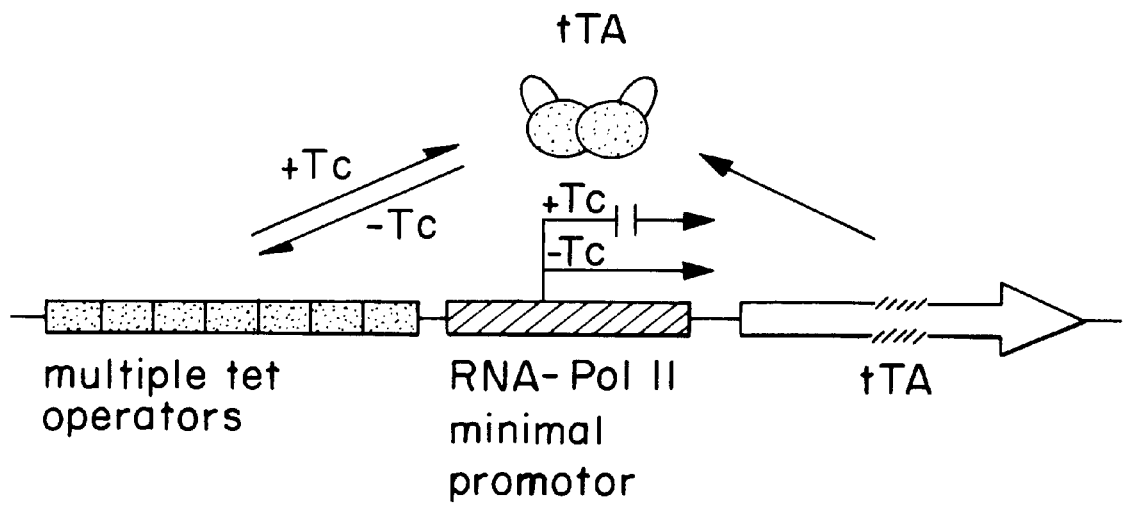
FIGS. 9A–9B are schematic diagrams of self-regulating promoters for expression of tetracycline-regulated transcriptional activators (tTA).
Figure 9B:
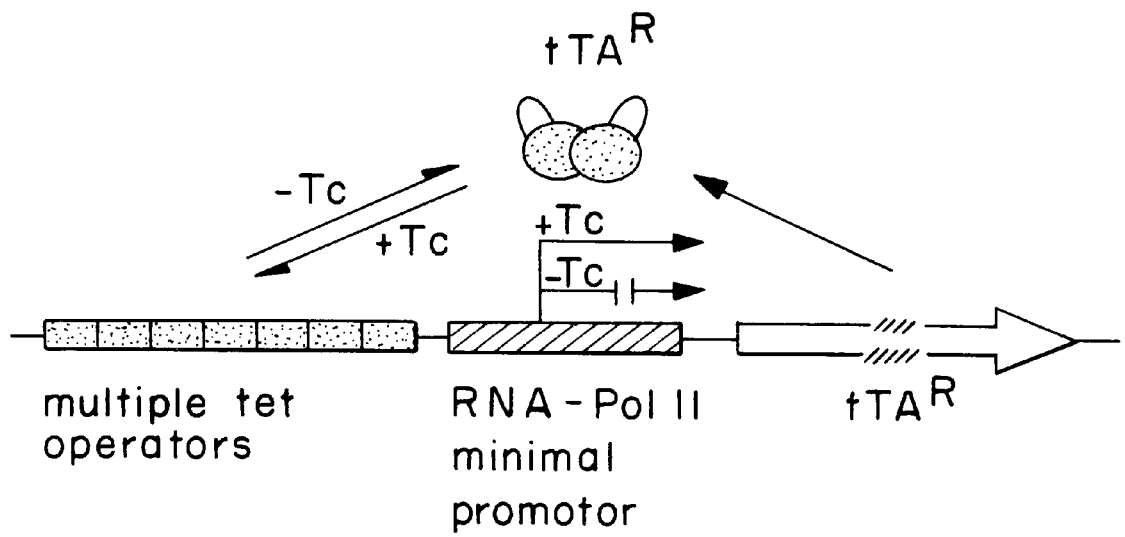

Alternatively, a self-regulating construct encoding a transactivator fusion protein can be created. To accomplish this, nucleic acid encoding the fusion protein is operatively linked to a minimal promoter sequence and at least one tet operator sequence. For example, the nucleic acid of SEQ ID NO: 1 can be linked to a promoter having a nucleotide sequence shown in SEQ ID NO: 8, 9 or 10 (the nucleic acids of SEQ ID NOs: 8 and 9 comprise a minimal CMV promoter and ten tet operators; the nucleic acids of SEQ ID NO: 10 comprises a TK promoter and ten tet operators). A schematic diagram of such a self-regulating construct is shown in FIG. 9B. When this nucleic acid is introduced into a cell (e.g., in a recombinant expression vector), a small amount of basal transcription of the transactivator gene is likely to occur due to "leakiness". In the presence of Tc (or analogue thereof) this small amount of the transactivator fusion protein will bind to the tet operator sequence(s) upstream of the nucleotide sequence encoding the transactivator and stimulate additional transcription of the nucleotide sequence encoding the transactivator, thereby leading to further production of the transactivator fusion protein in the cell. It will be appreciated by those skilled in the art that such a self-regulating promoter can also be used in conjunction with other tetracycline-regulated transactivators, such as the wild-type Tet repressor fusion protein (tTA) described in Gossen, M. and Bujard, H. (1992) *Proc. Natl. Acad. Sci. USA* 89:5547–5551, which binds to tet operators in the absence of Tc (as illustrated in FIG. 9A). When used in conjunction with this transactivator, self-regulated transcription of the nucleotide sequence encoding this transactivator is stimulated in the absence of Tc. The plasmid pUHD15-3, which comprises nucleotide sequences encoding the tTA described in Gossen and Bujard (1992), cited supra, operatively linked to a self-regulating promoter, has been deposited on Jul. 8, 1994 under the provisions of the Budapest Treaty at the Deutsche Sammlung Von Mikroorganismen und ZellKulturen GmbH (DSM) in Braunschweig, Germany and assigned deposit number DSM 9280.

In one embodiment, the recombinant expression vector of the invention is a plasmid, such as that described in Example 1. Alternatively, a recombinant expression vector of the invention can be a virus, or portion thereof, which allows for expression of a nucleic acid introduced into the viral nucleic acid. For example, replication defective retroviruses, adenoviruses and adeno-associated viruses can be used. Protocols for producing recombinant retroviruses and for infecting cells in vitro or in vivo with such viruses can be found in *Current Protocols in Molecular Biology,* Ausubel, F. M. et al. (eds.) Greene Publishing Associates, (1989), Sections 9.10–9.14 and other standard laboratory manuals. Examples of suitable retroviruses include pLJ, pZIP, pWE and pEM which are well known to those skilled in the art. Examples of suitable packaging virus lines include ψCrip, ψCre, ψ2 and ψAm. The genome of adenovirus can be manipulated such that it encodes and expresses a transactivator fusion protein but is inactivated in terms of its ability to replicate in a normal lytic viral life cycle. See for example Berkner et al. (1988) *BioTechniques* 6:616; Rosenfeld et al. (1991) *Science* 252:431–434; and Rosenfeld et al. (1992) *Cell* 68:143–155. Suitable adenoviral vectors derived from the adenovirus strain Ad type 5 dl324 or other strains of adenovirus (e.g., Ad2, Ad3, Ad7 etc.) are well known to those skilled in the art. Alternatively, an adeno-associated virus vector such as that described in Tratschin et al. (1985) *Mol. Cell. Biol.* 5:3251–3260 can be used to express a transactivator fusion protein.

B. Host Cells

A fusion protein of the invention is expressed in a eukaryotic cell by introducing nucleic acid encoding the fusion protein into a host cell, wherein the nucleic acid is in a form suitable for expression of the fusion protein in the host cell. For example, a recombinant expression vector of the invention, encoding the fusion protein, is introduced into a host cell. Alternatively, nucleic acid encoding the fusion protein which is operatively linked to regulatory sequences (e.g., promoter sequences) but without additional vector sequences can be introduced into a host cell. As used herein, the term "host cell" is intended to include any eukaryotic cell or cell line so long as the cell or cell line is not incompatible with the protein to be expressed, the selection system chosen or the fermentation system employed. Non-limiting examples of mammalian cell lines which can be used include CHO dhfr cells (Urlaub and Chasin (1980) *Proc. Natl. Acad. Sci. USA* 77:4216–4220), 293 cells (Graham et al. (1977) *J. Gen. Virol.* 36: pp59) or myeloma cells like SP2 or NS0 (Galfre and Milstein (1981) *Meth. Enzymol.* 73(B):3–46).

In addition to cell lines, the invention is applicable to normal cells, such as cells to be modified for gene therapy purposes or embryonic cells modified to create a transgenic or homologous recombinant animal. Examples of cell types of particular interest for gene therapy purposes include hematopoietic stem cells, myoblasts, hepatocytes, lymphocytes, neuronal cells and skin epithelium and airway epithelium. Additionally, for transgenic or homologous recombinant animals, embryonic stem cells and fertilized oocytes can be modified to contain nucleic acid encoding a transactivator fusion protein. Moreover, plant cells can be modified to create transgenic plants.

The invention is broadly applicable and encompasses non-mammalian eukaryotic cells as well, including insect (e.g,. Sp. frugiperda), yeast (e.g., *S. cerevisiae, S. pombe, P. pastoris, K. lactis, H. polymorpha;* as generally reviewed by Fleer, R. (1992) *Current Opinion in Biotechnology* 3(5):486–496)), fungal and plant cells. Examples of vectors for expression in yeast *S. cerivisae* include pYepSec1 (Baldari. et al., (1987) *Embo J.* 6:229–234), pMFa (Kurjan and Herskowitz, (1982) *Cell* 30:933–943), pJRY88 (Schultz et al., (1987) *Gene* 54:113–123), and pYES2 (Invitrogen Corporation, San Diego, Calif.). The fusion protein can be expressed in insect cells using baculovirus expression vectors (e.g., as described in O'Reilly et al. (1992) *Baculovirus Expression Vectors: A Laboratory Manual,* Stockton Press). Baculovirus vectors available for expression of proteins in cultured insect cells (e.g., SF9 cells) include the pAc series (Smith et al., (1983) *Mol. Cell Biol.* 3:2156–2165) and the pVL series (Lucklow, V. A., and Summers, M. D., (1989) *Virology* 170:31–39).

C. Introduction of Nucleic Acid into a Host Cell

Nucleic acid encoding the fusion protein can be introduced into a host cell by standard techniques for transfecting eukaryotic cells. The term "transfecting" or "transfection" is intended to encompass all conventional techniques for introducing nucleic acid into host cells, including calcium phosphate co-precipitation, DEAE-dextran-mediated transfection, lipofection, electroporation and microinjection. Suitable methods for transfecting host cells can be found in Sambrook et al. (*Molecular Cloning: A Laboratory Manual,* 2nd Edition, Cold Spring Harbor Laboratory press (1989)), and other laboratory textbooks.

The number of host cells transformed with a nucleic acid of the invention will depend, at least in part, upon the type of recombinant expression vector used and the type of transfection technique used. Nucleic acid can be introduced into a host cell transiently, or more typically, for long term regulation of gene expression, the nucleic acid is stably integrated into the genome of the host cell or remains as a stable episome in the host cell. Plasmid vectors introduced into mammalian cells are typically integrated into host cell DNA at only a low frequency. In order to identify these integrants, a gene that contains a selectable marker (e.g., drug resistance) is generally introduced into the host cells along with the nucleic acid of interest. Preferred selectable markers include those which confer resistance to certain drugs, such as G418 and hygromycin. Selectable markers can be introduced on a separate plasmid from the nucleic acid of interest or, are introduced on the same plasmid. Host cells transfected with a nucleic acid of the invention (e.g., a recombinant expression vector) and a gene for a selectable marker can be identified by selecting for cells using the selectable marker. For example, if the selectable marker encodes a gene conferring neomycin resistance, host cells which have taken up nucleic acid can be selected with G418. Cells that have incorporated the selectable marker gene will survive, while the other cells die.

A host cell transfected with a nucleic acid encoding a fusion protein of the invention can be further transfected with one or more nucleic acids which serve as the target for the fusion protein. The target nucleic acid comprises a nucleotide sequence to be transcribed operatively linked to at least one tet operator sequence (described in more detail in Section III below).

Nucleic acid encoding the fusion protein of the invention can be introduced into eukaryotic cells growing in culture in vitro by conventional transfection techniques (e.g., calcium phosphate precipitation, DEAE-dextran transfection, electroporation etc.). Nucleic acid can also be transferred into cells in vivo, for example by application of a delivery mechanism suitable for introduction of nucleic acid into cells in vivo, such as retroviral vectors (see e.g., Ferry, N et al. (1991) *Proc. Natl. Acad. Sci. USA* 88:8377–8381; and Kay, M. A. et al. (1992) *Human Gene Therapy* 3:641–647), adenoviral vectors (see e.g., Rosenfeld, M. A. (1992) *Cell* 68:143–155; and Herz, J. and Gerard, R. D. (1993) *Proc.*

*Natl. Acad. Sci. USA* 90:2812–2816), receptor-mediated DNA uptake (see e.g., Wu, G. and Wu, C. H. (1988) *J. Biol. Chem.* 263:14621; Wilson et al. (1992) *J. Biol. Chem.* 267:963–967; and U.S. Pat. No. 5,166,320), direct injection of DNA (see e.g., Acsadi et al. (1991) *Nature* 332: 815–818; and Wolff et al. (1990) *Science* 247:1465–1468) or particle bombardment (see e.g., Cheng, L. et al. (1993) *Proc. Natl. Acad. Sci. USA* 90:4455–4459; and Zelenin, A. V. et al. (1993) *FEBS Letters* 315:29–32). Thus, for gene therapy purposes, cells can be modified in vitro and administered to a subject or, alternatively, cells can be directly modified in vivo.

D. Transgenic Organisms

Nucleic acid a transactivator fusion protein can transferred into a fertilized oocyte of a non-human animal to create a transgenic animal which expresses the fusion protein of the invention in one or more cell types. A transgenic animal is an animal having cells that contain a transgene, wherein the transgene was introduced into the animal or an ancestor of the animal at a prenatal, e.g., an embryonic, stage. A transgene is a DNA which is integrated into the genome of a cell from which a transgenic animal develops and which remains in the genome of the mature animal, thereby directing the expression of an encoded gene product in one or more cell types or tissues of the transgenic animal. In one embodiment, the non-human animal is a mouse, although the invention is not limited thereto. In other embodiments, the transgenic animal is a goat, sheep, pig, cow or other domestic farm animal. Such transgenic animals are useful for large scale production of proteins (so called "gene pharming").

A transgenic animal can be created, for example, by introducing a nucleic acid encoding the fusion protein (typically linked to appropriate regulatory elements, such as a constitutive or tissue-specific enhancer) into the male pronuclei of a fertilized oocyte, e.g., by microinjection, and allowing the oocyte to develop in a pseudopregnant female foster animal. Intronic sequences and polyadenylation signals can also be included in the transgene to increase the efficiency of expression of the transgene. Methods for generating transgenic animals, particularly animals such as mice, have become conventional in the art and are described, for example, in U.S. Pat. Nos. 4,736,866 and 4,870,009 and Hogan, B. et al., (1986) *A Laboratory Manual,* Cold Spring Harbor, N.Y., Cold Spring Harbor Laboratory. A transgenic founder animal can be used to breed additional animals carrying the transgene. Transgenic animals carrying a transgene encoding the fusion protein of the invention can further be bred to other transgenic animals carrying other transgenes, e.g., to a transgenic animal which contains a gene operatively linked to a tet operator sequence (discussed in more detail in Section III below).

It will be appreciated that, in addition to transgenic animals, the regulatory system described herein can be applied to other transgenic organisms, such as transgenic plants. Transgenic plants can be made by conventional techniques known in the art. Accordingly, the invention encompasses non-human transgenic organisms, including animals and plants, that contains cells which express the transactivator fusion protein of the invention (i.e., a nucleic acid encoding the transactivator is incorporated into one or more chromosomes in cells of the transgenic organism).

E. Homologous Recombinant Organisms

The invention also provides a homologous recombinant non-human organism expressing the fusion protein of the invention. The term "homologous recombinant organism" as used herein is intended to describe an organism, e.g. animal or plant, containing a gene which has been modified by homologous recombination between the gene and a DNA molecule introduced into a cell of the animal, e.g., an embryonic cell of the animal. In one embodiment, the non-human animal is a mouse, although the invention is not limited thereto. An animal can be created in which nucleic acid encoding the fusion protein has been introduced into a specific site of the genome, i.e., the nucleic acid has homologously recombined with an endogenous gene.

To create such a homologous recombinant animal, a vector is prepared which contains DNA encoding the fusion protein flanked at its 5' and 3' ends by additional nucleic acid of a eukaryotic gene at which homologous recombination is to occur. The additional nucleic acid flanking that encoding the fusion protein is of sufficient length for successful homologous recombination with the eukaryotic gene. Typically, several kilobases of flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced DNA has homologously recombined with the endogenous DNA are selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach,* E. J. Robertson, ed. (IRL, Oxford, 1987) pp. 113–152). A chimeric embryo can then be implanted into a suitable pseudopregnant female foster animal and the embryo brought to term. Progeny harbouring the homologously recombined DNA in their germ cells can be used to breed animals in which all cells of the animal contain the homologously recombined DNA. These "germline transmission" animals can further be mated to animals carrying a gene operatively linked to at least one tet operator sequence (discussed in more detail in Section III below).

In addition to the homologous recombination approaches described above, enzyme-assisted site-specific integration systems are known in the art and can be applied to the components of the regulatory system of the invention to integrate a DNA molecule at a predetermined location in a second target DNA molecule. Examples of such enzyme-assisted integration systems include the Cre recombinase-lox target system (e.g., as described in Baubonis, W. and Sauer, B. (1993) *Nucl. Acids Res.* 21:2025–2029; and Fukushige, S. and Sauer, B. (1992) *Proc. Natl. Acad. Sci. USA* 89:7905–7909) and the FLP recombinase-FRT target system (e.g., as described in Dang, D. T. and Perrimon, N. (1992) *Dev. Genet.* 13:367–375; and Fiering, S. et al. (1993) *Proc. Natl. Acad. Sci. USA* 90:8469–8473).

III. Target Transcription Units Regulated by a Tetracycline-Inducible Transactivator A fusion protein of the invention is used to regulate the transcription of a target nucleotide sequence. This target nucleotide sequence is operatively linked to a regulatory sequence to which the fusion protein binds. More specifically, the fusion protein regulates expression of a nucleotide sequence operatively linked to at least one tet operator sequence. Accordingly, another aspect of the invention relates to target nucleic acids (e.g., DNA molecules) comprising a nucleotide sequence to be transcribed operatively linked to at least one tet operator sequence. Such nucleic acids are also referred to herein as tet-regulated transcription units (or simply transcription units).

Within a transcription unit, the "nucleotide sequence to be transcribed" typically includes a minimal promoter sequence which is not itself transcribed but which serves (at least in part) to position the transcriptional machinery for transcription. The minimal promoter sequence is linked to the transcribed sequence in a 5' to 3' direction by phosphodiester bonds (i.e., the promoter is located upstream of the transcribed sequence) to form a contiguous nucleotide sequence. Accordingly, as used herein, the terms "nucleotide sequence to be transcribed" or "target nucleotide sequence" are intended to include both the nucleotide sequence which is transcribed into mRNA and an operatively linked upstream minimal promoter sequence. The term "minimal promoter" is intended to describe a partial promoter sequence which defines the start site of transcription for the linked sequence to be transcribed but which by itself is not capable of initiating transcription efficiently, if at all. Thus, the activity of such a minimal promoter is dependent upon the binding of a transcriptional activator (such as the tetracycline-inducible fusion protein of the invention) to an operatively linked regulatory sequence (such as one or more tet operator sequences). In one embodiment, the minimal promoter is from the human cytomegalovirus (as described in Boshart et al. (1985) *Cell* 41:521–530). Preferably, nucleotide positions between about +75 to −53 and +75 to −31 are used. Other suitable minimal promoters are known in the art or can be identified by standard techniques. For example, a functional promoter which activates transcription of a contiguously linked reporter gene (e.g., chloramphenicol acetyl transferase, β-galactosidase or luciferase) can be progressively deleted until it no longer activates expression of the reporter gene alone but rather requires the presence of an additional regulatory sequence(s).

Within a transcription unit, the target nucleotide sequence (including the transcribed nucleotide sequence and its upstream minimal promoter sequence) is operatively linked to at least one tet operator sequence. In a typical configuration, the tet operator sequence(s) is operatively linked upstream (i.e., 5') of the minimal promoter sequence through a phosphodiester bond at a suitable distance to allow for transcription of the target nucleotide sequence upon binding of a regulatory protein (e.g., the transactivator fusion protein) to the tet operator sequence. That is, the transcription unit is comprised of, in a 5' to 3' direction: tet operator sequence(s)—a minimal promoter—a transcribed nucleotide sequence. It will be appreciated by those skilled in the art that there is some flexibility in the permissible distance between the tet operator sequence(s) and the minimal promoter, although typically the tet operator sequences will be located within about 200–400 base pairs upstream of the minimal promoter.

The nucleotide sequences of examples of tet-regulated promoters, containing tet operator sequences linked to a minimal promoter, that can be used in the invention are shown in SEQ ID NO: 8–10. The nucleotide sequences of SEQ ID NOs: 8 and 9 comprise a cytomegalovirus minimal promoter linked to ten tet operator sequences; the two nucleotide sequences differ in the distance between the operators and the first transcribed nucleotide. The nucleotide sequence of SEQ ID NO: 10 comprises a herpes simplex virus minimal tk promoter linked to ten tet operator sequences. The promoter of SEQ ID NO: 8 corresponds to $P_{hCMV}^*$-1, described in Gossen, M. and Bujard, H. (1992) *Proc. Natl. Acad. Sci. USA* 89:5547–5551. The promoter of SEQ ID NO: 9 corresponds to $P_{hCMV}^*$-2, also described in Gossen, M. and Bujard, H, cited supra.

Alternatively, since regulatory elements have been observed in the art to function downstream of sequences to be transcribed, it is likely that the tet operator sequence(s) can be operatively linked downstream (i.e., 3') of the transcribed nucleotide sequence. Thus, in this configuration, the transcription unit is comprised of, in a 5' to 3' direction: a minimal promoter—a transcribed nucleotide sequence—tet operator sequence(s). Again, it will be appreciated that there is likely to be some flexibility in the permissible distance downstream at which the tet operator sequence(s) can be linked.

The term "tet operator sequence" is intended to encompass all classes of tet operators (e.g., A, B, C, D and E). A nucleotide sequence to be transcribed can be operatively linked to a single tet operator sequence, or for an enhanced range of regulation, it can be operatively linked to multiple tet operator sequences (e.g., two, three, four, five, six, seven, eight, nine, ten or more operator sequences). In a preferred embodiment, the sequence to be transcribed is operatively linked to seven tet operator sequences.

A tet-regulated transcription unit can further be incorporated into a recombinant vector (e.g., a plasmid or viral vector) by standard recombinant DNA techniques. The transcription unit, or recombinant vector in which it is contained, can be introduced into a host cell by standard transfection techniques, such as those described above. It should be appreciated that, after introduction of the transcription unit into a population of host cells, it may be necessary to select a host cell clone which exhibit low basal expression of the tet operator-linked nucleotide sequence (i.e., selection for a host cell in which the transcription unit has integrated at a site that results in low basal expression of the tet operator-linked nucleotide sequence). Furthermore, a tet-regulated transcription unit can be introduced, by procedures described above, into the genome of a non-human animal at an embryonic stage or into plant cells to create a transgenic or homologous recombinant organim carrying the transcription unit in some or all of its cells. Again, it should be appreciated that it may be necessary to select a transgenic or homologous organism in which there is low basal expression of tet operator-linked nucleotide sequence in cells of interest.

In one embodiment, the target nucleotide sequence of the tet-regulated transcription unit encodes a protein of interest. Thus, upon induction of transcription of the nucleotide sequence by the transactivator of the invention and translation of the resultant mRNA, the protein of interest is produced in a host cell or animal. Alternatively, the nucleotide sequence to be transcribed can encode for an active RNA molecule, e.g., an antisense RNA molecule or ribozyme. Expression of active RNA molecules in a host cell or animal can be used to regulate functions within the host (e.g., prevent the production of a protein of interest by inhibiting translation of the mRNA encoding the protein).

A transactivator of the invention can be used to regulate transcription of an exogenous nucleotide sequence introduced into the host cell or animal. An "exogenous" nucleotide sequence is a nucleotide sequence which is introduced into the host cell and typically is inserted into the genome of the host. The exogenous nucleotide sequence may not be present elsewhere in the genome of the host (e.g., a foreign nucleotide sequence) or may be an additional copy of a sequence which is present within the genome of the host but which is integrated at a different site in the genome. An exogenous nucleotide sequence to be transcribed and an operatively linked tet operator sequence(s) can be contained within a single nucleic acid molecule which is introduced into the host cell or animal.

Alternatively, a transactivator of the invention can be used to regulate transcription of an endogenous nucleotide sequence to which a tet operator sequence(s) has been linked. An "endogenous" nucleotide sequence is a nucleotide sequence which is present within the genome of the host. An endogenous gene can be operatively linked to a tet operator sequence(s) by homologous recombination between a tetO-containing recombination vector and sequences of the endogeneous gene. For example, a homologous recombination vector can be prepared which includes at least one tet operator sequence and a miminal promoter sequence flanked at its 3' end by sequences representing the coding region of the endogenous gene and flanked at its 5' end by sequences from the upstream region of the endogenous gene by excluding the actual promoter region of the endogenous gene. The flanking sequences are of sufficient length for successful homologous recombination of the vector DNA with the endogenous gene. Preferably, several kilobases of flanking DNA are included in the homologous recombination vector. Upon homologous recombination between the vector DNA and the endogenous gene in a host cell, a region of the endogenous promoter is replaced by the vector DNA containing one or more tet operator sequences operably linked to a minimal promoter. Thus, expression of the endogenous gene is no longer under the control of its endogenous promoter but rather is placed under the control of the tet operator sequence(s) and the minimal promoter.

In another embodiment, tet operator sequences can be inserted elsewhere within an endogenous gene, preferably within a 5'or 3' regulatory region, via homologous recombination to create an endogenous gene whose expression can be regulated by a tetracycline-regulated fusion protein described herein. For example, one or more tetO sequences can be inserted into a promoter or enhancer region of an endogenous gene such that promoter or enhancer function is maintained (i.e., the tetO sequences are introduced into a site of the promoter/enhancer region that is not critical for promoter/enhancer function). Regions within promoters or enhancers which can be altered without loss of promoter/enhancer function are known in the art for many genes or can be determined by standard techniques for analyzing critical regulatory regions. An endogenous gene having tetO sequences inserted into a non-critical regulatory region will retain the ability to be expressed in its normal constitutive and/or tissue-specific manner but, additionally, can be downregulated by a tetracycline-controlled transcriptional inhibitor protein in a controlled manner. For example, constitutive expression of such a modified endogenous gene can be inhibited by in the presence of tetracycline (or analogue) using an inhibitor fusion protein that binds to tetO sequences in the presence of tetracycline (or analogue) (as described in further detail in Section IV and Section VI, Part B, below).

A. Regulation of Expression of tet Operator-Linked Nucleotide Sequences

Expression of a tet operator-linked nucleotide sequences is regulated by a transactivator fusion protein of the invention. Thus, the fusion protein and the target nucleic acid are both present in a host cell or organism. The presence of both the transactivator fusion protein and the target transcription unit in the same host cell or organism can be achieved in a number of different ways. For example, a host cell can be transfected with one nucleic acid of the expression system (e.g., encoding the transactivator fusion protein), stably transfected cells can be selected and then the transfected cells can be re-transfected (also referred to as "supertransfected") with nucleic acid corresponding to the other nucleic acid of the expression system (e.g., the target nucleic acid to be transcribed). Two distinct selectable markers can be used for selection, e.g., uptake of the first nucleic acid can be selected with G418 and uptake of the second nucleic acid can be selected with hygromycin. Alternatively, a single population of cells can be transfected with nucleic acid corresponding to both components of the system. Accordingly, the invention provides a nucleic acid composition comprising:

a first nucleic acid encoding a fusion protein which activates transcription, the fusion protein comprising a first polypeptide which binds to a tet operator sequence in the presence of tetracycline or a tetracycline analogue operatively linked to a second polypeptide which activates transcription in eukaryotic cells; and a second nucleic acid comprising a nucleotide sequence to be transcribed operatively linked to at least one tet operator sequence.

In one embodiment, the two nucleic acids are two separate molecules (e.g., two different vectors). In this case, a host cell is cotransfected with the two nucleic acid molecules or successively transfected first with one nucleic acid molecule and then the other nucleic acid molecule. In another embodiment, the two nucleic acids are linked (i.e., colinear) in the same molecule (e.g., a single vector). In this case, a host cell is transfected with the single nucleic acid molecule.

The host cell may be a cell cultured in vitro or a cell present in vivo (e.g., a cell targeted for gene therapy). The host cell can further be a fertilized oocyte, embryonic stem cell or any other embryonic cell used in the creation of non-human transgenic or homologous recombinant animals. Transgenic or homologous recombinant animals which comprise both nucleic acid components of the expression system can be created by introducing both nucleic acids into the same cells at an embryonic stage, or more preferably, an animal which carries one nucleic acid component of the system in its genome is mated to an animal which carries the other nucleic acid component of the system in its genome. Offspring which have inherited both nucleic acid components can then be identified by standard techniques.

B. Coordinate Regulation of Expression of Two Nucleotide Sequences

In addition to providing a system for the regulated expression of a single transcribed nucleotide sequence, the invention further permits coordinated regulation of the expression of two nucleotide sequences operatively linked to the same tet operator sequence(s). Accordingly, another aspect of the invention pertains to a novel tet-regulated transcription unit for coordinate regulation of two genes. In this transcription unit, the same tet operator sequence(s) regulates the expression of two operatively linked nucleotide sequences that are transcribed in opposite directions from the common tet operator sequence(s). Accordingly, one nucleotide sequence is operatively linked to one side of the tet operator sequence (e.g., the 5' end on the top strand of DNA) and the other nucleotide sequence is operatively linked to the opposite side of the tet operator sequence (e.g., the 3' end on the top strand of DNA). Additionally, it should be understood that each nucleotide sequence to be transcribed includes an operatively linked minimal promoter sequence which is located between the nucleotide sequence to be transcribed and the tet operator sequence(s).

Figure 6:
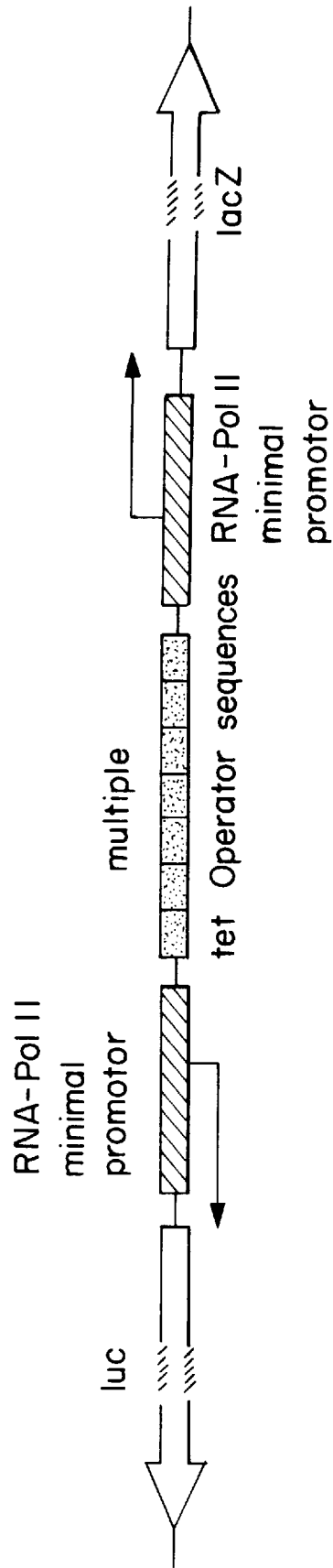
FIG. 6 is a schematic diagram of a bidirectional promoter construct for coordinate regulation of two genes of interest operatively linked to the same tet operators for regulation by a tetracycline-regulated transcriptional activator.

A representative example of such a transcription unit is diagrammed schematically in FIG. 6. In this vectors, the two nucleotide sequences, operatively linked to the same tet operator sequence(s), are transcribed in opposite directions relative to the tet operator sequence(s) (i.e., the sequences are transcribed in a divergent manner upon activation by a transactivator fusion protein of the invention). By "transcribed in opposite directions relative to the tet operator sequence(s)", it is meant that the first nucleotide sequence is transcribed 5' to 3' from one strand of the DNA (e.g., the bottom strand) and the second nucleotide sequence is transcribed 5' to 3' from the other stand of the DNA (e.g., the top strand), resulting in bidirectional transcription away from the tet operator sequence(s).

Accordingly, the invention provides a recombinant vector for coordinately-regulated, bidirectional transcription of two nucleotide sequence. In one embodiment, the vector comprises a nucleotide sequence linked by phosphodiester bonds comprising, in a 5' to 3' direction:

a first nucleotide sequence to be transcribed, operatively linked to at least one tet operator sequence, operatively linked to a second nucleotide sequence to be transcribed, wherein transcription of the first and second nucleotide sequences proceeds in opposite directions from the at least one tet operator sequence(s) (i.e., the first and second nucleotide sequences are transcribed in a divergent manner).

In another embodiment, the vector does not include the first and second nucleotide sequence to be transcribed but instead contains cloning sites which allow for the introduction into the vector of nucleotide sequences of interest. Accordingly, in this embodiment, the vector comprises a nucleotide sequence comprising in a 5' to 3' direction:

a first cloning site for introduction of a first nucleotide sequence to be transcribed, operatively linked to at least one tet operator sequence, operatively linked to a second cloning site for introduction of a second nucleotide sequence to be transcribed, wherein transcription of a first and second nucleotide sequence introduced into the vector proceeds in opposite directions from the at least one tet operator sequence(s). It will be appreciated by those skilled in the art that this type of "cloning vector" may be in a form which also includes minimal promoter sequences such that a first nucleotide sequence introduced into the first cloning site is operatively linked to a first minimal promoter and a second nucleotide sequence introduced into the second cloning site is operatively linked to a second minimal promoter. Alternatively, the "cloning vector" may be in a form which does not include minimal promoter sequences and instead, nucleotide sequences including linked minimal promoter sequences are introduced into the cloning sites of the vector.

The term "cloning site" is intended to encompass at least one restriction endonuclease site. Typically, multiple different restriction endonuclease sites (e.g., a polylinker) are contained within the nucleic acid.

In yet another embodiment, the vector for coordinate, bidirectional transcription of two nucleotide sequences may contain a first nucleotide to be transcribed, such as that encoding a detectable marker (e.g., luciferase or β-galactosidase), and a cloning site for introduction of a second nucleotide sequence of interest.

Figure 7B:
FIG. 7B (SEQ ID NO: 7) shows the nucleotide sequence of a bidirectional promoter region for coordinate regulation of two genes of interest by a tetracycline-regulated transcriptional activator.

The nucleotide sequences of two different suitable bidirectional promoter regions for use in a vector for coordinate regulation of two nucleotide sequences to be transcribed, as described herein, are shown in FIGS. 7A and 7B (SEQ ID NOS: 6 and 7, respectively). In the construct of FIG. 7A, both minimal promoters present in the construct are derived from a CMV promoter. In the construct of FIG. 7B, one minimal promoter present in the construct is derived from a CMV promoter, whereas the second minimal promoter is derived from a TK promoter. A plasmid pUHDG1316-8, comprising a bidirectional promoter of the invention, has been deposited on Jul. 8, 1994 under the provisions of the Budapest Treaty at the Deutsche Sammlung Von Mikroorganismen und ZellKulturen GmbH (DSM) in Braunschweig, Germany and assigned deposit number DSM 9281.

The transcription unit of the invention for bidirectional transcription of two nucleotide sequences operatively linked to the same tet operator sequence(s) is useful for coordinating the expression of the two nucleotide sequences of interest. Preferably, at least one of the nucleotide sequences to be transcribed is a eukaryotic nucleotide sequence. In one application, the vector is used to produce stoichiometric amounts of two subunits of a heterodimeric molecule in the same cell. For example, the vector can be used produce antibody heavy and light chains in the same cell or to produce growth factor receptor subunits in the same cells. In another application, the vector is used to express two gene products that cooperate in establishing a particular cellular phenotype. In yet another application, the vector is used to coexpress an indicator function and a gene of interest, wherein the indicator is utilized to monitor expression of the gene of interest. Thus, one of the two coordinately expressed sequences can encode a gene of interest and the other can encode a detectable marker, such as a surface marker or enzyme (e.g., β-galactosidase or luciferase) which is used for selection of cells expressing the gene of interest.

Transcription of the two coordinately-regulated nucleotide sequences can be induced by tetracycline (or an analogue thereof) by use of the Tc-inducible transcriptional activator of the invention to regulate expression of the two nucleotide sequences. Thus, in this system, expression of both nucleotide sequences is "off" in the absence of Tc (or analogue), whereas expression is turned "on" by the presence of Tc (or analogue). Alternatively, the vector for coordinate regulation of two nucleotide sequences can be used in conjunction with other tetracycline-regulated transcription factors known in the art. For example, a transactivator fusion protein of a wild-type Tet repressor fused to a transcriptional activation domain, which activates gene expression in the absence of Tc (or analogue), such as the tTA described in Gossen, M. and Bujard, H. (1992) *Proc. Natl. Acad. Sci. USA* 89:5547–5551, can also be used in conjunction with this target transcription unit for coordinate regulation.

C. Independent Regulation of Expression of Multiple Nucleotide Sequences

The invention still further permits independent and opposite regulation of two or more nucleotide sequences to be transcribed. Accordingly, another aspect of the invention pertains to a novel tet-regulated transcription unit for independent regulation of two or more genes. To independently regulate the expression of two nucleotide sequences to be transcribed, one nucleotide sequence is operatively linked to a tet operator sequence(s) of one class type and the other nucleotide sequence is operatively linked to a tet operator sequence(s) of another class type. Accordingly, the invention provides at least one recombinant vector for independent regulation of transcription of two nucleotide sequences. In one embodiment, the vector(s) comprises:

a first nucleotide sequence to be a transcribed operatively linked to at least one tet operator sequence of a first class type; and a second nucleotide sequence to be a transcribed operatively linked to at least one tet operator sequence of a second class type. (It should be understood that each nucleotide sequence to be transcribed also includes an operatively linked, upstream minimal promoter sequence.) The two independently regulated transcription units can be included on a single vector, or alternatively, on two separate vectors. The recombinant vector(s) containing the nucleotide sequences to be transcribed can be introduced into a host cell or animal as described previously.

In another embodiment, the vector(s) does not include the first and second nucleotide sequence to be transcribed but instead contains cloning sites which allow for the introduction into the vector of nucleotide sequences of interest. Accordingly, in this embodiment, the vector(s) comprises:

- a first cloning site for introduction of a first nucleotide sequence to be transcribed operatively linked to at least one tet operator sequence of a first class type; and
- a second cloning site for introduction of a second nucleotide sequence to be transcribed operatively linked to at least one tet operator sequence of a second class type.

This cloning vector(s) may be in a form that already includes first and second minimal promoters operatively linked, respectively, to the first and second cloning sites. Alternatively, nucleotide sequences to be transcribed which include an operatively linked minimal promoter can be introduced into the cloning vector.

In yet another embodiment, the vector for independent regulation of two nucleotide sequences may contain a first nucleotide to be transcribed, such as that encoding a detectable marker or a suicide gene, operatively linked to at least one tet operator sequence of a first class type and a cloning site for introduction of a second nucleotide sequence of interest such that it is operatively linked to at least one tet operator sequence of a second class type.

It will be appreciated by those skilled in the art that various combinations of classes of tet operator sequences can be used for independent regulation of two nucleotide sequences. For example, the first tet operator sequence(s) can be of the class A type and the second can be of the class B type, or the first tet operator sequence can be of the class B type and the second can be of the class C type, etc. Preferably, one to the two tet operators used is a class B type operator.

Independent transcription of the first and second nucleotide sequences is regulated in a host cell by further introducing into the host cell one or more nucleic acids encoding two different transactivator fusion proteins which bind independently to tet operator sequences of different class types. The first fusion protein comprises a polypeptide which binds to a tet operator sequence in the presence of tetracycline or a tetracycline analogue, operatively linked to a polypeptide which activates transcription in eukaryotic cells (e.g., a transactivator fusion protein of the invention, such as a mutated Tn10-derived Tet repressor linked to a VP16 activation region). The second fusion protein comprises a polypeptide which binds to a tet operator sequence in the absence of tetracycline or a tetracycline analogue, operatively linked to a polypeptide which activates transcription in eukaryotic cells (e.g., a wild-type Tn10-derived Tet repressor linked to a VP16 activation region, such as the tTA described in Gossen, M. and Bujard, H. (1992) *Proc. Natl. Acad. Sci. USA* 89:5547–5551). In one embodiment, the first fusion protein binds to the tet operator sequence of the first class type used in the transcription unit and the second fusion protein binds to the tet operator sequence of the second class type used in the transcription unit. Alternatively, in another embodiment, the first fusion protein binds to the second class type of tet operator and the second fusion protein binds to the first class type of tet operator.

For example, the first nucleotide sequence to be transcribed may be linked to a class A tet operator and the first fusion protein may bind to class A operators, whereas the second nucleotide sequence to be transcribed may be linked to a class B tet operator and the second fusion protein may bind to class B operators. Thus, in this embodiment, transcription of the first nucleotide sequence is activated in the presence of Tc (or analogue thereof) while transcription of the second nucleotide sequence is activated in the absence of Tc (or analogue thereof). Alternatively, in another embodiment, the first fusion protein binds to class B operators and the second fusion protein binds to class A operators. In this case, transcription of the second nucleotide sequence is activated in the presence of Tc (or analogue thereof) while transcription of the first nucleotide sequence is activated in the absence of Tc (or analogue thereof). Appropriate transactivator proteins for use in this system can be designed as described above in Section I and in Gossen and Bujard (1992) cited supra. In order to inhibit heterodimerization between the two different types of Tet repressor fusion proteins present in the same cell, it may be necessary to mutate the dimerization region of one or both of the transactivator fusion proteins. Mutations can be targeted to the C-terminal region of TetR known to be involved in dimerization. The dimerization region has been described in detail based upon the crystal structure of TetR (see Hinrichs, W. et al. (1994) *Science* 264:418–420).

This system allows for independent and opposite regulation of the expression of two genes by Tc and analogues thereof. Use of different Tc analogues as inducing agents may further allow for high, low or intermediate levels of expression of the different sequences (discussed in greater detail in Section V below). The novel transcription unit of the invention for independently regulating the expression of two genes, described above, can be used in situations where two gene products are to be expressed in the same cell but where it is desirable to express one gene product while expression of the other gene product is turned "off", and vice versa. For example, this system is particularly useful for expressing in the same host cell either a therapeutic gene or a suicide gene (i.e., a gene which encodes a product that can be used to destroy the cell, such as ricin or herpes simplex virus thymidine kinase). In many gene therapy situations, it is desirable to be able to express a gene for therapeutic purposes in a host cell but also to have the capacity to destroy the host cell once the therapy is completed. This can be accomplished using the above-described system by linking the therapeutic gene to one class of tet operator and the suicide gene to another class of tet operator. Thus, expression of the therapeutic gene in a host cell can be stimulated by Tc (in which case expression of the suicide gene is absent). Then, once the therapy is complete, Tc is removed, which turns off expression of the therapeutic gene and turns on expression of the suicide gene in the cell.

D. Combined Coordinate and Independent Regulation of Multiple Nucleotide Sequences It is further possible to regulate the expression of four nucleotide sequences by combining the system described in Section IIIB with the system described in Section IIIC such that two pairs of sequences are coordinately regulated while one pair is independently regulated from the other pair. Accordingly, two target transcription units can be designed comprising:

a first nucleic acid comprising in a 5' to 3' direction: a first nucleotide sequence to be transcribed, a tet operator sequence(s) of a first class type, and a second nucleotide sequence to be transcribed a second nucleic acid comprising in a 5' to 3' direction: a third nucleotide sequence to be transcribed, a tet operator sequence(s) of a second class type, and a fourth nucleotide sequence to be transcribed.

Transcription of the first and second nucleotide sequences in the first nucleic acid proceeds in a divergent manner from the first class of tet operator sequence(s). Likewise, transcription of the third and fourth nucleotide sequences in the second nucleic acid proceeds in a divergent manner from the second class of tet operator sequence(s). Thus, expression of the first and second nucleotide sequences is coordinately regulated and expression of the third and fourth nucleotide sequences is coordinately regulated. However, expression of the first and second sequences is independently (and oppositely) regulated compared to the third and fourth sequences through the use of two different transactivator fusion proteins, as described above, one which activates transcription in the presence of Tc (or analogue thereof) and the other which activates transcription in the absence of Tc (or analogue thereof). One transactivator is designed to bind to a tet operators of the first class type and the other is designed to bind to a tet operators of the second class type. In other embodiments, rather than already containing first, second, third and/or fourth nucleotide sequences to be transcribed, these transcription units can contain cloning sites which allow for the introduction of first, second, third and/or fourth nucleotide sequences to be transcribed.

IV. Tetracycline-Regulated Transcriptional Inhibitors

Another aspect of the invention pertains to transcriptional inhibitor fusion proteins. The inhibitor fusion proteins of the invention are constructed similarly to the transactivator fusion proteins of the invention (see Section I above) but instead of containing a polypeptide domain that stimulates transcription in eukaryotic cells, the inhibitor fusion proteins contain a polypeptide domain that inhibits transcription in eukaryotic cells. The inhibitor fusion proteins are used to downregulate the expression of genes operably linked to tetO sequences. For example, when a tetO-linked gene is introduced into a host cell or animal, the level of basal, constitutive expression of the gene may vary depending upon the type of cell or tissue in which the gene is introduced and on the site of integration of the gene. Alternatively, constitutive expression of endogenous genes into which tetO sequences have been introduced may vary depending upon the strength of additional endogenous regulatory sequences in the vicinity. The inhibitor fusion proteins described herein provide compositions that can be used to inhibit the expression of such tetO-linked genes in a controlled manner.

In one embodiment, the inhibitor fusion protein of the invention comprises a first polypeptide that binds to tet operator sequences in the absence, but not the presence, of tetracycline (Tc) or an analogue thereof operatively linked to a heterologous second polypeptide that inhibits transcription in eukaryotic cells. In another embodiment, the inhibitor fusion protein comprises a first polypeptide that binds to tet operator sequences in the presence, but not the absence, of tetracycline operatively linked to a heterologous second polypeptide that inhibits transcription in eukaryotic cells. The term "heterologous" is intended to mean that the second polypeptide is derived from a different protein than the first polypeptide. Like the transactivator fusion proteins, the transcriptional inhibitor fusion proteins can be prepared using standard recombinant DNA techniques as described herein.

A. The First Polypeptide of the Transcriptional Inhibitor Fusion Protein

The transcriptional inhibitor fusion protein of the invention is composed, in part, of a first polypeptide which binds to a tet operator sequence either (i) in the absence, but not the presence of tetracycline (Tc), or an analogue thereof, or alternatively, (ii) in the presence, but not the absence of Tc or an analogue thereof.

Preferably, in the former embodiment, the first polypeptide is a wild-type Tet repressor (which binds to tet operator sequences in the absence but not the presence of Tc). A wild-type Tet repressor of any class (e.g., A, B, C, D or E) may be used as the first polypeptide. Preferably, the wild-type Tet repressor is a Tn10-derived Tet repressor. The nucleotide and amino acid sequences of a wild-type Tn10-derived Tet repressor are shown in SEQ ID NO: 16 and SEQ ID NO: 17, respectively.

Alternatively, in the latter embodiment, the first polypeptide is a mutated Tet repressor as described in Section I, part A above (which binds to tet operator sequences in the presence but not the absence of Tc). A mutated Tet repressor of any class (e.g., A, B, C, D or E) may be used as the first polypeptide. Preferably, the mutated Tet repressor is a Tn10-derived Tet repressor having one or more amino acid substitutions at positions 71, 95, 101 and/or 102. The nucleotide and amino acid sequences of such a mutated Tn10-derived Tet repressor are shown in SEQ ID NO: 18 and SEQ ID NO: 19, respectively.

B. The Second Polypeptide of the Transcriptional Inhibitor Fusion Protein

The first polypeptide of the transcriptional inhibitor fusion protein is operatively linked to a second polypeptide which directly or indirectly inhibits transcription in eukaryotic cells. As described in Section I, above, to operatively link the first and second polypeptides of a fusion protein, typically nucleotide sequences encoding the first and second polypeptides are ligated to each other in-frame to create a chimeric gene encoding the fusion protein. However, the first and second polypeptides can be operatively linked by other means that preserve the function of each polypeptide (e.g., chemically crosslinked). Although the fusion proteins are typically described herein as having the first polypeptide at the amino-terminal end of the fusion protein and the second polypeptide at the carboxy-terminal end of the fusion protein, it will be appreciated by those skilled in the art that the opposite orientation (i.e., the second polypeptide at the amino-terminal end and the first polypeptide at the carboxy-terminal end) is also contemplated by the invention.

Proteins and polypeptide domains within proteins which can function to inhibit transcription in eukaryotic cells have been described in the art (for reviews see, e.g., Renkawitz, R. (1990) *Trends in Genetics* 6:192–197; and Herschbach, B. M. and Johnson, A. D. (1993) *Annu. Rev. Cell. Biol.* 9:479–509). Such transcriptional inhibitor domains have been referred to in the art as "silencing domains" or "repressor domains." Although the precise mechanism by which many of these polypeptide domains inhibit transcription is not known (and the invention is not intended to be limited by mechanism), there are several possible means by which repressor domains may inhibit transcription, including: 1) competitive inhibition of binding of either activator proteins or the general transcriptional machinery, 2) prevention of the activity of a DNA bound activator and 3) negative interference with the assembly of a functional preinitiation complex of the general transcription machinery. Thus, a repressor domain may have a direct inhibitory effect on the transcriptional machinery or may inhibit transcription indirectly by inhibiting the activity of activator proteins. Accordingly, the term "a polypeptide that inhibits transcription in eukaryotic cells" as used herein is intended to include polypeptides which act either directly or indirectly to inhibit transcription. As used herein, "inhibition" of transcription is intended to mean a diminution in the level or amount of transcription of a target gene compared to the level or amount of transcription prior to regulation by the transcriptional inhibitor protein. Transcriptional inhibition may be partial or complete. The terms "silencer", "repressor" and "inhibitor" are used interchangeably herein to describe a regulatory protein, or domains thereof, that can inhibit transcription.

A transcriptional "repressor" or "silencer" domain as described herein is a polypeptide domain that retains its transcriptional repressor function when the domain is transferred to a heterologous protein. Proteins which have been demonstrated to have repressor domains that can function when transferred to a heterologous protein include the v-erbA oncogene product (Baniahmad, A. et al. (1992) *EMBO J.* 11:1015–1023), the thyroid hormone receptor (Baniahmad, supra), the retinoic acid receptor (Baniahmad, supra), and the Drosophila Krueppel (Kr) protein (Licht, J. D. et al. (1990) *Nature* 346:76–79; Sauer, F. and Jäckle, H. (1991) *Nature* 353:563–566; Licht, J. D. et al. (1994) *Mol. Cell. Biol.* 14:4057–4066). Non-limiting examples of other proteins which have transcriptional repressor activity in eukaryotic cells include the Drosophila homeodomain protein even-skipped (eve), the *S. cerevisiae* Ssn6/Tup1 protein complex (see Herschbach and Johnson, supra), the yeast SIR1 protein (see Chien, et al. (1993) *Cell* 75:531–541), NeP1 (see Kohne, et al. (1993) *J. Mol. Biol.* 232:747–755), the Drosophila dorsal protein (see Kirov, et al. (1994) *Mol. Cell. Biol.* 14:713–722; Jiang, et al. (1993) *EMBO J.* 12:3201–3209), TSF3 (see Chen, et al. (1993) *Mol. Cell. Biol.* 13:831–840), SF1 (see Targa, et al. (1992) *Biochem. Biophys. Res. Comm.* 188:416–423), the Drosophila hunchback protein (see Zhang, et al. (1992) *Proc. Natl. Acad. Sci. USA* 89:7511–7515), the Drosophila knirps protein (see Gerwin, et al. (1994) *Mol. Cell. Biol.* 14:7899–7908), the WT1 protein (Wilm's tumor gene product) (see Anant, et al. (1994) *Oncogene* 9:3113–3126; Madden et al., (1993) *Oncogene* 8:1713–1720), Oct-2.1 (see Lillycrop, et al. (1994) *Mol. Cell. Biol.* 14:7633–7642), the Drosophila engrailed protein (see Badiani, et al. (1994) *Genes Dev.* 8:770–782; Han and Manley, (1993) *EMBO J.* 12:2723–2733), E4BP4 (see Cowell and Hurst, (1994) *Nucleic Acids Res.* 22:59–65) and ZF5 (see Numoto, et al. (1993) *Nucleic Acids Res.* 21:3767–3775), In a preferred embodiment, the second polypeptide of the transcriptional inhibitor fusion protein of the invention is a transcriptional silencer domain of the Drosophila Krueppel protein. A C-terminal region having repressor activity can be used, such as amino acids 403–466 of the native protein (see Sauer, F. and Jäckle, H., supra). This region is referred to as C64KR. The nucleotide and amino acid sequences of C64KR are shown in SEQ ID NO: 20 and SEQ ID NO: 21, respectively. Construction of an expression vector encoding a TetR-C64KR fusion protein is described in Example 4. Alternatively, an alanine-rich amino terminal region of Kr that also has repressor activity can be used as the second polypeptide of the fusion protein. For example, amino acids 26–110 of Kr (see Licht, J. D. et al., (1990) supra) can be used as the second polypeptide. Alternatively, shorter or longer polypeptide fragments encompassing either of the Kr silencer domains that still retain full or partial inhibitor activity are also contemplated (e.g., amino acids 62 to 92 of the N-terminal silencer domain; see Licht, et al. (1994) supra).

In another preferred embodiment, the second polypeptide of the transcriptional inhibitor fusion protein of the invention is a transcriptional silencer domain of the v-erbA oncogene product. The silencer domain of v-erbA has been mapped to approximately amino acid residues 362–632 of the native v-erbA oncogene product (see Baniahmad, et al. supra). Accordingly, a fragment encompassing this region is used as the second polypeptide of the silencer domain. In one embodiment, amino acid residues 364–635 of the native v-erbA protein are used. The nucleotide and amino acid sequences of this region of v-erbA are shown in SEQ ID NO: 22 and SEQ ID NO: 23, respectively. Construction of an expression vector encoding a TetR-v-erbA fusion protein is described in Example 5. Alternatively, shorter or longer polypeptide fragments encompassing the v-erbA silencer region that still retain full or partial inhibitor activity are also contemplated. For example, a.a. residues 346–639, 362–639, 346–632, 346–616 and 362–616 of v-erbA may be used. Additionally, polypeptide fragments encompassing these regions that have internal deletions yet still retain full or partial inhibitor activity are encompassed by the invention, such as a.a. residues 362–468/508–639 of v-erbA. Furthermore, two or more copies of the silencer domain may be included in the fusion protein, such as two copies of a.a. residues 362–616 of v-erbA. Suitable silencer polypeptide domains of v-erbA are described further in Baniahmad, A. et al. (supra).

In other embodiments, other silencer domains are used. Non-limiting examples of polypeptide domains that can be used include: amino acid residues 120–410 of the thyroid hormone receptor alpha (THRα), amino acid residues 143–403 of the retinoic acid receptor alpha (RARα), amino acid residues 186–232 of knirps, the N-terminal region of WT 1 (see Anant, supra), the N-terminal region of Oct-2.1 (see Lillycrop, supra), a 65 amino acid domain of E4BP4 (see Cowell and Hurst, supra) and the N-terminal zinc finger domain of ZF5 (see Numoto, supra). Moreover, shorter or longer polypeptide fragments encompassing these regions that still retain full or partial inhibitor activity are also contemplated.

In addition to previously described transcriptional inhibitor domains, novel transcriptional inhibitor domains, which can be identified by standard techniques, are within the scope of the invention. The transcriptional inhibitor ability of a polypeptide can be assayed by: 1) constructing an expression vector that encodes the test silencer polypeptide linked to another polypeptide having DNA binding activity (i.e., constructing a DNA binding domain-silencer domain fusion protein), 2) cotransfecting this expression vector into host cells together with a reporter gene construct that is normally constitutively expressed in the host cell and also contains binding sites for the DNA binding domain and 3) determining the amount of transcription of the reporter gene construct that is inhibited by expression of the fusion protein in the host cell. For example, a standard assay used in the art utilizes a fusion protein of a GAL4 DNA binding domain (e.g., amino acid residues 1 147) and a test silencer domain. This fusion protein is then used to inhibit expression of a reporter gene construct that contains positive regulatory sequences (that normally stimulate constitutive transcription) and GAL4 binding sites (see e.g., Baniahmad, supra).

C. A Third Polypeptide of the Transcriptional Inhibitor Fusion Protein

In addition to a Tet repressor and a transcriptional silencer domain, a transcriptional inhibitor fusion protein of the invention can contain an operatively linked third polypeptide which promotes transport of the fusion protein to a cell nucleus. As described for the transactivator fusion proteins (see Section I, Part C, above), a nuclear localization signal can be incorporated into the transcriptional inhibitor fusion protein.

D. Expression of the Transcriptional Inhibitor Fusion Protein

A nucleic acid molecule encoding a transcriptional inhibitor fusion protein of the invention can be incorporated into a recombinant expression vector and introduced into a host cell to express the fusion protein in the host cell as described in Section II, Parts A, B and C, above. Preferably, a host cell expressing a transcriptional inhibitor fusion protein of the invention also carries a tet operator-linked gene of interest (i.e., target nucleotide sequence to be transcribed).

Transgenic organisms expressing a transcriptional inhibitor fusion protein in cells thereof can be prepared as described in Section II, Part D, above. Moreover, homologous recombinant organisms expressing a transcriptional inhibitor fusion protein in cells thereof are also encompassed by the invention and can be prepared as described in Section II, Part E, above. The invention provides recombinant expression vectors suitable for homologous recombination. In one embodiment, such an expression vector comprises a nucleic acid molecule encoding a transcriptional inhibitor fusion protein of the invention which is flanked at its 5' and 3' ends by additional nucleic acid of a eukaryotic gene, the additional nucleic acid being of sufficient length for successful homologous recombination with the eukaryotic gene. Vectors and methods for creating homologous recombinant organisms that express the components of the regulatory system of the invention, and uses therefor, are described in further detail in U.S. Pat. No. 5,650,298. Preferably, a transgenic or homologous recombinant organism of the invention expressing a transcriptional inhibitor fusion protein in cells thereof also carries a tet operator-linked gene of interest (i.e., target nucleotide sequence to be transcribed) in cells thereof.

V. Kits of the Invention

Another aspect of the invention pertains to kits which include the components of the inducible regulatory system of the invention. Such a kit can be used to regulate the expression of a gene of interest (i.e., a nucleotide sequence of interest to be transcribed) which can be cloned into a target transcription unit. The kit may include nucleic acid encoding a transcriptional activator fusion protein or a transcriptional inhibitor fusion protein or both. Alternatively, eukaryotic cells which have nucleic acid encoding a transactivator and/or inhibitor fusion protein stably incorporated therein, such that the transactivator and/or inhibitor fusion protein are expressed in the eukaryotic cell, may be provided in the kit.

In one embodiment, the kit includes a carrier means having in close confinement therein at least two container means: a first container means which contains a first nucleic acid (e.g., DNA) encoding a transactivator fusion protein of the invention (e.g., a recombinant expression vector encoding a first polypeptide which binds to a tet operator sequence in the presence of tetracycline operatively linked to a second polypeptide which activates transcription in eukaryotic cells), and a second container means which contains a second target nucleic acid (e.g., DNA) for the transactivator into which a nucleotide sequence of interest can be cloned. The second nucleic acid typically comprises a cloning site for introduction of a nucleotide sequence to be transcribed (optionally including an operatively linked minimal promoter sequence) and at least one operatively linked tet operator sequence. The term "cloning site" is intended to encompass at least one restriction endonuclease site. Typically, multiple different restriction endonuclease sites (e.g., a polylinker) are contained within the nucleic acid.

To regulate expression of a nucleotide sequence of interest using the components of the kit, the nucleotide sequence is cloned into the cloning site of the target vector of the kit by conventional recombinant DNA techniques and then the first and second nucleic acids are introduced into a host cell or animal. The transactivator fusion protein expressed in the host cell or animal then regulates transcription of the nucleotide sequence of interest in the presence of the inducing agent (Tc or analogue thereof).

Alternatively, in another embodiment, the kit includes a eukaryotic cell which is stably transfected with a nucleic acid encoding a transactivator fusion protein of the invention such that the transactivator is expressed in the cell. Thus, rather than containing nucleic acid alone, the first container means described above can contain a eukaryotic cell line into which the first nucleic acid encoding the transactivator has been stably introduced (e.g., by stable transfection by a conventional method such as calcium phosphate precipitation or electroporation, etc.). In this embodiment, a nucleotide sequence of interest is cloned into the cloning site of the target vector of the kit and then the target vector is introduced into the eukaryotic cell expressing the transactivator fusion protein.

Alternatively or additionally, a recombinant vector of the invention for coordinate regulation of expression of two nucleotide sequences can also be incorporated into a kit of the invention. The vector can be included in the kit in a form that allows for introduction into the vector of two nucleotide sequences of interest. Thus, in another embodiment, a kit of the invention includes 1) a first nucleic acid encoding a transactivator fusion protein of the invention (or a eukaryotic cell into which the nucleic acid has been stably introduced) and 2) a second nucleic acid comprising a nucleotide sequence comprising in a 5' to 3' direction: a first cloning site for introduction of a first nucleotide sequence of interest operatively linked to at least one tet operator sequence operatively linked to a second cloning site for introduction of a second nucleotide sequence of interest, wherein transcription of the first and second nucleotide sequences proceeds in opposite directions from the at least one tet operator sequence. Optionally, the vector can include operatively linked minimal promoter sequences. In another embodiment, the vector can be in a form that already contains one nucleotide sequence to be transcribed (e.g., encoding a detectable marker such as luciferase, β-galactosidase or CAT) and a cloning site for introduction of a second nucleotide sequence of interest to be transcribed.

The transcription units and transactivators of the invention for independent regulation of expression of two nucleotide sequences to be transcribed can also be incorporated into a kit of the invention. The target transcription units can be in a form which allows for introduction into the transcription units of nucleotide sequences of interest to be transcribed. Thus, in another embodiment, a kit of the invention includes 1) a first nucleic acid encoding a transactivator which binds to a tet operator of a first class type in the presence of Tc or an analogue thereof, 2) a second nucleic acid comprising a first cloning site for introduction of a first nucleotide sequence to be transcribed operatively linked to at least one tet operator of a first class type, 3) a third nucleic acid encoding a transactivator which binds to a tet operator of a second class type in the absence of Tc or an analogue thereof, and 4) a fourth nucleic acid comprising a second cloning site for introduction of a second nucleotide sequence to be transcribed operatively linked to at least one tet operator of a second class type. (Optionally, minimal promoter sequences are included in the second and fourth nucleic acids). In another embodiment, one nucleotide sequence to be transcribed (e.g., encoding a suicide gene) is already contained in either the second or the fourth nucleic acid. In yet another embodiment, the nucleic acids encoding the transactivators (e.g., the first and third nucleic acids described above) can be stably introduced into a eukaryotic cell line which is provided in the kit.

In yet another embodiment, a kit of the invention includes a first container means containing a first nucleic acid encoding a transcriptional inhibitor fusion protein of the invention (e.g., the fusion protein inhibits transcription in eukaryotic cells either only in the presence of Tc or only the absence of Tc) and a second container means containing a second nucleic acid comprising a cloning site for introduction of a nucleotide sequence to be transcribed operatively linked to at least one tet operator sequence. The kit may further include a third nucleic acid encoding a transactivator fusion protein that binds to tetO sequences either only in the presence of Tc or only in the absence of Tc. Alternatively, the first and/or third nucleic acids (i.e., encoding the inhibitor or transactivator fusion proteins) may be stably incorporated into a eukaryotic host cell which is provided in the kit.

In still another embodiment, a kit of the invention may include at least one tetracycline or tetracycline analogue. For example, the kit may include a container means which contains tetracycline, anhydrotetracycline, doxycycline, epioxytetracycline or other tetracycline analogue described herein.

VI. Regulation of Gene Expression by Tetracycline or Analogues Thereof

A. Stimulation of Gene Expression by Transactivator Fusion Proteins

In a host cell which carries nucleic acid encoding a transactivator fusion protein of the invention and a nucleotide sequence operatively linked to the tet operator sequence(i.e., gene of interest to be transcribed), high level transcription of the nucleotide sequence operatively linked to the tet operator sequence(s) does not occur in the absence of the inducing agent, tetracycline or analogues thereof The level of basal transcription of the nucleotide sequence may vary depending upon the host cell and site of integration of the sequence, but is generally quite low or even undetectable in the absence of Tc. In order to induce transcription in a host cell, the host cell is contacted with tetracycline or a tetracycline analogue. Accordingly, another aspect of the invention pertains to methods for stimulating transcription of a nucleotide sequence operatively linked to a tet operator sequence in a host cell or animal which expresses a transactivator fusion protein of the invention. The methods involve contacting the cell with tetracycline or a tetracycline analogue or administering tetracycline or a tetracycline analogue to a subject containing the cell.

The term "tetracycline analogue" is intended to include compounds which are structurally related to tetracycline and which bind to the Tet repressor with a $K_a$ of at least about $10^6$ $M^{-1}$. Preferably, the tetracycline analogue binds with an affinity of about $10^9$ $M^{-1}$ or greater. Examples of such tetracycline analogues include, but are not limited to, anhydrotetracycline, doxycycline, chlorotetracycline, oxytetracycline and others disclosed by Hlavka and Boothe, "The Tetracyclines," in *Handbook of Experimental Pharmacology* 78, R. K. Blackwood et al. (eds.), Springer-Verlag, Berlin-New York, 1985; L. A. Mitscher, "The Chemistry of the Tetracycline Antibiotics", *Medicinal Research* 9, Dekker, N.Y., 1978; Noyee Development Corporation, "Tetracycline Manufacturing Processes" *Chemical Process Reviews,* Park Ridge, N.J., 2 volumes, 1969; R. C. Evans, "The Technology of the Tetracyclines", *Biochemical Reference Series* 1, Quadrangle Press, New York, 1968; and H. F. Dowling, "Tetracycline", *Antibiotic Monographs,* no. 3, Medical Encyclopedia, New York, 1955. Preferred Tc analogues for high level stimulation of transcription are anhydrotetracycline and doxycycline. A Tc analogue can be chosen which has reduced antibiotic activity compared to Tc. Examples of such Tc analogues are anhydrotetracycline, epioxytetracycline and cyanotetracycline.

To induce gene expression in a cell in vitro, the cell is contacted with Tc or a Tc analogue by culturing the cell in a medium containing the compound. When culturing cells in vitro in the presence of Tc or Tc analogue, a preferred concentration range for the inducing agent is between about 10 and about 1000 ng/ml. Tc or a Tc analogue can be directly added to media in which cells are already being cultured, or more preferably for high levels of gene induction, cells are harvested from Tc-free media and cultured in fresh media containing Tc, or an analogue thereof.

To induce gene expression in vivo, cells within in a subject are contacted with Tc or a Tc analogue by administering the compound to the subject. The term "subject" is intended to include humans and other non-human mammals including monkeys, cows, goats, sheep, dogs, cats, rabbits, rats, mice, and transgenic and homologous recombinant species thereof. Furthermore, the term "subject" is intended to include plants, such as transgenic plants. When the inducing agent is administered to a human or animal subject, the dosage is adjusted to preferably achieve a serum concentration between about 0.05 and 1.0 $\mu$g/ml. Tc or a Tc analogue can be administered to a subject by any means effective for achieving an in vivo concentration sufficient for gene induction. Examples of suitable modes of administration include oral administration (e.g., dissolving the inducing agent in the drinking water), slow release pellets and implantation of a diffusion pump. To administer Tc or a Tc analogue to a transgenic plant, the inducing agent can be dissolved in water administered to the plant.

The ability to use different Tc analogues as inducing agents in this system allows for modulate the level of expression of a tet operator-linked nucleotide sequence. As demonstrated in Example 2, anhydrotetracycline and doxycycline have been found to be strong inducing agents. The increase in transcription of the target sequence is typically as high as 1000- to 2000-fold, and induction factors as high as 20,000 fold can be achieved. Tetracycline, chlorotetracycline and oxytetracycline have been found to be weaker inducing agents, i.e., the increase in transcription of a target sequence is in the range of about 10-fold. Thus, an appropriate tetracycline analogue is chosen as an inducing agent based upon the desired level of induction of gene expression. It is also possible to change the level of gene expression in a host cell or animal over time by changing the Tc analogue used as the inducing agent. For example, there may be situations where it is desirable to have a strong burst of gene expression initially and then have a sustained lower level of gene expression. Accordingly, an analogue which stimulates a high levels of transcription can be used initially as the inducing agent and then the inducing agent can be switched to an analogue which stimulates a lower level of transcription. Moreover, when regulating the expression of multiple nucleotide sequences (e.g., when one sequence is regulated by a one of class tet operator sequence(s) and the other is regulated by another class of tet operator sequence(s), as described above in Section III, Part C, above), it may be possible to independently vary the level of expression of each sequence depending upon which transactivator fusion protein is used to regulate transcription and which Tc analogue(s) is used as the inducing agent. Different transactivator fusion proteins are likely to exhibit different levels of responsiveness to Tc analogues. The level of induction of gene expression by a particular combination of transactivator fusion protein and inducing agent (Tc or Tc analogue) can be determined by techniques described herein, (e.g., see Example 2). Additionally, the level of gene expression can be modulated by varying the concentration of the inducing agent. Thus, the expression system of the invention provides a mechanism not only for turning gene expression on or off, but also for "fine tuning" the level of gene expression at intermediate levels depending upon the type and concentration of inducing agent used.

B. Inhibition of Gene Expression by Transcriptional Inhibitor Fusion Proteins

The invention also provides methods for inhibiting gene expression using the transcriptional inhibitor fusion proteins of the invention. These methods can be used to downregulate basal, constitutive or tissue-specific transcription of a tetO-linked gene of interest. For example, a gene of interest that is operatively linked to tetO sequences and additional positive regulatory elements (e.g., consitutive or tissue-specific enhancer sequences) will be transcribed in host cells at a level that is primarily determined by the strength of the positive regulatory elements in the host cell. Moreover, a gene of interest that is operatively linked to tetOsequences and only a minimal promoter sequence may exhibit varying degrees of basal level transcription depending on the host cell or tissue and/or the site of integration of the sequence. In a host cell containing such a target sequence and expressing an inhibitor fusion protein of the invention, transcription of the target sequence can be down regulated in a controlled manner by altering the concentration of Tc (or analogue) in contact with the host cell. For example, when the inhibitor fusion protein binds to tetO in the absence of Tc, the concentration of Tc in contact with the host cell is reduced to inhibit expression of the target gene. Preferably, a host cell is cultured in the absence of Tc to keep target gene expression repressed. Likewise, Tc is not administered to a host organism to keep target gene expression repressed. Alternatively, when the inhibitor fusion protein binds to tetO in the presence of Tc, the concentration of Tc in contact with the host cell is increased to inhibit expression of the target gene. For example, Tc is added to the culture medium of a host cell or Tc is administered to a host organism to repress target gene expression.

The inhibitor fusion proteins described herein can inhibit a tetO-linked gene of interest in which the tetO sequences are positioned 5' of a minimal promoter sequence (e.g., tetracycline-regulated transcription units as described in Section III, above). Furthermore, the inhibitor fusion protein may be used to inhibit expression of a gene of interest in which tetO-linked sequences are located 3' of the promoter sequence but 5' of the transcription start site. Still further, the inhibitor fusion protein may be used to inhibit expression of a gene of interest in which tetO-linked sequences are located 3' of the transcription start site.

Various Tc analogues as described in Section VI, part A, above, with respect to the transactivator fusion proteins can similarly be used to regulate the activity of the inhibitor fusion proteins. Moreover, the methods of in vitro culture with Tc (or analogue) and in vivo administration of Tc (or analogue) described in Section VI, part A, are equally applicable to the transcriptional inhibitor fusion proteins.

C. Combined Positive and Negative Regulation of Gene Expression

In addition to regulating gene expression using either a transcriptional activator or inhibitor fusion protein alone, the two types of fusion proteins can be used in combination to allow for both positive and negative regulation of expression of one or more target genes in a host cell. Thus, a transcriptional inhibitor protein that binds to tetO either (i) in the absence, but not the presence, of Tc, or (ii) in the presence, but not the absence, of Tc, can be used in combination with a transactivator protein that binds to tetO either (i) in the absence, but not the presence, of Tc, or (ii) in the presence, but not the absence, of Tc. Transactivator proteins that bind to tetO in the absence, but not the presenc, of Tc (e.g., wild-type TetR-activator fusion proteins) are described in further detail in U.S. Pat. No. 5,464,758, U.S. Ser. No. 08/076,327 and U.S. Pat. No. 5,650,298. Transactivator fusion proteins that bind to tetO in the presence, but not the absence, of Tc (e.g., mutated TetR-activator fusion proteins) are described herein (see Section I above) and in U.S. Ser. No. 08/270,637 and U.S. Pat. No. 5,654,168. Transcriptional inhibitor fusion proteins are described herein in Section IV.

As described above in Section III, Part C, when more than one TetR fusion protein is expressed in a host cell or organism, additional steps may be taken to inhibit heterodimerization between the different TetR fusion proteins. For example, a transactivator composed of a TetR of one class may be used in combination with a transcriptional inhibitor composed of a TetR of a second, different class that does not heterodimerize with the first class of TetR. Alternatively, amino acid residues of the TetR involved in dimerization may be mutated to inhibit heterodimerization. However, even if some heterodimerization between transactivator and inhibitor fusion proteins occurs in a host cell, sufficient amounts of homodimers should be produced to allow for efficient positive and negative regulation as described herein.

It will be appreciated by those skilled in the art that various combinations of activator and inhibitor proteins can be used to regulate a single tetO-linked gene of interest in both a positive and negative manner or to regulate multiple tetO-linked genes of interest in a coordinated manner or in an independent manner using the teachings described herein. The precise regulatory components utilized will depend upon the genes to be regulated and the type of regulation desired. Several non-limiting examples of how the transactivator and inhibitor fusion proteins may be used in combination are described further below. However, many other possible combinations will be evident to the skilled artisan in view of the teachings herein and are intended to be encompassed by the invention.

Figure 10:
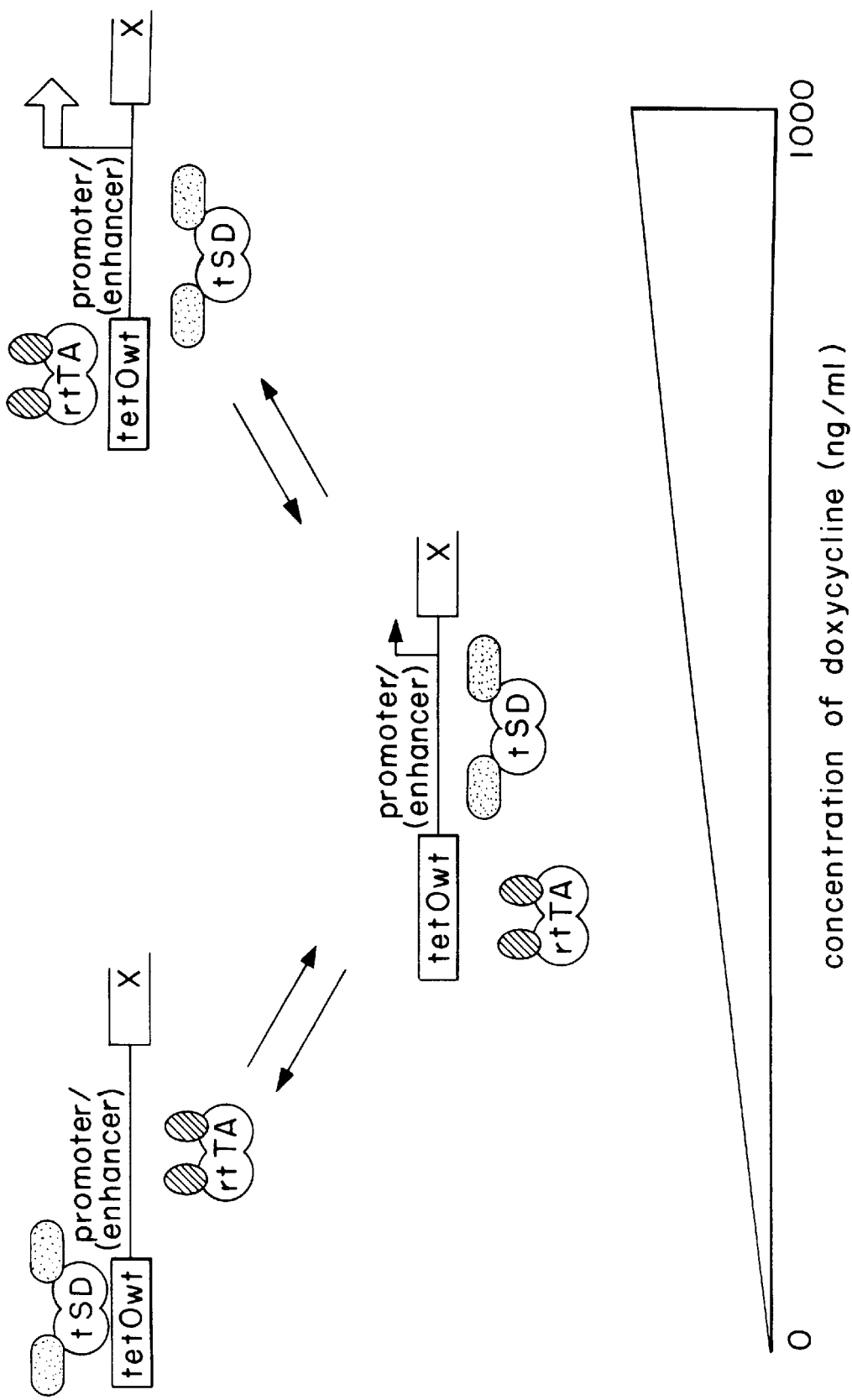
FIG. 10 is a schematic diagram of the negative and positive regulation of a tet operator (tetOwt)-linked gene of interest by a tetracycline-regulated transcriptional inhibitor protein (tSD) and a tetracycline-inducible transcriptional activator fusion protein (rtTA), respectively, in the presence of increasing concentrations of the tetracycline analogue doxycycline.

In a preferred embodiment, illustrated schematically in FIG. 10, expression of a tetO-linked target gene of interest in a host cell is regulated in both a negative and positive manner by the combination of an inhibitor fusion protein that binds to tetO in the absence, but not the presence, of tetracycline or analogue thereof (referred to as a tetracycline controlled silencing domain, or tSD) and an activator fusion protein that binds to tetO in the presence, but not the absence, of tetracycline or analogue thereof (referred to as a reverse tetracycline controlled transactivator, or rtTA). In addition to tetO sequences, the target gene is linked to a promoter, and may contain other positive regulatory elements (e.g., enhancer sequences) that contribute to basal level, constitutive transcription of the gene in the host cell. Binding of tSD to the tetO sequences in the absence of tetracycline or analogue (e.g., doxycycline) inhibits the basal constitutive transcription of the gene of interest, thus keeping the gene of interest in a repressed state until gene expression is desired. When gene expression is desired, the concentration of tetracycline or analogue (e.g., doxycycline)

in contact with the host cell increased. Upon addition of the drug, tSD loses the ability to bind to tetO sequences whereas the previously unbound rtTA acquires the ability to bind to tetO sequences. The resultant binding of rtTA to the tetO sequences linked to the gene of interest thus stimulates transcription of the gene of interest. The level of expression may be controlled by the concentration of tetracycline or analogue, the type of Tc analogue used, the duration of induction, etc., as described previously herein. It will be appreciated that the reverse combination of fusion proteins (i.e., the inhibitor binds in the presence but not the absence of the drug and the activator binds in the absence but not the presence of the drug) can also be used. In this case, expression of the gene of interest is kept repressed by contacting the host cell with the drug (e.g., culture with Tc or analogue) and gene expression is activated by removal of the drug.

In another embodiment, the activator and inhibitor fusion proteins, as described in the previous paragraph, are used in combination to coordinately regulate, in both a positive and negative manner, two genes of interest using the bidirectional tetO-linked transcription unit described in Section III, Part B above. In this case, Gene 1 and Gene 2 are linked to the same tetO sequence(s), but in opposite orientations. The inhibitor fusion protein is used to repress basal levels of transcription of both Gene 1 and Gene 2 in a coordinate manner, whereas the transactivator fusion protein is used to stimulate expression of Gene 1 and Gene 2 in a coordinate manner.

In yet another embodiment, the activator and inhbitor fusion proteins are used to independently regulate two or more genes of interest using the tetO-linked transcription units as described in Section III, Part C above. For example, in one embodiment, a transactivator fusion protein that binds to one class of tetO sequences (e.g., class A) in the presence, but not the absence of Tc or analogue is used in combination with an inhibitor fusion protein that binds to a second, different class of tetO sequences (e.g., class B) also in the presence, but not the absence, of Tc or analogue. In a host cell containing Gene 1 linked to class A tetO sequences and Gene 2 linked to class B tetO sequences, both genes will be expressed at basal levels in the absence of the drug, whereas expression of Gene 1 will be stimulated upon addition of the drug and expression of Gene 2 will be repressed upon addition of the drug.

Alternatively, in another embodiment, the transactivator binds to one class of tetO sequences (e.g., class A) in the presence, but not the absence, of Tc or analogue and the inhibitor fusion protein binds to a second, different class of tetO sequences (e.g., class B) in the absence but not the presence of Tc or analogue. In the host cell as described in the previous paragraph, Gene 1 will be expressed at basal levels in the absence of the drug and will be stimulated upon addition of the drug, whereas Gene 2 will be repressed in the absence of the drug but will have basal levels expression upon addition of the drug. Various other possible combinations will be apparent to the skilled artisan. Transactivator and inhibitor fusion proteins that bind to different classes of tetO sequences can be prepared as described in Section I, Part A. Target transcription units comprising tetO sequences of different classes can be prepared as described in Section III, Part C.

VII. Applications of the Invention

The invention is widely applicable to a variety of situations where it is desirable to be able to turn gene expression on and off, or regulate the level of gene expression, in a rapid, efficient and controlled manner without causing pleiotropic effects or cytotoxicity. Thus, the system of the invention has widespread applicability to the study of cellular development and differentiation in eukaryotic cells, plants and animals. For example, expression of oncogenes can be regulated in a controlled manner in cells to study their function. Additionally, the system can be used to regulate the expression of site-specific recombinases, such as CRE or FLP, to thereby allow for irreversible modification of the genotype of a transgenic organism under controlled conditions at a particular stage of development. For example, drug resistance markers inserted into the genome of transgenic plants that allow for selection of a particular transgenic plant could be irreversibly removed via a Tc-regulated site specific recombinase. Other applications of the regulatory system of the invention include:

A. Gene Therapy

The invention may be particularly useful for gene therapy purposes, in treatments for either genetic or acquired diseases. The general approach of gene therapy involves the introduction of nucleic acid into cells such that one or more gene products encoded by the introduced genetic material are produced in the cells to restore or enhance a functional activity. For reviews on gene therapy approaches see Anderson, W. F. (1992) *Science* 256:808–813; Miller, A. D. (1992) *Nature* 357:455–460; Friedmann, T. (1989) *Science* 244:1275–1281; and Cournoyer, D., et al. (1990) *Curr. Opin. Biotech.* 1:196–208. However, current gene therapy vectors typically utilize constitutive regulatory elements which are responsive to endogenous transcriptions factors. These vector systems do not allow for the ability to modulate the level of gene expression in a subject. In contrast, the inducible regulatory system of the invention provides this ability.

To use the system of the invention for gene therapy purposes, in one embodiment, cells of a subject in need of gene therapy are modified to contain 1) nucleic acid encoding a transactivator fusion protein of the invention in a form suitable for expression of the transactivator in the host cells and 2) a gene of interest (e.g., for therapeutic purposes) operatively linked to a tet operator sequence(s). The cells of the subject can be modified ex vivo and then introduced into the subject or the cells can be directly modified in vivo (methods for modification of the cells are described above in Section II). Expression of the gene of interest in the cells of the subject is then stimulated by administering Tc or a Tc analogue to the patient. The level of gene expression can be varied depending upon which particular Tc analogue is used as the inducing agent. The level of gene expression can also be modulated by adjusting the dose of the tetracycline, or analogue thereof, administered to the patient to thereby adjust the concentration achieved in the circulation and the tissues of interest.

Moreover, in another embodiment, a transcriptional inhibitor fusion protein is used to further control the level of expression of the gene of interest. For example, the cells of the subject can be modified to also contain a nucleic acid encoding a transcriptional inhibitor fusion protein that binds to tetO in the absence of Tc. The nucleic acid is in a form suitable for expression of the inhibitor fusion protein in the host cells. Thus, prior to administration of Tc (or analogue) to the subject, the basal level of transcription of the gene of interest will be kept silent by the inhibitor fusion protein. Upon administration of Tc, binding of the inhibitor fusion protein to tetO will be inhibited whereas binding of the transactivator fusion will be induced, thereby stimulating transcription of the gene of interest. Such combined positive and negative regulation of gene expression using both a transactivator fusion protein and transcriptional inhibitor fusion protein of the invention is illustrated schematically in FIG. 10.

Conventional detection methods known in the art, such as an enzyme linked immunosorbent assay, can be used to monitor the expression of the regulated protein of interest in the host cells and the concentration of Tc or Tc analogue can be varied until the desired level of expression of the protein of interest is achieved. Accordingly, expression of a protein of interest can be adjusted according to the medical needs of an individual, which may vary throughout the lifetime of the individual. To stop expression of the gene of interest in cells of the subject, administration of the inducing agent is stopped. Thus, the regulatory system of the invention offers the advantage over constitutive regulatory systems of allowing for modulation of the level of gene expression depending upon the requirements of the therapeutic situation.

Genes of particular interest to be expressed in cells of a subject for treatment of genetic or acquired diseases include those encoding adenosine deaminase, Factor VIII, Factor IX, dystrophin, $\beta$-globin, LDL receptor, CFTR, insulin, erythropoietin, anti-angiogenesis factors, growth hormone, glucocerebrosidase, $\beta$-glucouronidase, $\alpha$1-antitrypsin, phenylalanine hydroxylase, tyrosine hydroxylase, ornithine transcarbamylase, arginosuccinate synthetase, UDP-glucuronysyl transferase, apoA1, TNF, soluble TNF receptor, interleukins (e.g., IL-2), interferons (e.g., $\alpha$- or $\gamma$-IFN) and other cytokines and growth factors. Cells types which can be modified for gene therapy purposes include hematopoietic stem cells, myoblasts, hepatocytes, lymphocytes, skin epithelium and airway epithelium. For further descriptions of cell types, genes and methods for gene therapy see e.g., Wilson, J. M et al. (1988) *Proc. Natl. Acad. Sci. USA* 85:3014–3018; Armentano, D. et al. (1990) *Proc. Natl. Acad. Sci. USA* 87:6141–6145; Wolff, J. A. et al. (1990) *Science* 247:1465–1468; Chowdhury, J. R. et al. (1991) *Science* 254:1802–1805; Ferry, N. et al. (1991) *Proc. Natl. Acad. Sci. USA* 88:8377–8381; Wilson, J. M. et al. (1992) *J. Biol. Chem.* 267:963–967; Quantin, B. et al. (1992) *Proc. Natl. Acad. Sci. USA* 89:2581–2584; Dai, Y. et al. (1992) *Proc. Natl. Acad. Sci. USA* 89:10892–10895; van Beusechem, V. W. et al. (1992) *Proc. Natl. Acad. Sci USA* 89:7640–7644; Rosenfeld, M. A. et al. (1992) *Cell* 68:143–155; Kay, M. A. et al. (1992) *Human Gene Therapy* 3:641–647; Cristiano, R. J. et al. (1993) *Proc. Natl. Acad. Sci. USA* 90:2122–2126; Hwu, P. et al. (1993) *J. Immunol.* 150:4104–4115; and Herz, J. and Gerard, R. D. (1993) *Proc. Natl Acad. Sci. USA* 90:2812–2816.

Gene therapy applications of particular interest in cancer treatment include overexpression of a cytokine gene (e.g., TNF-$\alpha$) in tumor infiltrating lymphocytes or ectopic expression of cytokines in tumor cells to induce an anti-tumor immune response at the tumor site), expression of an enzyme in tumor cells which can convert a non-toxic agent into a toxic agent, expression of tumor specific antigens to induce an anti-tumor immune response, expression of tumor suppressor genes (e.g., p53 or Rb) in tumor cells, expression of a multidrug resistance gene (e.g., MDR1 and/or MRP) in bone marrow cells to protect them from the toxicity of chemotherapy.

Gene therapy applications of particular interest in treatment of viral diseases include expression of trans-dominant negative viral transactivation proteins, such as trans-dominant negative tat and rev mutants for HIV or trans-dominant ICp4 mutants for HSV (see e.g., Balboni, P. G. et al. (1993) *J. Med. Virol.* 41:289–295; Liem, S. E. et al. (1993) *Hum. Gene Ther.* 4:625–634; Malim, M. H. et al. (1992) *J. Exp. Med.* 176:1197–1201; Daly, T. J. et al. (1993) *Biochemistry* 32:8945–8954; and Smith, C. A. et al. (1992) *Virology* 191:581–588), expression of trans-dominant negative envelope proteins, such as env mutants for HIV (see e.g., Steffy, K. R. et al. (1993) *J. Virol.* 67:1854–1859), intracellular expression of antibodies, or fragments thereof, directed to viral products ("internal immunization", see e.g., Marasco, W. A. et al. (1993) *Proc. Natl. Acad. Sci. USA* 90:7889–7893) and expression of soluble viral receptors, such as soluble CD4. Additionally, the system of the invention can be used to conditionally express a suicide gene in cells, thereby allowing for elimination of the cells after they have served an intended function. For example, cells used for vaccination can be eliminated in a subject after an immune response has been generated the subject by inducing expression of a suicide gene in the cells by administering Tc or a Tc analogue to the subject.

The Tc-controlled regulatory system of the invention has numerous advantages properties that it particularly suitable for application to gene therapy. For example, the system provides an "on"/"off" switch for gene expression that allows for regulated dosaging a gene product in a subject. There are several situations in which it may be desirable to be able to provide a gene product at specific levels and/or times in a regulated manner, rather than simply expressing the gene product constitutively at a set level. For example, a gene of interest can be switched "on" at fixed intervals (e.g., daily, alternate days, weekly, etc.) to provide the most effective level of a gene product of interest at the most effective time. The level of gene product produced in a subject can be monitored by standard methods (e.g., direct monitoring using an immunological assay such as ELISA or RIA or indirectly by monitoring of a laboratory parameter dependent upon the function of the gene product of interest, e.g., blood glucose levels and the like). This ability to turn "on" expression of a gene at discrete time intervals in a subject while also allowing for the gene to be kept "off" at other times avoids the need for continued administration of a gene product of interest at intermittent intervals. This approach avoids the need for repeated injections of a gene product, which may be painful and/or cause side effects and would likely require continuous visits to a physician. In contrast, the system of the invention avoids these drawbacks. Moreover, the ability to turn "on" expression of a gene at discrete time intervals in a subject allows for focused treatment of diseases which involve "flare ups" of activity (e.g., many autoimmune diseases) only at times when treatment is necessary during the acute phase when pain and symptoms are evident. At times when such diseases are in remission, the expression system can be kept in the "off" state.

Gene therapy applications that may particularly benefit from this ability to modulate gene expression during discrete time intervals include the following non-limiting examples:

Rheumatoid arthritis—genes which encode gene products that inhibit the production of inflammatory cytokines (e.g., TNF, IL-1 and IL-12). can be expressed in subjects. Examples of such inhibitors include soluble forms of a receptor for the cytokine. Additionally or alternatively, the cytokines IL-10 and/or IL-4 (which stimulate a protective Th2-type response) can be expressed. Moreover, a glucocorticomimetic receptor (GCMR) can be expressed.

Hypopituitarism—the gene for human growth hormone can be expressed in such subjects only in early childhood, when gene expression is necessary, until normal stature is achieved, at which time gene expression can be downregulated.

Wound healing/Tissue regeneration—Factors (e.g., growth factors, angiogenic factors, etc.) necessary for the healing process can be expressed only when needed and then downregulated.

Anti-Cancer Treatments—Expression of gene products useful in anti-cancer treatment can be limited to a therapeutic phase until retardation of tumor growth is achieved, at which time expression of the gene product can be down-regulated. Possible systemic anti-cancer treatments include use of tumor infiltrating lymphocytes which express immunostimulatory molecules (e.g., IL-2, IL-12 and the like), angiogenesis inhibitors (PF4, IL-12, etc.), Her-regulin, Leukoregulin (see PCT Publication No. WO 85/04662), and growth factors for bone marrow support therapy, such as G-CSF, GM-CSF and M-CSF. Regarding the latter, use of the regulatory system of the invention to express factors for bone marrow support therapy allows for simplified therapeutic switching at regular intervals from chemotherapy to bone marrow support therapy (similarly, such an approach can also be applied to AIDS treatment, e.g., simplified switching from anti-viral treatments to bone marrow support treatment). Furthermore, controlled local targeting of anti-cancer treatments are also possible. For example, expression of a suicide gene by a regulator of the invention, wherein the regulator itself is controlled by, for example, a tumor-specific promoter or a radiation-induced promoter.

In another embodiment, the regulatory system of the invention is used to express angiogenesis inhibitor(s) from within a tumor via a transgene regulated by the system of the invention. Expression of angiogenesis inhibitors in this manner may be more efficient than systemic administration of the inhibitor and would avoid any deleterious side effects that might accompany systemic administration. In particular, restricting angiogenesis inhibitor expression to within tumors could be particularly useful in treating cancer in children still undergoing angiogenesis associated with normal cell growth.

In another embodiment, high level regulated expression of cytokines may represent a method for focusing a patients own immune response on tumor cells. Tumor cells can be transduced to express chemoattractant and growth promoting cytokines important in increasing an individual's natural immune response. Because the highest concentrations of cytokines will be in the proximity of the tumor, the likelihood of eliciting an immunological response to tumor antigens is increased. A potential problem with this type of therapy is that those tumor cells producing the cytokines will also be targets of the immune response and therefor the source of the cytokines will be eliminated before eradication of all tumor cells can be certain. To combat this, expression of viral proteins known to mask infected cells from the immune system can be placed under regulation, along with the cytokine gene(s), in the same cells. One such protein is the E19 protein from adenovirus (see e.g., Cox, *Science* 247:715). This protein prevents transport of class I HLA antigens to the surface of the cell and hence prevents recognition and lysis of the cell by the host's cytotoxic T cells. Accordingly, regulated expression of E19 in tumor cells could shield cytokine producer cells from cytotoxic T cells during the onset of an immune response provoked by cytokine expression. After a sufficient period of time has elapsed to eradicate all tumor cells but those expressing E19, E19 expression can be turned off, causing these cells then to fall victim to the provoked anti-tumor immune response.

Benign prostatic hypertrophy—Similar to the above, a suicide gene can be regulated by a regulator of the invention, wherein the regulator itself is controlled by, for example, a prostate-specific promoter.

The ability to express a suicide gene (e.g., an apoptosis gene, TK gene, etc) in a controlled manner using the regulatory system of the invention adds to the general safety and usefulness of the system. For example, at the end of a desired therapy, expression of a suicide gene can be triggered to eliminate cells carrying the gene therapy vector, such as cells in a bioinert implant, cells that have disseminated beyond the intended original location, etc. Moreover, if a transplant becomes tumorous or has side effects, the cells can be rapidly eliminated by induction of the suicide gene. The use of more than one Tc-controlled "on"/"off" switch in one cell allows for completely independent regulation of a suicide gene compared to regulation of a gene of therapeutic interest (as described in detail herein).

The regulatory system of the invention further offers the ability to establish a therapeutically relevant expression level for a gene product of interest in a subject, in contrast to unregulated constitutive expression which offers no flexibility in the level of gene product expression that can be achieved. A physiologically relevant level of gene product expression can be established based on the particular medical need of the subject, e.g., based on laboratory tests that monitor relevant gene product levels (using methods as described above). In addition to the clinical examples and gene products already discussed above with gene to dosaging of the gene product, other therapeutically relevant gene products which can be expressed at a desired level at a desired time include: Factor XIII and IX in hemophiliacs (e.g., expression can be elevated during times of risk of injury, such as during sports); insulin or amylin in diabetics (as needed, depending on the state of disease in the subject, diet, etc.); erythropoietin to treat erythrocytopenia (as needed, e.g., at end-stage renal failure); low-density lipoprotein receptor (LDLr) or very low-density lipoprotein receptor (VLDLr) for artherosclerosis or gene therapy in liver (e.g, using ex vivo implants). Applications to treatment of central nervous system disorders are also encompassed. For example, in Alzheimer's disease, "fine tuned" expression of choline acetyl transferase (ChAT) to restore acetylcholine levels, neurotrophic factors (e.g., NGF, BDNGF and the like) and/or complement inhibitors (e.g., sCR1, sMCP, sDAF, sCD59 etc.) can be accomplished. Such gene products can be provided, for example, by transplanted cells expressing the gene products in a regulated manner using the system of the invention. Moreover, Parkinson's disease can be treated by "fine tuned" expression of tyrosine hydroxylase (TH) to increase levodopa and dopamine levels.

In addition to the proteinaceous gene products discussed above, gene products that are functional RNA molecules (such as anti-sense RNAs and ribozymes) can be expressed in a controlled manner in a subject for therapeutic purposes. For example, a ribozyme can be designed which discriminates between a mutated form of a gene and a wild-type gene. Accordingly, a "correct" gene (e.g., a wild-type p53 gene) can be introduced into a cell in parallel with introduction of a regulated ribozyme specific for the mutated form of the gene (e.g., a mutated endogenous p53 gene) to remove the defective mRNA expressed from the endogenous gene. This approach is particularly advantageous in situations in which a gene product from the defective gene would interfere with the action of the exogenous wild-type gene.

Expression of a gene product in a subject using the regulatory system of the invention is modulated using tetracycline or analogues thereof. Such drugs can be administered by any route appropriate for delivery of the drug to its desired site of action (e.g., delivery to cells containing a gene whose expression is to be regulated). Depending on the particular cell types involved, preferred routes of administration may include oral administration, intravenous administration and topical administration (e.g., using a transdermal patch to reach cells of a localized transplant under the skin, such as keratinocytes, while avoiding any possible side effects from systemic treatment).

In certain gene therapy situations, it may be necessary or desirable to take steps to avoid or inhibit unwanted immune reactions in a subject receiving treatment. To avoid a reaction against the cells expressing the therapeutic gene product, a subject's own cells are generally used, when possible, to express the therapeutic gene product, either by in vivo modification of the subject's cells or by obtaining cells from the subject, modifying them ex vivo and returning them to the subject. In situations where allogeneic or xenogeneic cells are used to express a gene product of interest, the regulatory system of the invention, in addition to regulating a therapeutic gene, can also be used to regulate one or more genes involved in the immune recognition of the cells to inhibit an immune reaction against the foreign cells. For example, cell-surface molecules involved in recognition of a foreign cell by T lymphocytes can be downmodulated on the surface of a foreign cell used for delivery of a therapeutic gene product, such as by regulated expression in the foreign cell of a ribozyme which cleaves the mRNA encoding the cell-surface molecule. Particularly preferred cell surface molecules which can be downmodulated in this manner to inhibit an unwanted immune response include class I and/or class II major histocompatibility complex (MHC) molecules, costimulatory molecules (e.g., B7-1 and/or B7-2), CD40, and various "adhesion" molecules, such as ICAM-1 or ICAM-2. Using approaches described herein for independent but coordinate regulation of multiple genes in the same cell, the down-regulation of expression of a cell-surface molecule(s) in a host cell can be coordinated with the up-regulation of expression of a therapeutic gene. Accordingly, after therapy is completed and expression of the therapeutic gene is halted, expression of the endogenous cell surface molecule(s) can be restored to normal. Furthermore, as described above regarding anti-cancer treatments, a viral protein (e.g., adenovirus E19 protein) that downmodulates expression of MHC antigens can be regulated in host cells using the system of the invention as a means of avoiding unwanted immunological reactions.

In addition to avoiding or inhibiting an immune response against a foreign cell delivering a therapeutic gene product, it may also be necessary, in certain situations, to avoid or inhibit an immune response against certain components of the regulatory system of the invention (e.g., the regulator fusion proteins described herein) that are expressed in a subject, since these fusion proteins contain non-mammalian polypeptides that may stimulate an unwanted immune reaction. In this regard, regulator fusion proteins can be designed and/or selected for a decreased ability to stimulate an immune response in a host. For example, a transcriptional activator domain for use in the regulator fusion protein can be chosen which has minimal immunogenicity. In this regard, a wild-type transcriptional activation domain of the herpes simplex virus protein VP16 may not be a preferred transcriptional activation domain for use in vivo, since it may stimulate an immune response in mammals. Alternative transcriptional activation domains can be used, as described herein, based on their reduced immunogenicity in a subject. For example, a transcriptional activation domain of a protein of the same species as the host may be preferred (e.g., a transcriptional activation domain from a human protein for use of a regulatory fusion protein in humans). Alternatively, a regulatory fusion protein of the invention can be modified to reduce its immunogenicity in subjects, e.g., by identifying and modifying one or more dominant T cell epitopes within a polypeptide of the fusion protein (e.g., either the Tet repressor moiety or the transcriptional modulator moiety, such as a VP16 polypeptide). Such T cell epitopes can be identified by standard methods and altered by mutagenesis, again by standard methods. A modified form of a regulator fusion protein can then be selected which retains its original transcriptional regulatory ability yet which exhibits reduced immunogenicity in a subject as compared to an unmodified fusion protein.

In addition to the foregoing, all conventional methods for generally or specifically downmodulating immune responses in subjects can be combined with the use of the regulatory system of the invention in situations where inhibition of immune responses is desired. General immunosuppressive agents, such as cyclosporin A and/or FK506, can be administered to the subject. Alternatively, immunomodulatory agents which may allow for more specific immunosuppression can be used. Such agents may include inhibitors of costimulatory molecules (e.g., a CTLA4Ig fusion protein, soluble CD4, anti-CD4 antibodies, anti-B7-1 and/or anti-B7-2 antibodies or anti-gp39 antibodies).

Finally, in certain situations, a delivery vehicle for cells expressing a therapeutic gene can be chosen which minimizes exposure of transplanted cells to the immune system. For example, cells can be implanted into bioinert capsules/biocompatible membranes with pores which allow for diffusion of proteins (e.g., a therapeutic gene product of interest) out of the implant and diffusion of nutrients and oxygen into the implant but which prevent entry of immune cells, thereby avoiding exposure of the transplanted cells to the immune system (as has been applied to islet cell transplantation).

B. Production of Proteins in Vitro

Large scale production of a protein of interest can be accomplished using cultured cells in vitro which have been modified to contain 1) a nucleic acid encoding a transactivator fusion protein of the invention in a form suitable for expression of the transactivator in the cells and 2) a gene encoding the protein of interest operatively linked to a tet operator sequence(s). For example, mammalian, yeast or fungal cells can be modified to contain these nucleic acid components as described herein. The modified mammalian, yeast or fungal cells can then be cultured by standard fermentation techniques in the presence of Tc or an analogue thereof to induce expression of the gene and produce the protein of interest. Accordingly, the invention provides a production process for isolating a protein of interest. In the process, a host cell (e.g., a yeast or fungus), into which has been introduced both a nucleic acid encoding a transactivator fusion protein of the invention and a nucleic acid encoding the protein of the interest operatively linked to at least one tet operator sequence, is grown at production scale in a culture medium in the presence of tetracycline or a tetracycline analogue to stimulate transcription of the nucleotides sequence encoding the protein of interest (i.e., the nucleotide sequence operatively linked to the tet operator sequence(s)) and the protein of interest is isolated from harvested host cells or from the culture medium. Standard protein purification techniques can be used to isolate the protein of interest from the medium or from the harvested cells.

C. Production of Proteins in Vivo

The invention also provides for large scale production of a protein of interest in animals, such as in transgenic farm animals. Advances in transgenic technology have made it possible to produce transgenic livestock, such as cattle, goats, pigs and sheep (reviewed in Wall, R. J. et al. (1992)

J. Cell. Biochem. 49: 13–120; and Clark, A. J. et al. (1987) Trends in Biotechnology 5:20–24). Accordingly, transgenic livestock carrying in their genome the components of the inducible regulatory system of the invention can be constructed, wherein a gene encoding a protein of interest is operatively linked to at least one tet operator sequence. Gene expression, and thus protein production, is induced by administering Tc (or analogue thereof) to the transgenic animal. Protein production can be targeted to a particular tissue by linking the nucleic acid encoding the transactivator fusion protein to an appropriate tissue-specific regulatory element(s) which limits expression of the transactivator to certain cells. For example, a mammary gland-specific regulatory element, such as the milk whey promoter (U.S. Pat. No. 4,873,316 and European Application Publication No. 264,166), can be linked to the transactivator transgene to limit expression of the transactivator to mammary tissue. Thus, in the presence of Tc (or analogue), the protein of interest will be produced in the mammary tissue of the transgenic animal. The protein can be designed to be secreted into the milk of the transgenic animal, and if desired, the protein can then be isolated from the milk.

D. Animal Models of Human Disease

The transcriptional activator and inhibitor proteins of the invention can be used alone or in combination to stimulate or inhibit expression of specific genes in animals to mimic the pathophysiology of human disease to thereby create animal models of human disease. For example, in a host animal, a gene of interest thought to be involved in a disease can be placed under the transcriptional control of one or more tet operator sequences (e.g., by homologous recombination, as described herein). Such an animal can be mated to a second animal carrying one or more transgenes for a transactivator fusion protein and/or an inhibitor fusion protein to create progeny that carry both a tetracycline-regulated fusion protein(s) gene and a tet-regulated target sequence. Expression of the gene of interest in these progeny can be modulated using tetracycline (or analogue). For example, expression of the gene of interest can be down-modulated using a transcriptional inhibitor fusion protein to examine the relationship between gene expression and the disease. Such an approach may be advantageous over gene "knock out" by homologous recombination to create animal models of disease, since the tet-regulated system described herein allows for control over both the levels of expression of the gene of interest and the timing of when gene expression is down- or up-regulated.

E. Production of Stable Cell Lines for Gene Cloning and Other Uses

The transcriptional inhibitor system described herein can be used keep gene expression "off" (i.e., expressed) to thereby allow production of stable cell lines that otherwise may not be produced. For example, stable cell lines carrying genes that are cytotoxic to the cells can be difficult or impossible to create due to "leakiness" in the expression of the toxic genes. By repressing gene expression of such toxic genes using the transcriptional inhibitor fusion proteins of the invention, stable cell lines carrying toxic genes may be created. Such stable cell lines can then be used to clone such toxic genes (e.g., inducing the expression of the toxic genes under controlled conditions using Tc or analog). General methods for expression cloning of genes, to which the transcriptional inhibitor system of the invention can be applied, are known in the art (see e.g., Edwards, C. P. and Aruffo, A. (1993) Curr. Opin. Biotech. 4:558–563) Moreover, the transcriptional inhibitor system can be applied to inhibit basal expression of genes in other cells to create stable cell lines, such as in embryonic stem (ES) cells. Residual expression of certain genes introduced into ES stems may result in an inability to isolate stably transfected clones. Inhibition of transcription of such genes using the transcriptional inhibitor system described herein may be useful in overcoming this problem.

Advantages

The inducible regulatory system of the invention utilizing a transactivator fusion protein addresses and overcomes many of the limitations of other inducible regulatory systems in the art. For example, very high intracellular concentrations of the transcriptional activator fusion protein of the invention are not required for efficient regulation of gene expression. Additionally, since gene expression is induced by adding rather than removing the inducing agent, the induction kinetics in the system of the invention are not limited by the rate of removal of the inducing agent and thus are typically faster. Moreover, the inducing agent is only present when gene transcription is induced, thereby avoiding the need for the continuous presence of an agent to keep gene expression off.

Use of the transcriptional inhibitor fusion proteins of the invention to inhibit transcription in eukaryotic cells also provide advantages over the use of prokaryotic repressors alone (e.g., TetR, lacR) to inhibit transcription in eukaryotic cells. Since the inhibitor fusion proteins of the invention contain a eukaryotic transcriptional silencer domain, these fusion proteins should be more efficient at repressing transcription in eukaryotic cells, and thus may potentially require lower intracellular concentrations for efficient repression with less liklihood of "leakiness". Additionally, by insertion of tetO sequences into the regulatory region of an endogenous gene, the transcriptional inhibitor fusion proteins of the invention can be used to down-regulate constitutive and/or tissue-specific expression of endogenous genes.

Furthermore, in contrast to various versions of the lac system (e.g., Labow et al. (1990) Mol. Cell. Biol. 10:3343–3356; Baim et al. (1991) Proc. Natl. Acad Sci. USA 88:5072–5076), which are limited by the negative properties of the inducing agent (IPTG) and/or by the need to increase the temperature in order to induce gene expression (which may elicit pleiotropic effects), the inducing agent used in the system of the invention (Tc or an analogue thereof) has many advantageous properties: 1) Tc and analogues thereof exhibit high affinity for TetR and low toxicity for eukaryotic cells, and thus can be used for gene induction at concentrations that do not affect cell growth or morphology; 2) Tc analogues which retain TetR binding but which have reduced antibiotic activity exist and can be used as inducing agents, thereby avoiding possible side effects from the antibiotic property of Tc; 3) the pharmacokinetic properties of Tc and Tc analogues enable rapid and efficient cellular uptake and penetration of physiological barriers, such as the placenta or the blood-brain barrier; and 4) Tc analogues with different induction capabilities permit modulation of the level of gene expression.

Thus, the invention provides an inducible regulatory system which allows for rapid activation of gene transcription without cellular toxicity and a range of induction indices. The increase in gene expression upon induction typically is between 1000- and 2000-fold and can be as high as about 20,000-fold. Alternatively, lower levels of gene induction, e.g., 10-fold, can be achieved depending upon which inducing agent is used. This system can be utilized in a wide range of applications. These applications include gene therapy, large-scale production of proteins in cultured cells or in transgenic farm animals, and the study of gene function, for example in relationship to cellular development and differentiation. Moreover, the novel transcription units of the invention allow for coordinate or independent regulation of the expression of multiple genes utilizing the regulatory components of the invention.

This invention is further illustrated by the following examples which should not be construed as limiting. The contents of all references, patents and published patent applications cited throughout this application are hereby incorporated by reference.

EXAMPLE 1

Selection of a Mutated Tet Repressor and Construction of a Tetracycline Inducible Transcriptional Activator A "reverse" Tet repressor, which binds to its target DNA in the presence rather than the absence of tetracycline, was generated by chemical mutagenesis and selection essentially as described in Hecht, B. et al. (1993) *J. Bacteriology* 175:1206–1210. Single-stranded DNA (coding and non-coding strands) encoding the wild-type Tn10-derived Tet repressor was chemically mutagenized with sodium nitrite. Single-stranded DNAs (40 μg in 40 μl in Tris-EDTA buffer) were mixed with 10 μl of 2.5 M sodium acetate (pH 4.3) and 50 μl of sodium nitrate ranging between 0.25 M and 2 M and incubated for 45 to 60 minutes at room temperature. After mutagenesis, the complementary strand was synthesized using reverse transcriptase or by amplification using the polymerase chain reaction with Taq DNA polymerase. Since the mutagenesis procedure yields multiple mutations in the DNA, three fragments of the gene, of about 200 base pairs each, were individually subcloned into a wt Tet repressor gene in a recombinant expression vector to replace the corresponding portion of the wild-type gene. This created a pool of mutated Tet repressor genes wherein each gene had mostly single mutations in the 200 base pair mutagenized fragment of the gene.

The pool of mutated Tet repressors were screened in a genetic assay which positively selects for a functional interaction between a Tet repressor and its cognate operator using *E. coli.* strain WH207(λWH25) (the construction of this strain is described in detail in Wissmann, A. et al. (1991) *Genetics* 128:225–232). In this *E. coli* strain, tet operators direct the expression of divergently arranged β-galactoside (lacZ) and Lac repressor (lacI) genes and the lac regulatory region directs the expression of a galactokinase (galK) gene. Binding of Tet repressors to tet operators turns off transcription of the lacI and lacZ genes. The absence of Lac repressor allows for expression of the galK gene, which enables the *E. coli* strain to use galactose as a sole carbon source, which serves as one marker. The lacZ$^-$ phenotype serves as a second marker. Thus, bacteria containing Tet repressors which bind to tet operators have a Gal$^+$, lacZ$^-$ phenotype. Bacteria containing wild-type Tet repressors have a Gal$^+$, lacZ$^-$ phenotype in the absence of tetracycline. A mutated "reverse" Tet repressor (rTetR) was selected based upon a Gal$^+$, lacZ$^-$ phenotype in the presence of tetracycline.

The nucleotide and amino acid sequence of the rTetR mutant are shown in SEQ ID NOs: 1 (nucleotide positions 1–621) and 2 (amino acid positions 1–207), respectively. Sequence analysis of the rTetR mutant showed the following amino acid and nucleotide changes:

| aa (position) | | affected codon | |
|---|---|---|---|
| wild-type | mutant | wild-type | mutant |
| glu (71) | lys | GAA | AAA |
| asp (95) | asn | GAT | AAT |
| leu (101) | ser | TTA | TCA |
| gly (102) | asp | GGT | GAT |

Two additional mutations did not result in an amino acid exchange:

| aa (position) | | affected codon | |
|---|---|---|---|
| wild-type | mutant | wild-type | mutant |
| leu (41) | leu | TTG | CTG |
| arg (80) | arg | CGT | CGC |

To convert the rTetR mutant to a transcriptional activator, a 399 base pair XbaI/Eco47III fragment encoding amino acids 3 to 135 of rTetR (i.e., encompassing the mutated region) was exchanged for the corresponding restriction fragment of the expression vector pUHD15-1 to create pUHD17-1. In pUHD15-1, nucleotide sequences encoding wild-type TetR are linked in frame to nucleotide sequences encoding the C-terminal 130 amino acids of herpes simplex virus VP16. These transactivator sequences are flanked upstream by a CMV promoter/enhancer and downstream by an SV40poly(A) site (the construction of pUHD15-1 is described in more detail in U.S. Pat. No. 5,464,758 and Gossen, M. and Bujard, H. (1992) *Proc. Natl. Acad. Sci. USA* 89:5547–5551). Thus, in pUHD17-1, nucleotide sequences encoding the reverse TetR mutant are linked in frame to VP16 sequences to create a reverse Tc-controlled transactivator (referred to herein as tTA$^R$). The analogous exchange of the mutated region of rTetR for the wild-type region of TetR was performed with plasmid pUHD152-1, which is the same as pUHD15-1 except that it additionally contains nucleotide sequences encoding a nuclear localization signal linked in-frame to the 5' end of the nucleotide sequences encoding the Tet repressor. The amino acid sequence of the nuclear localization signal is MPKRPRP (SEQ ID NO: 5), which is linked to the serine at amino acid position 2 of TetR. The resulting expression vector encoding the reverse Tc-controlled transactivator including a nuclear localization signal (referred to herein as ntTA$^R$) was named pUHD172-1.

EXAMPLE 2

Tetracycline-Induced Stimulation of Transcription by tTA$^R$

Transient Transfection

The pUHD17-1 and pUHD172-1 expression vectors were transiently transfected by a standard calcium phosphate method into HeLa cells together with a reporter plasmid, pUHC13-3, in which heptameric tet operators are fused upstream of a minimal hCMV-promoter and a luciferase reporter gene (the reporter plasmid is described in detail in U.S. Pat. No. 5,464,758 and Gossen, M. and Bujard, H. (1992) *Proc. Natl. Acad. Sci. USA* 89:5547–5551). After incubation of the transfected cells at 37° C. for 20 hours in the presence or absence of tetracyline (or an analogue thereof), luciferase activity was assayed as follows: Cells grown to ~80% confluency in 35 mm dishes in Eagle's minimal essential medium were washed with 2 ml of phosphate-buffered saline before they were lysed in 25 mM Tris phosphate, pH 7.8/2 mM dithiothreitol/2 mM diaminocyclohexanetetraacetic acid/10% glycerol/1% Triton-X-100 for 10 minutes at room temperature. The lysate was scraped off the culture dishes and centrifuged for 10 seconds in an Eppendorf centrifuge. Next, aliquots (10 μl) of the supernatant were mixed with (250 μl) of 25 mM glycylglycine/15 mM MgSO4/5 mM ATP and assayed for luciferase activity in a Lumat LB9501 (Berthold, Wildbad, F. R. G.) using the integral mode (10 seconds). D-Luciferin (L6882, Sigma) was used at 0.5 mM. The background signal measured in extracts of HeLa cells that did not contain a luciferase gene was indistinguishable from the instrument background (80–120 relative light units (rlu)/10 sec.). Protein content of the lysate was determined according to Bradford (Bradford, M. M. (1976) *Anal. Biochem.* 72:248–254). Cells transfected with plasmids encoding either tTA$^R$ or ntTA$^R$ showed an increased level of luciferase activity in the presence of tetracyclines. This effect was consistently more pronounced when anhydrotetracycline (ATc) was used instead of tetracycline.

Stable Transfection

After this transient transfection analysis, expression vectors were prepared for stable transfection of cells. A pSV2neo-derived neomycin resistance cassette (described in Southern, P. J. and Berg, P. (1982) *J Mol. Appl. Genet.* 1:327–341) was integrated into the transactivator expression vectors pUHD 17-1 and pUHD 172-1, resulting in pUHD 17-1neo and pUHD172-1neo, respectively. pUHD 172-1neo, coding for ntTA$^R$, was stably integrated into HeLa cells by standard techniques. Ten G418-resistant cell clones were analyzed for their phenotype by transient supertransfection with pUHC13-3 carrying the luciferase gene under the control of a minimal CMV promoter and tet operators. Three clones, HR4, HR5 and HR10, showed a strong increase of luciferase activity in the presence of ATc. From these clones, HR5 was selected for further experiments.

To create stable transfectants for both ntTA$^R$ and a tet operator-linked luciferase reporter gene, HR5 cells were cotransfected with pUH13-3 and pHMR272, which encodes for hygromycin resistance (see Bernhard, H-U. et al. (1985) *Exp. Cell Res.* 158:237–243), and hygromycin resistant clones were selected. In an analogous experiment, HR5 cells were cotransfected with pUH13-7 and pHMR272. pUH13-7 contains a minimal promoter sequence spanning position +19 to −37 of the HSVtk promoter adjacent to the heptameric tetO sequences, rather than a minimal CMV promoter. From 21 hygromycin resistant clones, 10 showed inducible luciferase activity upon addition of Tc or doxycycline (Dc) to the culture medium. Clones containing the luciferase reporter gene linked to a minimal CMV promoter are referred to as HR5-C, whereas those containing the luciferase reporter gene linked to a minimal tk promoter are referred to HR5-T.

Six of the HR5 clones stably transfected with a ntTA$^R$-dependent reporter unit and previously shown to be responsive to tetracyclines were grown in parallel in the absence or presence of 1 μg/ml doxycycline. About 3×10$^4$ cells were plated in each 35 mm dish (4 dishes for each clone). After growth for 60 hours, cells were harvested and the luciferase activity of the extracts (in relative light units (rlu)/μg extracted protein) was determined. As shown in Table 1, the absolute expression levels of six clones demonstrate that activation of luciferase gene expression over 3 orders of magnitude is achieved in several of the double stable cell lines containing the ntTA$^R$ regulatory system.

It should be noted that even higher induction factors (e.g., as high as a 20,000-fold increase in expression) could be achieved if, instead of simply adding the inducing agent to the culture medium, the cells were washed prior to induction and then replated in fresh culture medium containing the inducing agent.

TABLE 1

Doxycycline-dependent luciferase activity of double stable luc+/HR5 cell clones

| Clone | Luciferase Activity, rlu/μg protein | | Induction Factor |
|---|---|---|---|
| | −Doxycycline | +Doxycycline | |
| HR5-C6 | 65 | 54,911 | 845 |
| | 62 | 69,525 | 1120 |
| HR5-C11 | 100 | 165,671 | 1660 |
| | 142 | 179,651 | 1270 |
| HR5-C14 | 43 | 44,493 | 1030 |
| | 43 | 56,274 | 1310 |
| HR5-T2 | 56 | 16,696 | 298 |
| | 40 | 16,416 | 410 |
| HR5-T15 | 6.8 | 1838 | 270 |
| | 6.5 | 1688 | 260 |
| HR5-T19 | 4.8 | 1135 | 236 |
| | 5.4 | 1285 | 237 |

Induction of Luciferase Activity by Different Tetracyclines

The ability of tetracycline and several different tetracycline analogues to induce luciferase expression in HR5-C11 cells was examined. HRS-C11 cells plated at a density of about 3×10$^4$ cells/35 mm dish (~80% confluency). After full attachment of the cells, the following tetracyclines ere added to the cultures at a concentration of 1 μg/ml: tetracycline-HCl (Tc), oxytetracycline-HCl (OTc), chlorotetracycline (CTc), anhydrotetracycline-HCl (ATc) and doxycycline-HCl (Doxy). These compounds are commercially available from Sigma Chemical Co., St. Louis, Mo., and were kept in aqueous solution at a concentration of 1 μg/ml. Cells grown in the absence of antibiotic (−) served as a control. After 3 days, the cells were harvested and the luciferase activity and the protein content of the extracts were determined. The results are shown in the bar graph of FIG. 1. Each bar in the figure (closed and hatched) represents the relative luciferase activity (normalized toward the amount of extracted protein) of a single culture dish. The mean of the luciferase activities obtained from the two plates grown without tetracyclines was defined as 1. Tc, CTc and OTc showed modest stimulation of luciferase activity. By contrast, Atc and Doxy stimulated luciferase activity approximately 1000 and 1500 fold, respectively.

Dose-response of Luciferase Activity to Doxycycline in HR5-C11 Cells

Figure 2:
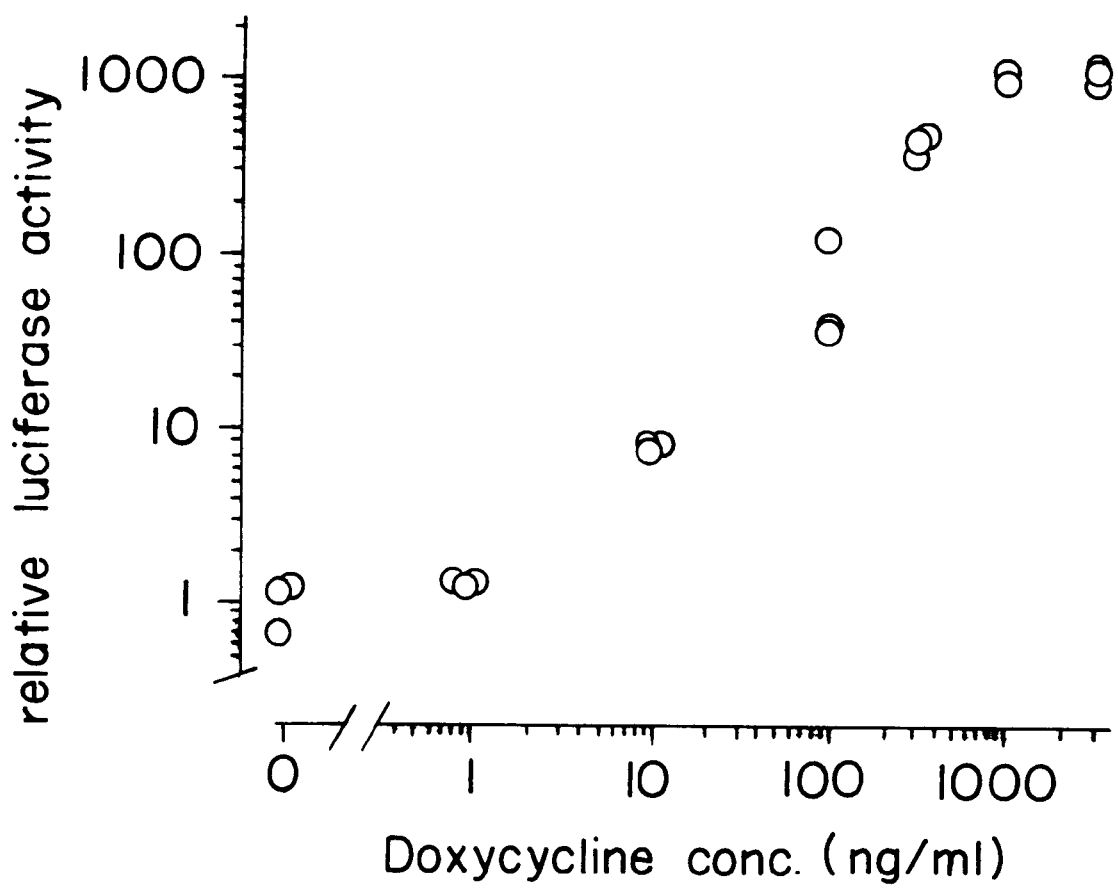
FIG. 2 is a graph depicting the relative luciferase activity in HR5-C11 cells when incubated with different concentrations of doxycycline. The results of three independent experiments are shown.

The above-described experiment examining the induction ability of different tetracyclines revealed that doxycycline was the most potent effector of the tetracyclines examined. Doxycycline was therefore selected to quantitatively analyze its dose-response. HR5-C11 cells were incubated with different concentrations of doxycycline and luciferase activity was measured. The data of three independent experiments are shown in FIG. 2. At less than 10 ng/ml in the culture medium, doxycycline is ineffective at inducing luciferase activity. However, when the concentration was raised above 10 ng/ml, an almost linear increase in expression of luciferase was observed. Maximal activation was achieved at 1 μg/ml. At concentrations above 3 μg/ml, doxycycline showed a slight growth-inhibitory effect on HeLa cells as determined in a MTT-assay.

Kinetics of Induction of the ntTAR$^R$ System

Figure 3:
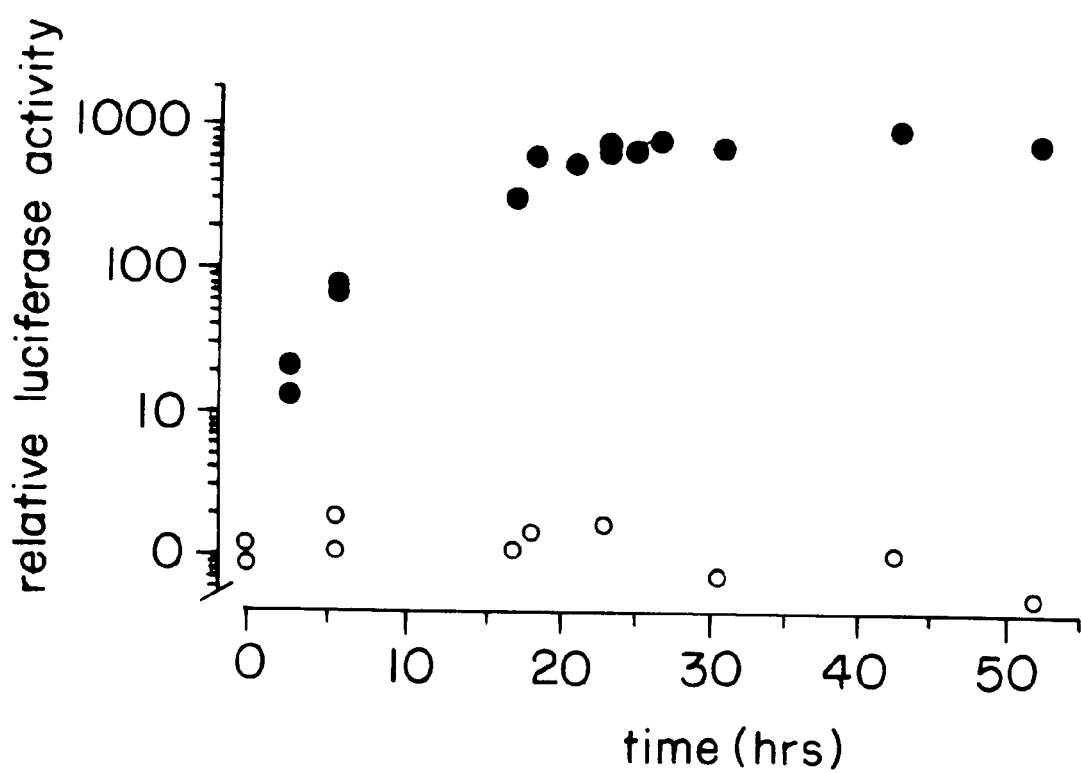
FIG. 3 is a graph depicting the kinetics of induction of luciferase activity in HR5-C11 cells by doxycycline. HR5-C11 cultures were exposed to 1 μg/ml of doxycycline and luciferase activity was measured after different time intervals; (●) cultures containing doxycycline, (o) cultures grown in the absence of antibiotic.

To examine the kinetics of doxycycline-induced ntTA$^R$-mediated induction of gene expression, the time course of induction of luciferase activity in HR5-C11 cells was monitored after addition of doxycycline to the medium (final concentration 1 µg/ml). Cells were cultured in the presence of doxycycline and after various time intervals, the cells were harvested and luciferase activity was determined as described above. As shown in FIG. 3, a 100-fold induction of luciferase activity was observed after 5.5 hours incubation with Doxy. Fully induced levels were achieved in less than 24 hours of incubation with Doxy. Thus, these results indicate that induction of gene expression occurs rapidly following exposure of the cells to the inducing agent.

EXAMPLE 3

Coordinate Regulation of the Expression of Two Nucleotide Sequences by a Tc-Controlled Transcriptional Activator A recombinant expression vector for coordinate, bidirectional transcription of two nucleotide sequences was constructed comprising, in a 5' to 3' direction: a luciferase gene, a first minimal promoter, seven tet operator sequences, a second minimal promoter and a LacZ gene. The construct is illustrated in FIG. 6. In this construct, the luciferase and LacZ genes are oriented such that they are transcribed in opposite orientations relative to the tet operator sequences, i.e., the luciferase gene is transcribed in a 5' to 3' direction from the bottom strand of DNA, whereas the LacZ gene is transcribed in a 5' to 3' direction from the top strand of DNA. The luciferase gene is followed by an SV40 polyadenylation signal, whereas the LacZ gene is followed by a β-globin polyadenylation signal.

Figure 8A:
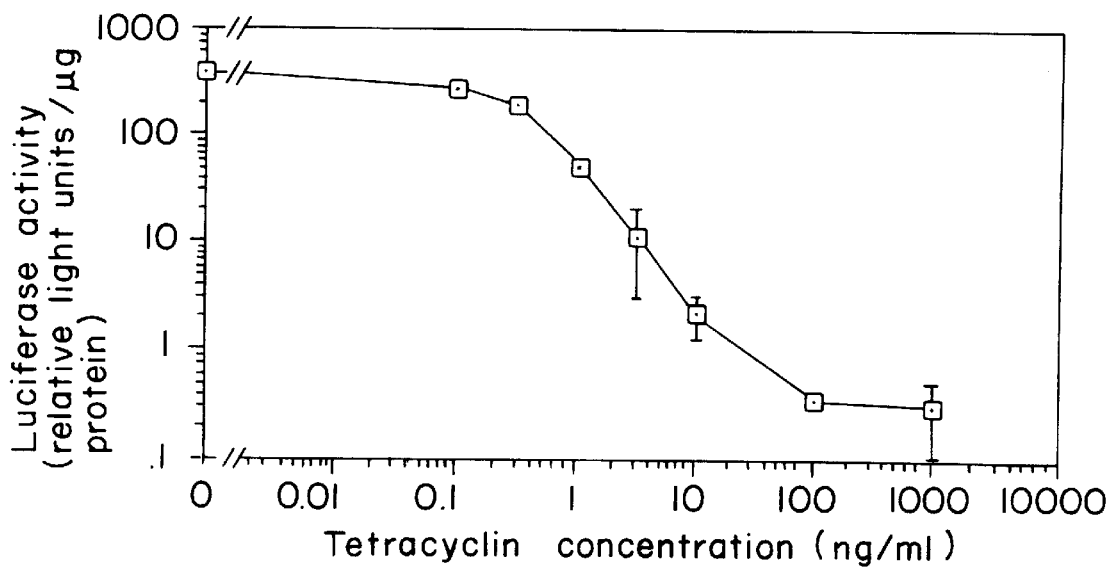
FIGS. 8A–B are two graphs depicting coordinate expression of luciferase (FIG. 8A) and β-galactosidase (FIG. 8B) activity by a tetracycline-regulated transcriptional activator.
Figure 8B:
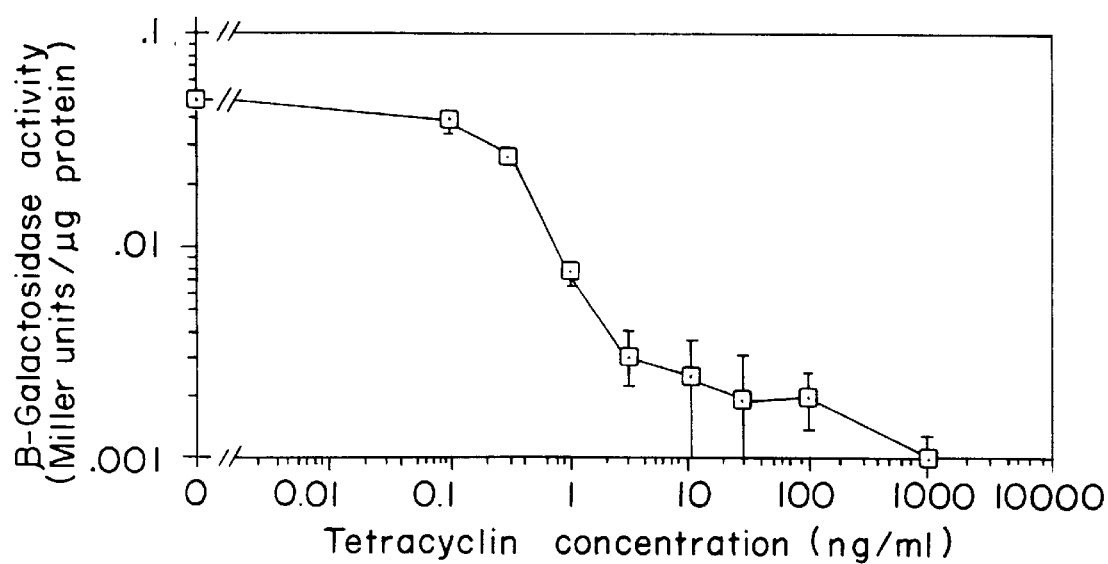

The construct was transfected into the HeLa cell line HtTA-1 cells, which express a wild-type Tet repressor-VP16 fusion protein (referred to as tTA and described in Gossen, M. and Bujard, H. (1992) *Proc. Natl. Acad. Sci. USA* 89:5547–5551). The tTA fusion protein binds to tet operator sequences in the absence of Tc (or analogue) but not in the presence of Tc (or analogue). The construct was cotransfected into HtTA-1 cells with a plasmid which confers hygromycin resistance and stably transfected clones were selected based upon their hygromycin resistant phenotype. Selected hygromycin resistant (Hygr$^r$) clones were examined for luciferase and β-galactosidase activity. Clones positive for all three markers (Hygr$^r$, luc$^+$, β-gal$^+$) were then examined for tetracycline-dependent coregulation of expression of luciferase and β-galactosidase activity by culturing the clones in increasing amounts of tetracycline and measuring luciferase and β-galactosidase activity. The results of such an experiment using clone Ht1316-8/50 are shown in FIG. 8. In the absence of tetracycline (in which case tTA can bind to tet operators and activate gene expression), both luciferase and β-galactosidase activity is detected. In the presence of increasing amounts of tetracycline, luciferase and β-galactosidase activity are coordinately and equivalently downregulated. This data demonstrates that expression of two genes can be coordinately regulated by a tetracycline-controlled transactivator by operatively linking the two genes to the same tet operator sequence(s).

EXAMPLE 4

Figure 11:
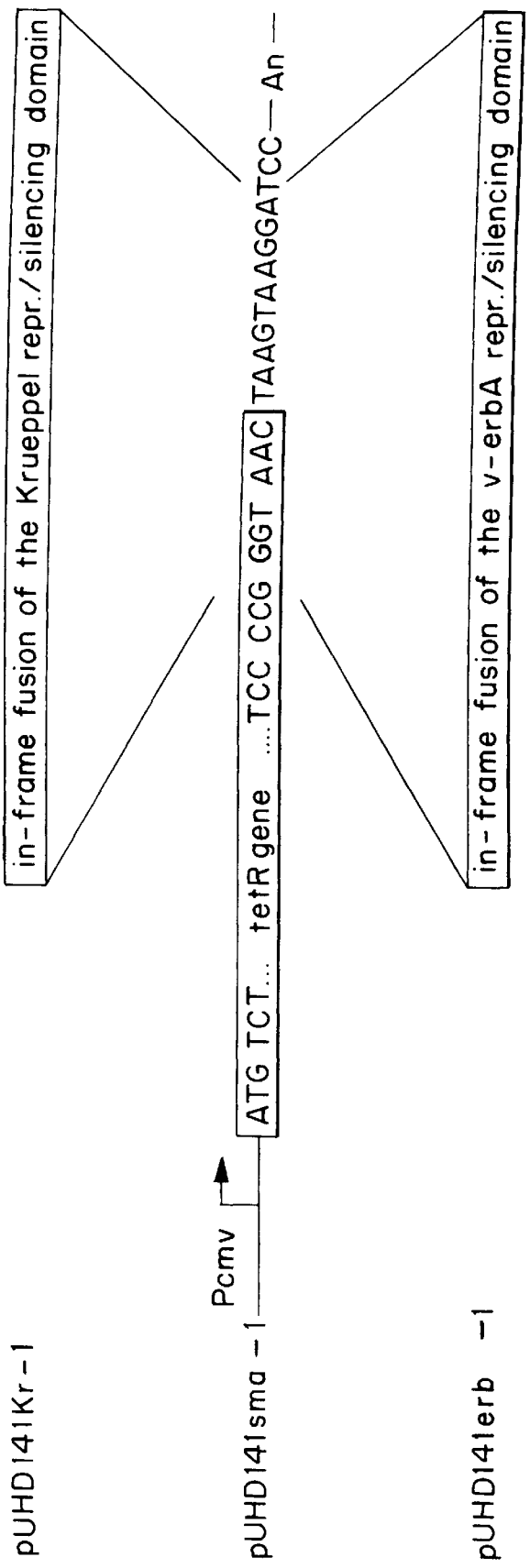
FIG. 11 is a schematic diagram of the construction of TetR-silencer domain fusion contructs by in-frame fusion of nucleic acid encoding either a Krueppel or v-erbA silencer domain to the 3' end of nucleic acid encoding a Tet repressor (tetR gene). The nucleotide sequence of the indicated regions of pUHD141Kr-1, pUHD141sma-1, and pUHD141erb-1 are set forth as SEQ ID NOs:35, 36, and 37, respectively.

Construction of a Tetracycline-Regulated Transcriptional Inhibitor Fusion Protein Comprising TetR and a Krueppel Silencer Domain To contruct an expression vector encoding a tetracycline-regulated transcriptional inhibitor of the invention (also referred to as a tetacycline controlled silencer domain, or tSD), a nucleic acid fragment encoding a transcriptional silencer domain is ligated into an expression vector containing nucleotide sequences encoding a wild-type or modified (i.e., mutated) TetR such that the silencer domain coding sequences are ligated in-frame with the TetR coding sequences. The plasmid pUHD141sma-1 contains nucleotide sequences encoding a wild-type Tn10 -derived Tet repressor (the nucleotide and amino acid sequences of which are shown in SEQ ID NOs: 16 and 17, respectively). In pUHD141sma-1, the TetR coding sequence is linked at its 5' end to a CMV promoter and at its immediate 3' end to a nucleotide sequence that creates a polylinker into which additional nucleic acid fragments can be introduced. The nucleotide sequence across this polylinker region is: TCC CCG GGT AAC TAA GTA AGG ATC C (SEQ ID NO: 24) (wherein TCC CCG GGT ACC encode amino acid residues 205–208 of TetR, namely Ser-Gly-Ser-Asn). This polylinker region includes restriction endonuclease sites for PspAI (CCC GGG) and BamHI (GGA TCC). Downstream of the polylinker region, the plasmid contains an SV40-derived polyadenylation signal. The pUHD141sma-1 vector is illustrated schematically in FIG. 11.

To construct an expression vector encoding a fusion protein between TetR and a transcriptional silencer domain from the Drosophila Krueppel (Kr) protein, a nucleic acid fragment encoding a silencer domain from Kr is amplified by the polymerase chain reaction (PCR) using Kr cDNA as a template. Oligonucleotide primers are designed which amplify a nucleic acid fragment encoding the C-terminal 64 amino acids of Kr (referred to as C64KR). This region corresponds to amino acid positions 403–466 of the native protein. The nucleotide and amino acid sequences of C64KR are shown in SEQ ID NO: 20 and SEQ ID NO: 21, respectively. PCR primers are designed to include restriction endonuclease sites such that the resultant amplified fragment contains restriction endonuclease sites at its 5' and 3' ends. Restriction endonuclease sites are chosen that are contained within the polylinker of pUHD141sma-1 which allow in-frame, directional ligation of the amplified fragment into the polylinker site. For example, PCR primers are designed which incorporate a PspAI site (CCC GGG) at the 5' end of the fragment encoding C64KR and a BamHI site at the 3' end of the fragment. After a standard PCR reaction, the amplified fragment and pUHD141-sma1 are digested with PspAI and BamHI. The amplified fragment is then ligated directionally into the polylinker site of pUHD141-sma1 using standard ligation conditions to create the expression vector pUHD141kr-1. Standard techniques are used to isolate the desired plasmid and confirm its construction. Construction of pUHD141kr-1 is illustrated schematically in FIG. 11.

The resultant pUHD141kr-1 expression vector contains nucleotide sequences encoding a fusion protein comprising amino acids 1–207 of the wild type TetR linked in-frame to amino acids 403–466 of Kr (C64KR). The nucleotide and amino acid sequences cross the junction of the fusion protein are as follows: AGT GGG TCC CCG GGT GAC TG GAA (SEQ ID NO: 25) and Ser-Gly-Ser-Pro-Gly-Asp-Met-Glu (SEQ ID NO: 26). Ser-Gly-Ser corresponds to amino acids 205–207 of TetR, Pro-Gly are encoded by the polylinker and Asp-Met-Glu correspond to the amino acids 403–405 of C64KR.

Similarly, an expression vector encoding a fusion protein of a mutated TetR (that binds to tetO only in the presence of Tc) and C64KR can be constructed as described above using nucleotide sequences encoding a mutant TetR (the nucleotide and amino acid sequences of which are shown in SEQ ID NOs: 18 and 19, respectively) in place of the wild type TetR sequences in pUHD141-sma1.

An expression vector encoding a TetR-Kr fusion protein (e.g., pUHD141kr-1) is transiently or stably transfected into host cells as described in Example 2 to express the TetR-Kr fusion protein in the host cell. A reporter gene construct containing one or more tetO sequences, a minimal promoter and a reporter gene, such as luciferase, is also transfected into the cells as described in Example 2. (Reporter gene constructs are described in further detail in U.S. Pat. No. 5,464,758 and Gossen, M. and Bujard, H. (1992) Proc. Natl. Acad. Sci. USA 89:5547–5551). Luciferase activity in the presence and absence of increasing concentrations of Tc or an analogue, e.g., doxycycline, is measured as described in Example 2. For the wild type TetR-Kr fusion protein described above, the transcriptional inhibiting ability of the fusion protein is determined by comparing the amount of luciferase activity in the presence of doxycycline (no repression) to the amount of luciferase activity in the absence of doxycycline (repression). The transcriptional inhibiting activity of the fusion protein can also be tested using reporter gene constructs that exhibit higher basal levels of expression (i.e., higher levels of expression in the presence of doxycycline) by using a reporter gene construct that contains additional positive regulatory elements (e.g., enhancer sequences).

EXAMPLE 5

Construction of a Tetracycline-Regulated Transcriptional Inhibitor Fusion Protein Comprising TetR and a v-erbA Silencer Domain To construct an expression vector encoding a fusion protein between TetR and a transcriptional silencer domain from the v-erbA oncogene product, a nucleic acid fragment encoding a silencer domain from v-erbA is ligated in-frame into pUHD141sma-1 as described in Example 4. A nucleic acid fragment encoding a v-erbA silencer domain suitable for ligation into pUHD141sma-1 is amplified by the polymerase chain reaction (PCR) using a v-erbA cDNA as a template. Oligonucleotide primers are designed which amplify a nucleic acid fragment encoding amino acids 364–635 of the native v-erbA protein. The nucleotide and amino acid sequences of this region of v-erbA are shown in SEQ ID NO: 22 and SEQ ID NO: 23, respectively. As described in Example 4, PCR primers are designed such that the amplified v-erbA fragment contains restriction endonuclease sites at its 5' and 3' ends, such as PspAI at the 5' end and BamHI at the 3' end. After a standard PCR reaction, the amplified fragment and pUHD141-sma1 are digested with PspAI and BamHI. The amplified fragment is then ligated directionally into the polylinker site of pUHD141-sma1 using standard ligation conditions to create the expression vector pUHD141kr-1. Standard techniques can be used to isolate the desired plasmid and confirm its construction. Construction of pUHD141erb-1 is illustrated schematically in FIG. 11.

The resultant pUHD141erb-1 expression vector contains nucleotide sequences encoding a fusion protein comprising a wild type TetR linked in-frame to amino acids 364–635 of v-erbA. The nucleotide and amino acid sequences across the junction of the fusion protein are as follows: AGT GGG TCC CCG GGT CTG GAC GAC (SEQ ID NO: 27) and Ser-Gly-Ser-Pro-Gly-Leu-Asp-Asp (SEQ ID NO: 28). Ser-Gly-Ser corresponds to amino acids 205–207 of TetR, Pro-Gly are encoded by the polylinker and Leu-Asp-Asp correspond to amino acids 364–366 of the v-erbA silencer domain.

As described in Example 4, an expression vector encoding a fusion protein of a mutated TetR (that binds to tetO only in the presence of Tc) and a v-erbA silencer domain can be constructed as described above using nucleotide sequences encoding a mutant TetR (the nucleotide and amino acid sequences of which are shown in SEQ ID NOs: 18 and 19, respectively) in place of the wild type TetR sequences in pUHD141-sma1.

Expression of the TetR-v-erbA fusion protein in host cells and assaying of the transcriptional inhibiting activity of the fusion protein is as described in Example 4 for the TetR-Kr fusion protein.

EXAMPLE 6

Regulation of Gene Expression in Transgenic Animals by tTA$^R$

To examine the ability of tTA$^R$ to regulate gene expression in vivo, transgenic strains of mice were constructed which contained heterologous chromosomal insertions of either a tTA$^R$ expression construct or a reporter gene operably linked to tet operators. Single transgenic strains containing either a tTA$^R$ expression construct or the tetO-linked reporter gene were then cross bred and double transgenic progeny were identified. The double transgenic animals were then characterized as to the ability of tTA$^R$, in a tetracycline dependent manner, to regulate expression of the reporter gene. This example demonstrates that tTA$^R$ effectively stimulates the expression of a gene operably linked to tet operators in tissues of the animals in vivo upon administration of tetracycline (or analogue) to the animals, whereas expression of the tetO-linked gene remains at background levels in the absence of tetracycline or an analogue. These results demonstrate that the tetracycline-controlled transcriptional regulatory system described herein functions effectively in animals, in addition to cell lines in vitro.

Generation of Mice Transgenic for a $P_{hCMV}$-tTA$^R$ Expression Unit

Mice expressing tTA protein were obtained by pronuclear injection into fertilized oocytes of a 2.7 kb XhoI-PfmI fragment excised from plasmid pUHG17-1. This DNA fragment contained the tTA$^R$ gene (shown in SEQ ID NO: 1) under the transcriptional control of the human CMV IE promoter (position +75 to −675) together with a rabbit β-globin polyadenylation site including an intron. The human CMV IE promoter is a constitutive promoter that allows expression of the mutated tetR-VP16 fusion protein in all cells where chromosomal integration of the DNA sequence encoding tTA$^R$ has occurred. DNA was injected into fertilized oocytes at a concentration of approximately 5 ng per µl by standard techniques. Transgenic mice were generated from the injected fertilized oocytes according to standard procedures. Transgenic founder mice were analyzed using polymerase chain reaction (PCR) and Southern hybridization to detect the presence of the tTA$^R$ transgene in chromosomal DNA of the mice. Two transgenic mouse lines, CR3 and CR4 were identified and crossbred with another transgenic mouse line carrying a luciferase reporter gene under the control of tetO sequences. (described further below).

Generation of Mice Transgenic for the $P_{hCMV^*-1}$ Luciferase Reporter Unit

Mice carrying a $P_{hCMV^*-1}$ luc reporter gene expression unit were generated by pronuclear injection into fertilized oocytes of a 3.1 kb XhoI-EaeI fragment excised from plasmid pUHC13-3. This DNA-fragment contains the luciferase gene under transcriptional control of the tetracycline-responsive $P_{hCMV*-1}$ promoter (SEQ ID NO: 8), together with an SV40 t early polyadenylation site including an intron. DNA was injected into oocytes at a concentration of approximately 5 ng per μl and transgenic mice were generated according to standard procedures. Transgenic founder mice were analyzed using Southern hybridization to detect the presence of the $P_{hCMV*-1}$ luc transgene in chromosomal DNA of the mice. A mouse line transgenic for the tetO-linked luciferase reporter gene, L7, was crossbred with the $tTA^R$ transgenic lines CR3 and CR4 (described further below).

Generation of Mice transgenic for the $P_{hCMV*-1}$ luc and $P_{hCMV}tTA^R$

Having constructed single transgenic mice expressing $tTA^R$ or carrying $P_{hCMV*-1}$ luc, double transgenic mice carrying both the tTA expression vector and the luciferase reporter-units were obtained through cross breeding of heterozygous mice transgenic for one of the two transgenes. Double transgenic animals were identified by standard screenings (e.g., PCR and/or Southern hybridization) to detect the presence of both the $tTA^R$ transgene and the $P_{hCMV*-1}$ luc transgene in chromosomal DNA of the mice.

Induction and Analysis of Luciferase Activity in Tissue Samples from Mice

For oral Administration, tetracycline or its derivative doxycycline were given in the drinking water at a concentration of 200 μg per ml with 5% sucrose to hide the bitter taste of the antibiotics. For lactating mice, the concentration was 2 mg per ml with 10% sucrose to ensure a sufficient uptake via the milk by the young.

To analyze luciferase activity, mice were killed by cervical dislocation and tissue samples were homogenized in 2 ml tubes containing 500 μl lysis-buffer (25 mM Tris phosphate, pH 7.8/2 mM DTT/2 mM EDTA/10% glycerol/1% Triton X100) using a Ultra-Turrax. The homogenate was frozen in liquid nitrogen and centrifuged after thawing for 5 min at 15,000 g. 2–20 μl of the supernatant were mixed with 250 μl luciferase assay buffer (25 mM glycylglycine, pH 7.5/15 mM $MgSO_4$/5 mM ATP) and luciferase activity was measured for 10 sec after the injection of 100 μl of a 125 μM luciferin solution using Berthold Lumat LB 9501. The protein concentration of the homogenate was determined using Bradford assay and luciferase activity was calculated as relative light units (rlu) per μg of total protein.

Results

Figure 12:
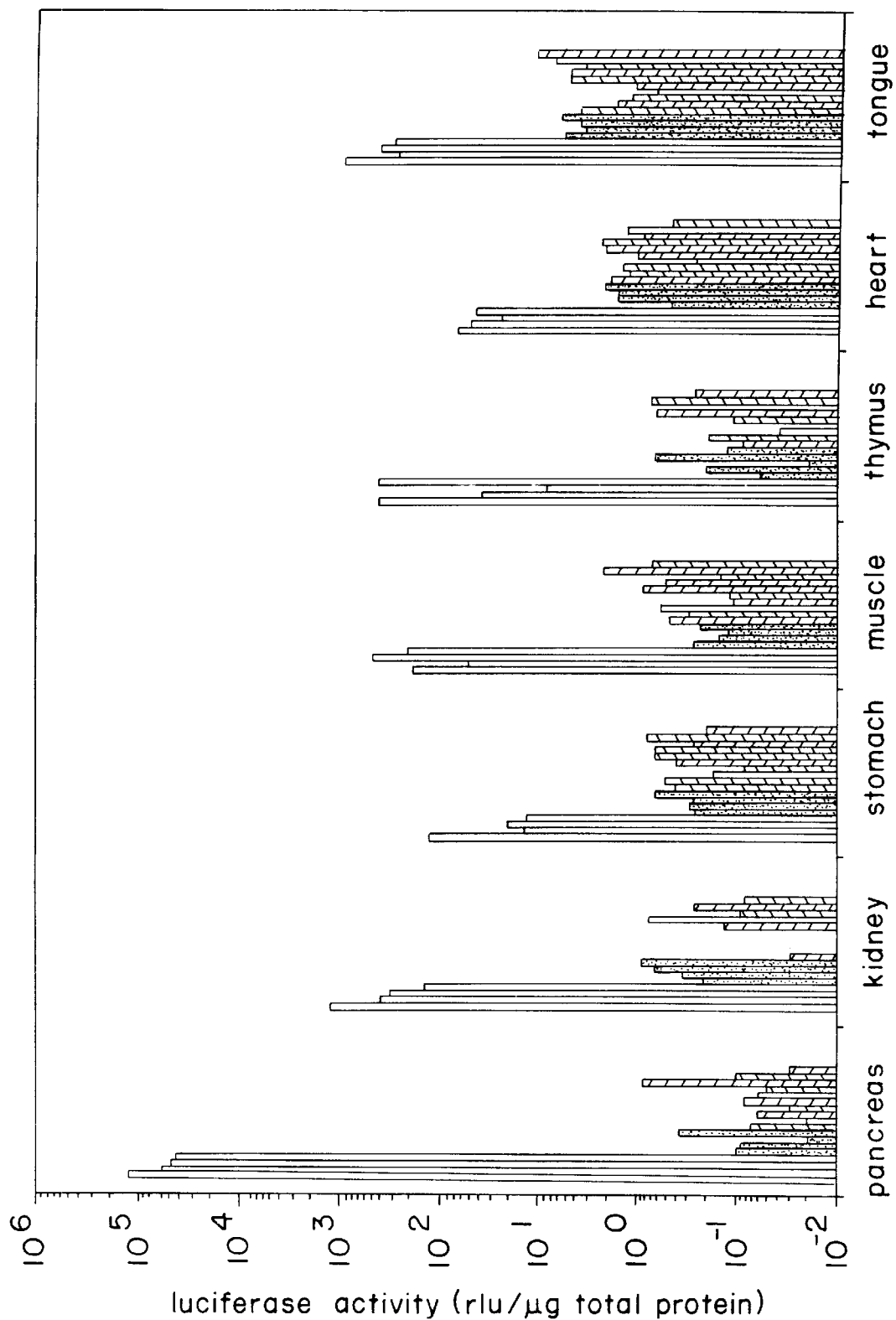
FIG. 12 is a graphic representation of the expression of luciferase activity in mice transgenic for the luciferase reporter gene alone (checked columns at right) or double transgenic animals carrying the luciferase reporter gene and a tTA$^R$ transgene, either in the absence of doxycycline (dark columns in middle) or in the presence of doxycycline (light columns at left).

Mice from 2 lines carrying the $P_{hCMV}$-$tTA^R$ transgene (CR3 and CR4) were mated with mice from line L7, transgenic for $P_{hCMV*-1}$ luc. The L7 line shows a very low but detectable background of luciferase activity in different organs that is probably due to position effects at the integration side. The background luciferase activity in different tissues of the L7 single transgenic mice is illustrated graphically in FIG. 12, represented by the checked columns on the right-hand side for each tissue examined (each column represents the results from one animals). The luciferase activity in different tissues of the C3/L7 double transgenic mice in the absence of the tetracycline analogue doxycycline (i.e., uninduced conditions) is illustrated graphically in FIG. 12, represented by the dark columns in the middle for each tissue examined. The luciferase activity in different tissues of the C3/L7 double transgenic mice in the presence of doxycycline (i.e., induced conditions) is illustrated graphically in FIG. 12, represented by the light columns on the left-hand side for each tissue examined.

Luciferase activity was detectable in the seven tissues of the double transgenic mice examined: pancreas, kidney, stomach, muscle, thymus, heart and tongue. The tissue pattern of activated luciferase levels (i.e., in the presence of doxycycline) in the double transgenic mice was similar to expression patterns of the hCMV IE promoter reported in the literature. This is consistent with expression of the luciferase reporter gene being regulated by $tTA^R$ (which is expressed in the mice under the control of the hCMV IE promoter). The level of reporter gene induction varied among the different tissues examined. Regulation factors up to 100,000 fold (i.e., 5 orders of magnitude) were achieved, e.g. in the pancreas.

EXAMPLE 7

Combinatorial Regulatory Schemes using Tetracycline-Regulated Fusion Proteins

In this example, the ability to use the various tetracycline-regulated transcriptional activators and inhibitors described herein in combination, e.g., to regulate expression of two gene expression in a single cell using two different transactivators or one gene in a cell using both a transactivator and an inhibitor, was investigated further. In a first series of experiments, various Tet repressors having mutations within the DNA binding domain of the protein were examined for their ability to bind either a wild type tetO sequence or various tetO variants to select for Tet repressors having specificity for variant tetO sequences. In a second series of experiments, Tet repressors having specificity for different variant tetO sequences were converted into either a tTA (which binds to its target tetO in the absence of Tc) or a $tTA^R$ (which binds to its target tetO in the presence of Tc) and used to regulate gene expression in host cells. In a third series of experiments (described in Part C below), various combinations of different classes of Tet repressors were examined for their ability to heterodimerize to identify classes of Tet repressors which do not heterodimerize. Finally in Part D, below, the results from the three preceding analyses are combined to present preferred model systems for 1) regulating two tetO-linked genes in one cell using a tTA and a $tTA^R$ having different variant tetO specificities and 2) regulating the expression of one tetO-linked gene using both a Tc-regulated transcriptional activator and a Tc-regulated transcriptional inhibitor.

A. Tet Operator Binding Specificity of Tet Repressors Mutated within the DNA Binding Domain A series of amino acid substitutions were made in the Tn10 Tet repressor within a region of the protein constituting the DNA binding domain (DBD) (i.e., the region of the protein which is thought to interact with a target tetO sequence). Amino acid substitutions were introduced into TetR by standard mutagenesis of a DNA molecule encoding the TetR. The ability of a DBD-mutated TetR to bind either a wild-type B class tetO or mutated variants thereof was then analyzed by introducing an expression vector encoding the DBD-mutated TetR into *E. coli*, together with a reporter gene comprising a β-galactosidase gene operatively linked to either a wild-type tetO sequence (referred to as "4T") or tetO sequences having a nucleotide substitution at either the 4 or 6 position ("4C", "6C", "4A" or "4G"). The β-galactosidase activity in the cells was measured in the absence or presence of the TetR construct The ability of the TetR protein to bind to the tetO sequence was determined by examining the % repression of β-galactosidase activity in the cell.

In a first series of experiments, a proline to glutamine mutation was introduced at position 39 ("39PQ"), alone or together with additional mutations at positions 37, 41 and/or 42. The results of these analyses are summarized below in Tables 2 and 3. In these tables, β-galactosidase activity in the absence of TetR is standardized as 100%. In the presence of a TetR that can bind the target tetO sequence linked to the reporter gene, β-galactosidase activity is reduced (e.g., in the presence of a wild-type TetR that can bind its target tetO sequence, β-galactosidase activity typically is less than 1%). In contrast, in the presence of a DBD-mutated TetR that cannot bind the target tetO sequence linked to the reporter gene, β-galactosidase activity remains near 100%.

TABLE 2

| Tet Repressor | tet Operator | | | | |
|---|---|---|---|---|---|
| | 4C | 4T (wt) | 6C | 4A | 4G |
| wt | 57.3 ± 1.6 | 0.1 ± 0.1 | 47.1 ± 2.7 | 28 ± 0.7 | 88.3 ± 2.1 |
| 39PQ | 46.7 ± 1.2 | 96.4 ± 0.1 | 88.4 ± 4.5 | 97.3 ± 1.2 | 99.2 ± 4.2 |
| 37ES | 9.3 ± 0.3 | 0.3 ± 0.1 | 35 ± 2.0 | 6 ± 0.1 | 64.2 ± 2.2 |
| 37ES39PQ | 6.2 ± 0.5 | 92.5 ± 2 | 100.2 ± 2.3 | 95.8 ± 1.1 | 99.1 ± 3.9 |
| 37ES39PQ42YM | 8.4 ± 0.3 | 96.7 ± 0.8 | 95.6 ± 1.1 | 98.8 ± 3 | 99.6 ± 3.4 |
| 37ES39PQ41LV | 14.7 ± 1 | 95.1 ± 0.8 | 97.6 ± 2.8 | 102 ± 5.3 | 96.2 ± 3.1 |
| 37ES39PQ41LV42YM | 0.2 ± 0.1 | 87.9 ± 0.7 | 96.1 ± 2.2 | 74.5 ± 3.4 | 88.2 ± 1.9 |
| 37ES39PQ41LI42YM | 0.7 ± 0.2 | 87.7 ± 2.9 | 98.4 ± 1.2 | 79.4 ± 3.4 | 87.2 ± 0.6 |
| 37ES39P41LV42YS | 99.9 ± 3.3 | 98.4 ± 2.1 | 98.8 ± 1.9 | 99.8 ± 1.6 | 100.1 ± 2.6 |
| 37ET | 13.7 ± 0.6 | 0.2 ± 0.1 | 40.9 ± 2.9 | 8.1 ± 0.6 | 87.4 ± 2.5 |
| 37ET39PQ | 4.8 ± 0.2 | 93.5 ± 3.4 | 99.4 ± 2.2 | 102.3 ± 2.7 | 100.4 ± 1.7 |
| 37ET39PQ42YM | 1.4 ± 0 | 93.8 ± 6.2 | 100.9 ± 3.9 | 103 ± 1.3 | 92.2 ± 0.6 |
| 37ET39PQ41LV | 4.3 ± 0.2 | 92 ± 0.9 | 100 ± 0.2 | 100.2 ± 4.2 | 97.9 ± 1.1 |
| 37ET39PQ41LV42YM | 0.1 ± 0.1 | 95.8 ± 0.1 | 104.2 ± 2.7 | 93.1 ± 1.4 | 91 ± 4.1 |
| 37EL | 82 ± 0.4 | 0.4 ± 0.1 | 72.5 ± 4.8 | 84.8 ± 2.5 | 101.6 ± 1.9 |
| 37EL 39PQ | 58.8 ± 0.5 | 95.6 ± 2.2 | 98.3 ± 4 | 98.9 ± 2.7 | 102.4 ± 4.1 |
| 37EL39PQ42YM | 8.2 ± 0.5 | 96.7 ± 0.3 | 99 ± 4.5 | 95.4 ± 2.5 | 97 ± 3 |
| 37EL39PQ41LV | 73.9 ± 0.2 | 95.3 ± 0.4 | 98.2 ± 2.5 | 94.5 ± 0.9 | 98.1 ± 4.9 |
| 37EL39PQ41LV42YM | 20.5 ± 0.1 | 92.3 ± 1.2 | 95.6 ± 2.9 | 96.1 ± 0.6 | 102.2 ± 4.8 |
| 37EL39PQ41LM42YM | 0.7 ± 0.1 | 96.3 ± 2.2 | 98.2 ± 2.5 | 96.9 ± 1.2 | 102.6 ± 0.5 |
| 39PQ41LM | 90.1 ± 2.1 | 97.2 ± 3.4 | 99.4 ± 3.4 | 96.5 ± 2.8 | 96.9 ± 2.2 |
| 39PQ42YM | 71.1 ± 1.8 | 95.6 ± 3.3 | 100.6 ± 1.6 | 97 ± 1.7 | 97.1 ± 8.2 |
| 39PQ41LM42YM | 72.3 ± 0.7 | 98.6 ± 5.7 | 99.3 ± 0.4 | 93.5 ± 4.8 | 99.1 ± 4.5 |
| 41LM | 94 ± 0.8 | 1.1 ± 0 | 95.4 ± 5 | 97.7 ± 1.1 | 103.1 ± 2 |
| 42YM | 83.4 ± 0.2 | 20.2 ± 1 | 99.8 ± 3 | 100.3 ± 2.6 | 100.4 ± 2.5 |
| 41LM42YM | 88.5 ± 0.4 | 81.2 ± 4 | 103.4 ± 1.7 | 102.2 ± 4.7 | 99.2 ± 9.6 |
| 37EM | 16.8 ± 1.4 | 1 ± 0.1 | 19.8 ± 0.5 | | |
| 37EM39PQ42YM | 7.5 ± 0.9 | 103.3 ± 7 | 99.3 ± 1.3 | | |
| 37EM39PQ41LV42YM | 2.4 ± 0.3 | 102.9 ± 2.4 | 103.7 ± 3 | | |
| 37EV | 7.9 ± 1.1 | 0.6 ± 0 | 40.3 ± 4.2 | | |
| 37EV39PQ | 0.5 ± 0.1 | 93.2 ± 1.4 | 96.7 ± 0.1 | | |
| 37EV39PQ42YM | 0.2 ± 0.1 | 97.8 ± 0.8 | 95.5 ± 3.5 | | |
| 37EV39PQ41LV42YM | 0.1 ± 0 | 92.5 ± 1.8 | 97.4 ± 0.2 | | |
| 37EV39PQ41LT42YM | 4.6 ± 0.9 | 93 ± 2.2 | 95.4 ± 0.2 | | |
| 37EF | 81.3 ± 0.1 | 1.6 ± 0.2 | 6.4 ± 1.2 | | |
| 37EF39PQ | 24.1 ± 3.8 | 96.6 ± 3.1 | 100 ± 2.2 | | |
| 37EF39PQ42YM | 10.4 ± 1 | 99.5 ± 4.7 | 101.6 ± 1.3 | | |
| 37EF39PQ41LV42YM | 11.8 ± 1.2 | 100 ± 8 | 100 ± 3.7 | | |
| 37EW | 86.7 ± 1.4 | 2.8 ± 0.3 | 25.9 ± 2.3 | | |
| 37EW39PQ | 51.8 ± 1.4 | 94.5 ± 2.6 | 100.2 ± 0.1 | | |
| 37EW39PQ42YM | 40.7 ± 0 | 103.2 ± 3.4 | 103.1 ± 3.9 | | |
| 37EW39PQ1LV42YM | 40.8 ± 3 | 99.6 ± 8.6 | 101.2 ± 2 | | |
| 37EI | 94.1 ± 1.8 | 3.1 ± 0.9 | 100.1 ± 12.1 | | |
| 37EI39PQ | 43.8 ± 1.6 | 94.2 ± 1.2 | 96.4 ± 0.2 | | |
| 37EI39PQ42YM | 2.4 ± 0.2 | 93.6 ± 1.8 | 96.6 ± 2.4 | | |
| 37EI39PQ41LV42YM | 16.4 ± 1.2 | 99.2 ± 1.6 | 98.1 ± 0.3 | | |
| 37EH | 61 ± 1.8 | 0.7 ± 0.1 | 2.2 ± 0.5 | | |
| 37EH39PQ | 3.1 ± 0.2 | 76.5 ± 2.7 | 99.2 ± 0.9 | | |
| 37EH39PQ42YM | 15.7 ± 0.7 | 94.7 ± 0.8 | 98.6 ± 1.7 | | |
| 37EH39PQ41LV42YM | 15.5 ± 1.8 | 99.7 ± 1.9 | 101.8 ± 4.4 | | |
| 37ER | 7 ± 0.6 | 0.8 ± 0.1 | 22.6 ± 2.3 | | |
| 37ER39PQ | 0.3 ± 0.1 | 95.6 ± 0.8 | 95.8 ± 3.3 | | |
| 37ER39PQ41LV42YM | 0.1 ± 0.1 | 95.3 ± 1.9 | 95.6 ± 1.8 | | |

TABLE 3

| Tet Repressor | tet Operator | |
|---|---|---|
| | 4C | 6C |
| 37ES39PQ41LI42YF | 17.2 ± 1.1 | 83.1 ± 0.7 |
| 37ES39PQ41LA42YF | 31.3 ± 1 | |
| 37ES39PQ41LP42YW | 29.8 ± 0.5 | |
| 37EA | 8.5 ± 0.5 | 20.4 ± 0.3 |
| 37EA39PQ | 1.5 ± 0.1 | 94.5 ± 5.1 |
| 37EA39PQ42YM | 1.6 ± 0.3 | 92.6 ± 1.4 |
| 37EA39PQ41LV42YM | 1.4 ± 0.2 | 98.3 ± 1.4 |
| 37EA39PQ41LM42YI | 47.7 ± 9.2 | |

TABLE 3-continued

| Tet Repressor | tet Operator 4C | tet Operator 6C |
|---|---|---|
| 37EA39PQ41LA42YL | 17.4 ± 0.5 | |
| 37EA39PQ41LA42YW | 24.9 ± 0.4 | |
| 37EA39PQ41LW42YF | 38.5 ± 0.5 | |
| 37EV39PQ41LV42YC | 8.3 ± 0.2 | |
| 37EV39PQ41LI42YL | 26.9 ± 0.5 | |
| 37EV39PQ41LM42YL | 26.3 ± 0.3 | |
| 37ER39PQ41LV42YL | 22.7 ± 0.3 | |
| 39ER39PQ41LM42YL | 20.9 ± 0.8 | |
| 37ER39PQ41LA42YW | 35.9 ± 1.7 | |
| 37ER39PQ41LI42YL | 21.8 ± 1.6 | |
| 37EK | 7.2 ± 0.4 | 20.8 ± 0.3 |
| 37EK39PQ | 2.2 ± 0.5 | 101.3 ± 0.4 |
| 37EK39PQ42YF | 10.8 ± 0.4 | |
| 37EK39PQ41LT42YM | 2 ± 0.1 | 103.4 ± 3 |
| 37EK39PQ41LW | 10.2 ± 0.3 | |
| 37E139PQ41LF42YM | 60.3 ± 0.5 | |
| 37EQ | 14.5 ± 0.1 | 13.2 ± 0.8 |
| 37EQ39PQ | 2.7 ± 0.3 | 102.7 ± 1.6 |
| 37EQ39PQ42YM | 6.1 ± 0.2 | 104.3 ± 2.3 |
| 37EQ39PQ41LT42YM | 21.2 ± 0.6 | |
| 37EG | 89.8 ± 0.5 | |
| 37EG39PQ | 78.8 ± 0.6 | |
| 37EG39PQ42YM | 70.8 ± 1.5 | |
| 37EG39PQ41LV42YM | 64.9 ± 1.1 | |
| 37EP | 97.5 ± 7.2 | |
| 37EP39PQ | 87.1 ± 4.8 | |
| 37EP39PQ42YM | 64.6 ± 1.2 | |
| 37ED | 96.8 ± 6.1 | |
| 37ED39PQ | 106.2 ± 1.9 | |
| 37ED39PQ41LV42YM | 88.2 ± 1.8 | |
| 37EC | 15.3 ± 0.3 | |
| 37EC39PQ41LA42YM | 1.1 ± 0.1 | |
| 37EY | 88.8 ± 1.3 | |
| 37EY39PQ41LA42YM | 16.8 ± 1.4 | |
| 37EN | 102.2 ± 8.5 | |
| 37EN39PQ | 47.9 ± 0.5 | |
| 39PQ42YM | 71.1 ± 1.8 | |
| 39PQ41LV42YM | 49.4 ± 1.2 | |

The results shown in Tables 2 and 3 demonstrate that the DBD-mutant TetR having only the 39PQ mutation cannot bind the wild-type (4T) tetO sequence (β-galactosidase activity remains at approximately 96%, compared to 100% activity in the absence of the TetR). Furthermore, a series of mutants having, in addition to the 39PQ mutation, further mutations at positions 37, 41 and/or 42 were identified that had the following characteristics 1) an ability to efficiently bind to the "4C" tetO variant and 2) an inability to bind to the "6C" tetO variant. Such mutants that could inhibit expression of a 4C tetO-linked reporter gene by at least 90% (i.e., β-galactosidase activity is less than or equal to 10%) are indicated in bold type in Tables 2 and 3 above. These mutants include: 37ES39PQ, 37ES39PQ42YM, 37ES39PQ41LV42YM, 37ES39PQ41LI42YM, 37ET39PQ, 37ET39PQ42YM, 37ET39PQ41LV, 37ET39PQ41LV42YM, 37EL39PQ42YM, 37EL39PQ41LM42YM, 37EM39PQ42YM, 37EM39PQ41LV42YM, 37EV39PQ, 37EV39PQ42YM, 37EV39PQ41LV42YM, 37EV39PQ41LT42YM, 37EI39PQ42YM, 39EH39PQ, 37ER39PQ, 37ER39PQ41LV42YM, 37EA39PQ, 37PQ42YM, 37EA39PQ41LV42YM, 37EK39PQ, 37EK39PQ41LT42YM, 37EQ39PQ, and 37EQ39PQ42YM. Even more preferred mutants that could inhibit expression of a 4C tetO-linked reporter gene by at least 98% (i.e., β-galactosidase activity is less than or equal to 2%) are indicated in bold type and underlined in Tables 2 and 3 above. These mutants include: 37ES39PQ41LV42YM, 37ES39PQ41LI42YM, 37ET39PQ42YM, 37ET39PQ41LV42YM, 37EL39PQ41LM42YM, 37EV39PQ, 37EV39PQ42YM, 37EV39PQ4LV42YM, 37ER39PQ, 37ER39PQ41LV42YM, 37EA39PQ, 37EA39PQ42YM, 37EA39PQ41LV42YM and 37EK39PQ41LT42YM.

In a second series of experiments, a preferred three-position mutation identified above, 37EA39PQ42YM, was chosen for further analysis. The binding specificities of one- and two-position mutants (i.e., 37EA, 42YM, 37EA39PQ and 37EA42YM) were compared to the three-position mutant (37EA39PQ42YM) using an expanded series of tetO variants having nucleotide substitutions at either the 3, 4, 5 or 6 position. The results of these studies are summarized below in Tables 4 and 5.

TABLE 4

| | tetR Allele | | | | | | |
|---|---|---|---|---|---|---|---|
| tetO2 | EA37 | | EA37PQ39 | | EA37PQ39YM42 | | WT |
| wt | 0 ± 0 | < | 67 ± 2 | | 102 ± 0 | | 0 ± 0 |
| 3C | 6.1 ± 1.2 | < | 88 ± 4 | < | 104 ± 3 | > | 45 ± 1 |
| 3G | 54 ± 1 | < | 99 ± 3 | – | 114 ± 11 | – | 98 ± 2 |
| 3T | 31 ± 2 | < | 99 ± 1 | – | 108 ± 7 | > | 76 ± 3 |
| 4A | 0.3 ± 0.1 | < | 74 ± 1 | < | 92 ± 3 | > | 6.0 ± 0.5 |
| 4C | 0.5 ± 0.1 | | 0 ± 0 | | 0 ± 0 | < | 31 ± 2 |
| 4G | 16 ± 1 | < | 83 ± 0 | < | 96 ± 1 | > | 69 ± 2 |
| 5C | 2.6 ± 0.6 | < | 16 ± 0 | < | 55 ± 0 | > | 1.6 ± 0.1 |
| 5G | 46 ± 2 | < | 104 ± 2 | – | 100 ± 4 | – | 94 ± 2 |
| 5T | 0.4 ± 0.1 | < | 103 ± 3 | – | 109 ± 3 | > | 5.3 ± 1.3 |
| 6A | 0 ± 0 | < | 100 ± 5 | – | 105 ± 0 | > | 0.1 ± 0 |
| 6C | 6 ± 0 | < | 102 ± 2 | – | 101 ± 1 | > | 18 ± 1 |
| β-Galactosidase Activity in [%] | | | | | | | |

TABLE 5

| | tetR Allele | | | | |
|---|---|---|---|---|---|
| tetO2 | EA37 | YM42 | EA37YM42 | | WT |
| wt | 0 ± 0 | 4.4 ± 1.4 | 0 ± 0 | | 0 ± 0 |
| 3C | 6.1 ± 1.2 | 98 ± 2 | – | 98 ± 5 | > | 45 ± 1 |
| 3G | 54 ± 1 | 101 ± 2 | – | 106 ± 3 | – | 98 ± 2 |
| 3T | 31 ± 2 | 102 ± 2 | – | 109 ± 2 | > | 76 ± 3 |
| 4A | 0.3 ± 0.1 | 68 ± 5 | – | 4.1 ± 0.1 | < | 6.0 ± 0.5 |
| 4C | 0.5 ± 0.1 | 60 ± 4 | > | 0.2 ± 0.1 | < | 31 ± 2 |
| 4G | 16 ± 1 | 91 ± 1 | – | 32 ± 1 | < | 69 ± 2 |
| 5C | 2.6 ± 0.6 | 48 ± 3 | > | 1.2 ± 0 | – | 1.6 ± 0.1 |
| 5G | 46 ± 2 | 101 ± 2 | – | 105 ± 2 | – | 94 ± 2 |
| 5T | 0.4 ± 0.1 | 80 ± 3 | – | 0.3 ± 0 | < | 5.3 ± 1.3 |
| 6A | 0 ± 0 | 60 ± 0 | – | 21 ± 2 | > | 0.1 ± 0 |
| 6C | 6 ± 0 | 93 ± 1 | – | 48 ± 0 | > | 18 ± 1 |
| β-Galactosidase Activity in [%] | | | | | |

The results of this analysis indicate that some of the one- and two-positions mutants, while retaining the ability to bind the 4C variant (like the three-position variant), have a broader binding specificity than the three-position variant. For example, 37EA42YM efficiently inhibits β-galactosidase activity of the 4C variant (0.2% activity), but also inhibits the activity of the 4A variant (4.1% activity), the 5C variant (1.2% activity) and the 5T variant (0.3% activity). In contrast, 37EA39PQ42YM efficiently inhibits β-galactosidase activity of the 4C variant (0% activity), but does not efficiently inhibit the activity of the 4A variant (92% activity), the 5C variant (55% activity) or the 5T variant (109% activity).

In a third series of experiments, a panel of TetR mutants having a substitution at positions 43 and/or 44, alone or together with additional mutations at positions 37, 40 and/or 41, were made and tested as described above. The results of these analyses are summarized below in Table 6.

TABLE 6

| Operator Variant | 6C | wt | 4C | 6A | 5G |
|---|---|---|---|---|---|
| pWH1201 (Control) | 100% ± 6 | 100% ± 7 | 100% ± 6 | 100% ± 7 | 100% ± 3 |
| pWH520 (WT TetR) | 24% ± 1 | 0.2% ± 0.1 | 38% ± 3 | 0% ± 0.2 | 5% ± 1 |
| 43WR | 68% ± 2 | 103% ± 3 | 95% ± 1 | 94% ± 3 | 90% ± 2 |
| 44HA | 101% ± 2 | 91% ± 6 | 104% ± 5 | 96% ± 2 | 105% ± 3 |
| 43WR44HA | 28% ± 0.5 | 105% ± 7 | 102% ± 4 | 91% ± 2 | 90% ± 7 |
| 41LI43WR44HA | 35% ± 1.5 | 101% ± 2 | 93% ± 3 | 97% ± 4 | 93% ± 1 |
| 44HV | 97% ± 3 | 87% ± 2 | 107% ± 5 | 97% ± 2 | 106% ± 7 |
| 43WR44HV | 36% ± 1.8 | 101% ± 3 | 95% ± 3 | 91% ± 4 | 97% ± 3 |
| 41LI43WR44HV | 23% ± 1 | 96% ± 4 | 94% ± 4 | 83% ± 6 | 92% ± 4 |
| 40TR41LI43WR44HV | 27% ± 1 | 105% ± 4 | 94% ± 3 | 92% ± 5 | 91% ± 4 |
| 41LI43WR44HT | 25% ± 1 | 100% ± 3 | 97% ± 2 | 96% ± 2 | 94% ± 3 |
| 37ES | 10% ± 0.3 | 0% ± 0.1 | 1.7% ± 0.2 | 0% ± 0 | 0% ± 0.1 |
| 37ES43WR44HN | 3.8% ± 0.3 | 80% ± 3 | 97% ± 5 | 104% ± 3 | 92% ± 3 |
| 37ES43WR44HV | 5.5% ± 0.2 | 56% ± 2 | 94% ± 3 | 80% ± 3 | 92% ± 0.5 |
| 41LV43WR44HV | 87% ± 2 | 102% ± 2 | 93% ± 3 | 108% ± 3 | 95% ± 3 |
| 37ES41LV43WR44HV | 24% ± 0.7 | 77% ± 4 | 92% ± 3 | 103% ± 3 | 97% ± 1 |

The results shown in Table 6 demonstrate that DBD-mutant TetRs having an ability to efficiently bind to the "6C" tetO variant but an inability to bind efficiently to the "4C" tetO variant can be identified. Mutants that could inhibit expression of a 6C tetO-linked reporter gene by at least 94% (i.e., β-galactosidase activity is less than or equal to 6%) are indicated in bold type in Table 6 above. The two preferred mutants are 37ES43WR44HN (only 3.8% activity with the 6C variant but 97% activity with the 4C variant) and 37ES43WR44HV (only 5.5% activity with the 6C variant but 94% activity with the 4C variant). The most preferred mutant is 37ES43WR44HN.

B. Use of tTA and tTA$^R$ Transactivators With Different tetO Binding Specificities to Regulate Gene Expression in Cells Tet repressor mutants having different DNA binding specificities, as described above in Part A, were used to construct expression vectors encoding modified transactivator fusion proteins. One modified construct encoded a TetR having the DBD mutations 37EA39PQ42YM in an otherwise wild-type sequence, fused to VP16. This construct is referred to as tTA$_4$. This construct binds to the 4C tetO variant but not the 6C tetO variant and is regulated by Tc in the same manner as a wild-type TetR. Thus, this tTA$_4$ transactivator binds to 4C tetO sequences (but not 6C tetO sequences) in the absence, but not the presence, of Tc. Another modified construct encoded a TetR having the DBD mutations ES37WR43HN44, which confer the ability to bind the 6C tetO variant but not the 4C tetO variant, and, additionally, the mutations 71EK95DN101 LS102GD, which confer the "reverse" Tc-regulated phenotype, fused to VP16. This construct is referred to as tTA$^R_6$. Thus, this tTA$^R_6$ construct binds to 6C tetO sequences (but not 4C tetO sequences) in the presence, but not the absence, of Tc.

Furthermore, the tetO-linked luciferase reporter gene construct PhCMV*-1 was modified to contain either the 4C or the 6C mutation. These modified reporter gene constructs are referred to herein as tetO$_{C4}$ and tetO$_{C6}$, respectively.

To examine the ability of the tTA$_4$ and tTA$^R_6$ expression constructs to regulate expression of the tetO$_{C4}$ and tet$_{C6}$ reporter gene constructs within cells, various combinations of transactivator expression constructs and reporter gene constructs were cotransfected into HeLa cells in transient transfection assays. The luciferase activity in cell extracts prepared from transfected cells cultured either in the presence or absence of doxycycline was then examined. Representative results are illustrated graphically in FIG. 13.

Figure 13:
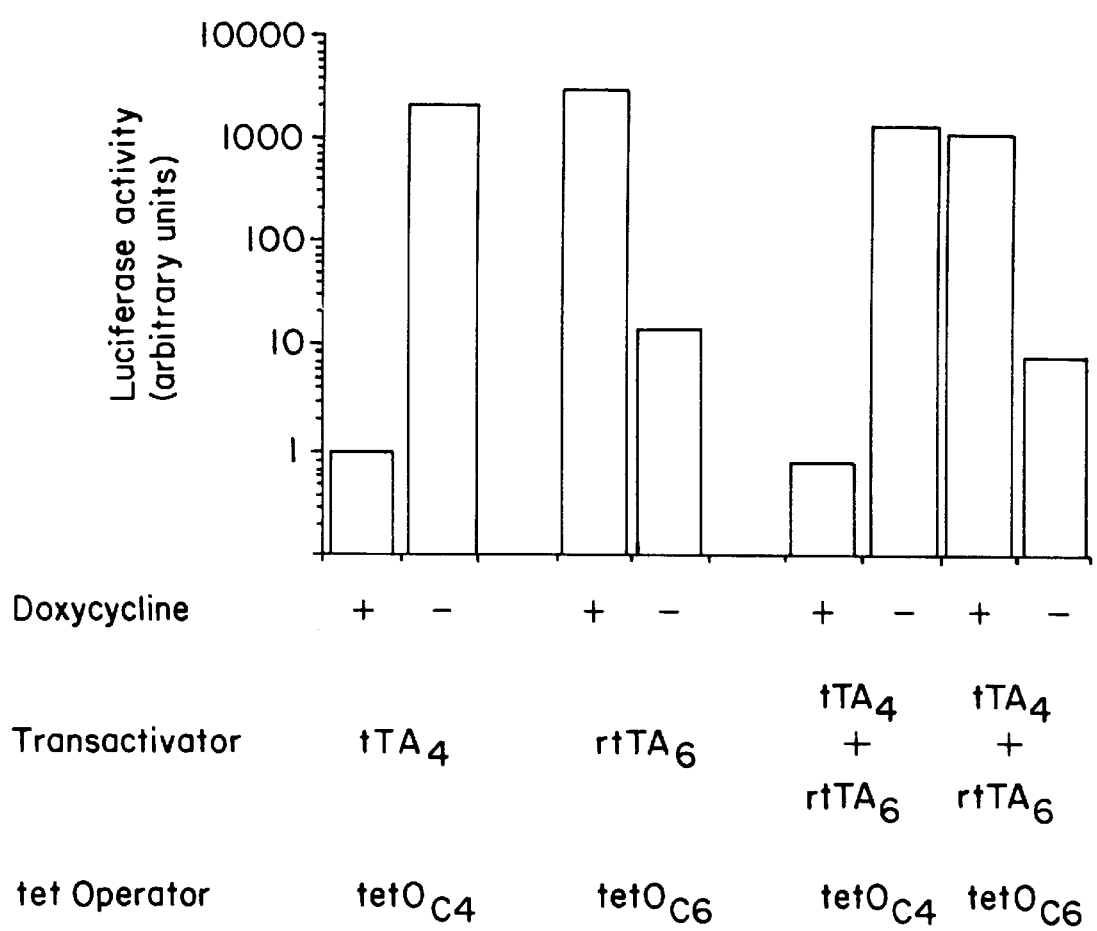
FIG. 13 is a graphic representation of luciferase activity in cells cotransfected with a tTA$_4$ transactivator construct and a tetO$_{C4}$ luciferase reporter gene in the presence or absence of doxycycline (first pair of columns), a tTA$^R_6$ transactivator construct and a tetO$_{C6}$ luciferase reporter gene in the presence or absence of doxycycline (second pair of columns), tTA$_4$ and tTA$^R_6$ transactivator constructs and tetOC4 luciferase reporter gene in the presence or absence of doxycycline (third pair of columns) or tTA$_4$ and tTA$^R_6$ transactivator constructs and tetO$_{C6}$ luciferase reporter gene in the presence or absence of doxycycline (fourth pair of columns).

The first pair of bars in FIG. 13 demonstrate that tTA$_4$ efficiently regulates expression of tetO$_{C4}$ (i.e., low luciferase activity in the presence of doxycycline but ~1000-fold increase in luciferase activity in the absence of doxycycline). The second pair of bars in FIG. 13 demonstrate that tTA$^R_6$ efficiently regulates expression of tetO$_{C6}$ (i.e., low luciferase activity in the absence of doxycycline but ~100-fold increase in luciferase activity in the presence of doxycycline). Finally, the third and fourth pairs of bars in FIG. 13 demonstrate that when both the tTA$_4$ and tTA$^R_6$ constructs are introduced into a single host cell, their binding specificity for their respective operators, tetO$_{C4}$ and tetOc$_6$, is maintained (i.e., they do not exhibit crossactivation of a non-target tetO sequence). Thus, when tTA$_4$ and tTA$^R_6$ are both introduced into cells together with the tetO$_{C4}$ reporter gene, expression of the reporter gene is regulated in a manner identical to when tTA$_4$ alone is introduced into the cell (i.e., high luciferase activity only in the absence of doxycycline). Similarly, when tTA$_4$ and tTA$^R_6$ are both introduced into cells together with the tetOc$_6$ reporter gene, expression of the reporter gene is regulated in a manner identical to when tTA$^R_6$ alone is introduced into the cell (i.e., high luciferase activity only in the presence of doxycycline). Additionally, when tTA$_4$ alone is cotransfected with tetO$_{C6}$ or tTA$^R_6$ alone is cotransfected with tetO$_{C4}$ no effect of the transactivators is observed. These various results demonstrate the strict DNA binding specificty of the tTA$_4$ and tTA$^R_6$ fusion proteins and, moreover, demonstrate that the DNA binding specificity of an unfused DBD-mutated Tet repressor is maintained when the DBD-mutated Tet repressor is incorporated into a transcriptional activator fusion protein.

C. Dimerization Specificity of Different Classes of Tet Repressors

Tet repressors can be placed into seven different classes called A to E, G and H. Each repressor protein typically recognizes its operator sequences as a dimer. To establish an efficient combination regulatory system, in which two (or more) Tc-regulated fusion proteins are introduced into the same cell, it may be preferable to use classes of TetR that do not heterodimerize with each other (e.g., a transactivator fusion protein of one class and a transcriptional inhibitor fusion protein of another class). To determine the dimerization specificity of TetRs of different classes, in vitro dimerization assays were performed. In this assay, two purified TetR which are distinguishable by their electrophoretic mobilities are mixed in a solution to avoid oxidation of the proteins and incubated for ten minutes at 50° C., followed by a 30 minute incubation at 4° C. The protein mixture is then analyzed by native polyacrylamide gel electrophoresis.

A deletion mutant of the Tn10-encoded class B TetR (Δ26-53) was used as one protein in the mixture. This deletion mutant has an increased electrophoretic mobility compared to the full-length class B, C, D or E repressors tested. Thus, heterodimers between the deletion mutant and a full-length TetR can be detected by PAGE. When the class B deletion mutant was incubated with either a full-length class B TetR or a full-length class C tetR, heterodimers between the deletion mutant and the full-length repressor were observed. In contrast, when the class B deletion mutant was incubated with either a full-length class D TetR or a full-length class E TetR, no heterodimer between the deletion mutant and the fulllength repressor were observed.

To confirm these in vitro findings, in vivo transdominance experiments were performed. In these assays, a TetR expression construct was introduced into an *E. coli* strain that carries a tetO-linked β-galactosidase reporter gene, either alone or together with an expression construct for the class B TetR deletion mutant described above (Δ26-53), and β-galactosidase activity was measured. In this assay, the level of β-galactosidase activity in the absence of any TetR constructs was standardized as 100%. The presence of a full-length TetR construct alone results in decreased β-galactosidase activity. When a full-length TetR and the deletion construct are coexpressed in the cells, the deletion mutant cannot bind to tetO sequences itself but, if it is able to heterodimerize with the full-length TetR, the deletion mutant will reduce the ability of the full-length TetR to repress β-gal activity. Thus, if the deletion mutant and the full-length TetR heterodimerize, β-gal activity is higher in the presence of the deletion mutant than in the absence of the deletion mutant. The results of these experiments are summarized below in Table 7.

TABLE 7

| Tet Repressor | Level of TetR Expression | % β-galactosidase activity −Δ26–53 | % β-galactosidase activity +Δ26–53 | Factor of Transdominance |
|---|---|---|---|---|
| none | — | 100 | 100 | — |
| wt class B | low | 1.7(±0.6) | 37.3(±3.5) | 22 |
| wt class B | high | 1.2(±0.2) | 2.4(±0.1) | 2 |
| wt class C | low | 84.5(±1.3) | 100.6 (±5.1) | 1.2 |
| wt class C | high | 6.4(±0.0) | 12.8(±1.2) | 2 |
| wt class D | low | 62.2(13.5) | 65.4(±2.0) | 1.1 |
| wt class D | high | 1.4(±0.0) | 1.5(±0.0) | 1.1 |
| wt class E | low | 40.5(±1.2) | 41.1(±3.8) | 1.0 |
| wt class E | high | 1.2(±0.1) | 1.2(±0.1) | 1.0 |

The results shown in Table 7 confirm that the full-length class B TetR and the class B deletion mutant can heterodimerize (e.g., at low levels of TetR expression, β-galactosidase activity increases 22-fold in the presence of the deletion mutant). Similarly, these experiments indicate that the class B deletion mutant can heterodimerize with the full-length class C TetR (e.g., at high levels of TetR expression, β-galactosidase activity increases 2-fold in the presence of the deletion mutant). In contrast, no evidence of heterodimerization between the class B deletion mutant and either the full-length class D or class E TetR was observed To confirm that results shown in Table 7 were not simply a specific effect due to the particular deletion mutant used, similar experiments were performed with two additional deletions mutants (TetR(B)Δ9-11 and TetR(B)Δ83-87). Similar results were observed with the two additional deletion mutants, confirming that the lack of heterodimerization between class B TetR and either class D TetR or class E TetR was a general phenomenon that did not depend on which particular deletion mutant was used.

Thus, based on in vitro and in vivo assays, a class B TetR does not efficiently heterodimerize with either a class D TetR or a class E TetR.

D. Model Regulatory Systems for Combination Regulation of Genes

Figure 14A:
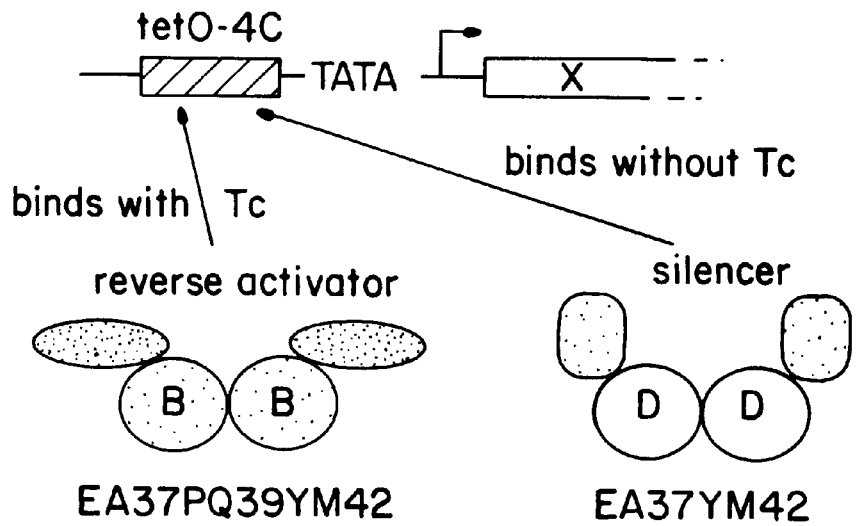
FIGS. 14A–B are schematic diagrams of model regulatory systems for coordinate regulation of one gene in a cell using a reverse activator and a silencer (FIG. 14A) or independent regulation of two genes in a cell using an activator and a reverse activator (FIG. 14B).
Figure 14B:
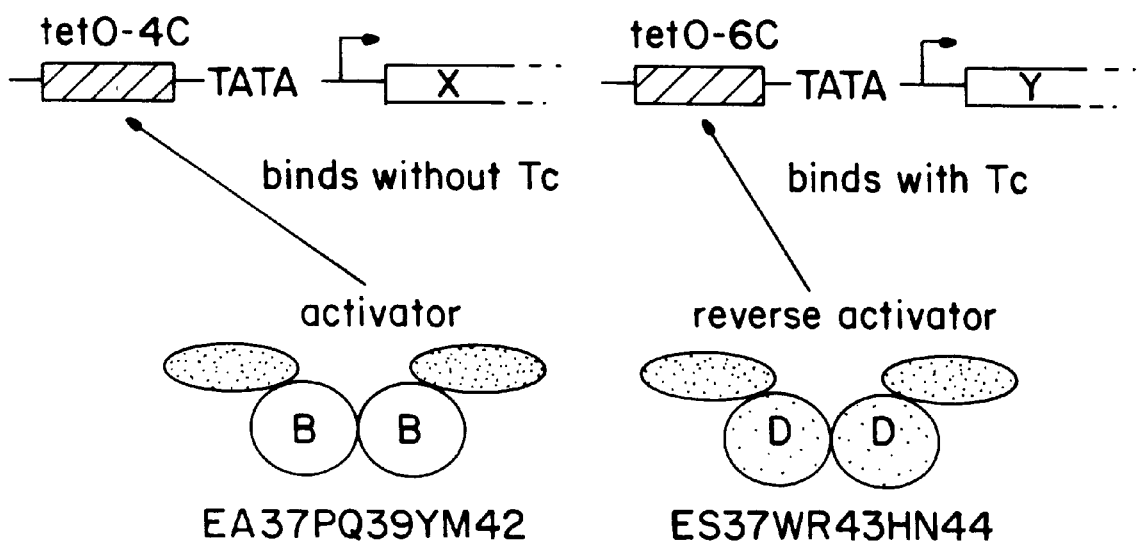

The results discussed in the preceding sections can be combined to create preferred model schemes for various combinatorial regulatory systems. In the first combinatorial regulatory system, a single gene is coordinately regulated by a reverse transactivator fusion protein and a transcriptional inhibitor fusion protein. This scheme is illustrated in FIG. 14, Model A. In this system, at least one tetO-4C variant sequence is operatively linked to a minimal promoter (containg a "TATA" motif) and a gene of interest ("X"). Regulation of gene X in a cell is mediated, in part, by a "reverse activator" composed of a class B TetR having the DBD mutations 37EA39PQ42YM, which confer the ability to bind the 4C variant, and, additionally, the mutations 71EK95DN101LS102GD, which confer the "reverse" Tc-regulated phenotype, fused to VP16. Thus, this reverse activator binds to tetO-4C in the presence of Tc to thereby stimulate expression of the gene of interest. Regulation of the gene is also mediated, in part, by a "silencer" composed of a class D TetR having the DBD mutations 37EAYM42, which confer the ability to bind the 4C variant but also the ability to bind a broader spectrum of operator sequences than the triple DBD mutation of the reverse transactivator, fused to a silencer domain, e.g., from v-erbA or Drosophila Krueppel. Thus, this silencer binds to tetO-4C in the absence of Tc to thereby inhibit expression of gene X. Based on the results in Part C above, the class B TetR-containing reverse transactivator and the class D TetR-containing silencer will not heterodimerize. The combined use of the reverse transactivator and the silencer to regulate the gene of interest has the advantage that expression of the gene of interest is highly repressed by the silencer in the absence of Tc but is efficiently stimulated by the reverse transactivator in the presence of Tc.

In the second combinatorial regulatory system, two genes in the same cell are independently regulated by a transactivator fusion protein and a reverse transactivator fusion protein. This scheme is illustrated in FIG. 14, Model B. In this system, at least one tetO4C variant sequence is operatively linked to a minimal promoter ("TATA") and a first gene of interest ("X"). Additionally, at least one tetO-6C variant sequence is operatively linked to a minimal promoter ("TATA") and a second gene of interest ("Y"). Regulation of gene X in a cell is accomplished using an "activator" composed of a class B TetR having the DBD mutations 37EA39PQ42YM, which confer the ability to bind the 4C variant, in an otherwise wild-type sequence, fused to VP16. Thus, this activator binds to tetO-4C in the absence (but not the presence) of Tc to thereby stimulate expression of gene X. Regulation of gene Y in the cell is accomplished using a "reverse activator" composed of a class D TetR having the DBD mutations 37ESWR43HN44, which confer the ability to bind the 6C variant, and, additionally, the mutations 71EK95DN101LS102GD, which confer the "reverse" Tc-regulated phenotype, fused to VP16. Thus, this reverse activator binds to tetO-6C in the presence of Tc to thereby stimulate expression of gene Y. Based on the results in Part C above, the class B TetR-containing transactivator and the class D TetR-containing reverse transactivator will not heterodimerize. This combinatorial regulatory system thus allows for stimulation of one gene of interest in a cell in the absence of Tc and stimulation of another gene of interest in the same cell in the presence of Tc.

Equivalents

Those skilled in the art will recognize, or be able to ascertain using no more than routine experimentation, many equivalents to the specific embodiments of the invention described herein. Such equivalents are intended to be encompassed by the following claims.

SEQUENCE LISTING (1) GENERAL INFORMATION:

(iii) NUMBER OF SEQUENCES: 37

(2) INFORMATION FOR SEQ ID NO: 1:

(i) SEQUENCE CHARACTERISTICS:
       (A) LENGTH: 1008 base pairs
       (B) TYPE: nucleic acid
       (C) STRANDEDNESS: double
       (D) TOPOLOGY: linear (ii) MOLECULE TYPE: DNA (ix) FEATURE:
       (A) NAME/KEY: exon
       (B) LOCATION: 1..1008

(ix) FEATURE:
       (A) NAME/KEY: mRNA
       (B) LOCATION: 1..1008

(ix) FEATURE:
       (A) NAME/KEY: misc. binding
       (B) LOCATION: 1..207

(ix) FEATURE:
       (A) NAME/KEY: misc. binding
       (B) LOCATION: 208..335

(ix) FEATURE:
       (A) NAME/KEY: CDS
       (B) LOCATION: 1..1005

(xi) SEQUENCE DESCRIPTION: SEQ ID NO: 1:

```
ATG TCT AGA TTA GAT AAA AGT AAA GTG ATT AAC AGC GCA TTA GAG CTG      48
Met Ser Arg Leu Asp Lys Ser Lys Val Ile Asn Ser Ala Leu Glu Leu
 1               5                  10                  15

CTT AAT GAG GTC GGA ATC GAA GGT TTA ACA ACC CGT AAA CTC GCC CAG      96
Leu Asn Glu Val Gly Ile Glu Gly Leu Thr Thr Arg Lys Leu Ala Gln
             20                  25                  30

AAG CTA GGT GTA GAG CAG CCT ACA CTG TAT TGG CAT GTA AAA AAT AAG     144
Lys Leu Gly Val Glu Gln Pro Thr Leu Tyr Trp His Val Lys Asn Lys
         35                  40                  45

CGG GCT TTG CTC GAC GCC TTA GCC ATT GAG ATG TTA GAT AGG CAC CAT     192
Arg Ala Leu Leu Asp Ala Leu Ala Ile Glu Met Leu Asp Arg His His
     50                  55                  60

ACT CAC TTT TGC CCT TTA AAA GGG GAA AGC TGG CAA GAT TTT TTA CGC     240
Thr His Phe Cys Pro Leu Lys Gly Glu Ser Trp Gln Asp Phe Leu Arg
 65                  70                  75                  80

AAT AAG GCT AAA AGT TTT AGA TGT GCT TTA CTA AGT CAT CGC AAT GGA     288
Asn Lys Ala Lys Ser Phe Arg Cys Ala Leu Leu Ser His Arg Asn Gly
                 85                  90                  95

GCA AAA GTA CAT TCA GAT ACA CGG CCT ACA GAA AAA CAG TAT GAA ACT     336
Ala Lys Val His Ser Asp Thr Arg Pro Thr Glu Lys Gln Tyr Glu Thr
            100                 105                 110

CTC GAA AAT CAA TTA GCC TTT TTA TGC CAA CAA GGT TTT TCA CTA GAG     384
Leu Glu Asn Gln Leu Ala Phe Leu Cys Gln Gln Gly Phe Ser Leu Glu
        115                 120                 125

AAT GCA TTA TAT GCA CTC AGC GCT GTG GGG CAT TTT ACT TTA GGT TGC     432
Asn Ala Leu Tyr Ala Leu Ser Ala Val Gly His Phe Thr Leu Gly Cys
    130                 135                 140

GTA TTG GAA GAT CAA GAG CAT CAA GTC GCT AAA GAA GAA AGG GAA ACA     480
Val Leu Glu Asp Gln Glu His Gln Val Ala Lys Glu Glu Arg Glu Thr
145                 150                 155                 160
```

```
CCT ACT ACT GAT AGT ATG CCG CCA TTA TTA CGA CAA GCT ATC GAA TTA      528
Pro Thr Thr Asp Ser Met Pro Pro Leu Leu Arg Gln Ala Ile Glu Leu
                165                 170                 175

TTT GAT CAC CAA GGT GCA GAG CCA GCC TTC TTA TTC GGC CTT GAA TTG      576
Phe Asp His Gln Gly Ala Glu Pro Ala Phe Leu Phe Gly Leu Glu Leu
            180                 185                 190

ATC ATA TGC GGA TTA GAA AAA CAA CTT AAA TGT GAA AGT GGG TCC GCG      624
Ile Ile Cys Gly Leu Glu Lys Gln Leu Lys Cys Glu Ser Gly Ser Ala
        195                 200                 205

TAC AGC CGC GCG CGT ACG AAA AAC AAT TAC GGG TCT ACC ATC GAG GGC      672
Tyr Ser Arg Ala Arg Thr Lys Asn Asn Tyr Gly Ser Thr Ile Glu Gly
    210                 215                 220

CTG CTC GAT CTC CCG GAC GAC GAC GCC CCC GAA GAG GCG GGG CTG GCG      720
Leu Leu Asp Leu Pro Asp Asp Asp Ala Pro Glu Glu Ala Gly Leu Ala
225                 230                 235                 240

GCT CCG CGC CTG TCC TTT CTC CCC GCG GGA CAC ACG CGC AGA CTG TCG      768
Ala Pro Arg Leu Ser Phe Leu Pro Ala Gly His Thr Arg Arg Leu Ser
                245                 250                 255

ACG GCC CCC CCG ACC GAT GTC AGC CTG GGG GAC GAG CTC CAC TTA GAC      816
Thr Ala Pro Pro Thr Asp Val Ser Leu Gly Asp Glu Leu His Leu Asp
            260                 265                 270

GGC GAG GAC GTG GCG ATG GCG CAT GCC GAC GCG CTA GAC GAT TTC GAT      864
Gly Glu Asp Val Ala Met Ala His Ala Asp Ala Leu Asp Asp Phe Asp
        275                 280                 285

CTG GAC ATG TTG GGG GAC GGG GAT TCC CCG GGT CCG GGA TTT ACC CCC      912
Leu Asp Met Leu Gly Asp Gly Asp Ser Pro Gly Pro Gly Phe Thr Pro
    290                 295                 300

CAC GAC TCC GCC CCC TAC GGC GCT CTG GAT ATG GCC GAC TTC GAG TTT      960
His Asp Ser Ala Pro Tyr Gly Ala Leu Asp Met Ala Asp Phe Glu Phe
305                 310                 315                 320

GAG CAG ATG TTT ACC GAT CCC CTT GGA ATT GAC GAG TAC GGT GGG TAG     1008
Glu Gln Met Phe Thr Asp Pro Leu Gly Ile Asp Glu Tyr Gly Gly
                325                 330                 335

(2) INFORMATION FOR SEQ ID NO: 2:

(i) SEQUENCE CHARACTERISTICS:
        (A) LENGTH: 335 amino acids
        (B) TYPE: amino acid
        (D) TOPOLOGY: linear (ii) MOLECULE TYPE: protein (xi) SEQUENCE DESCRIPTION: SEQ ID NO: 2:

Met Ser Arg Leu Asp Lys Ser Lys Val Ile Asn Ser Ala Leu Glu Leu
  1               5                  10                  15

Leu Asn Glu Val Gly Ile Glu Gly Leu Thr Thr Arg Lys Leu Ala Gln
                 20                  25                  30

Lys Leu Gly Val Glu Gln Pro Thr Leu Tyr Trp His Val Lys Asn Lys
             35                  40                  45

Arg Ala Leu Leu Asp Ala Leu Ala Ile Glu Met Leu Asp Arg His His
         50                  55                  60

Thr His Phe Cys Pro Leu Lys Gly Glu Ser Trp Gln Asp Phe Leu Arg
 65                  70                  75                  80

Asn Lys Ala Lys Ser Phe Arg Cys Ala Leu Leu Ser His Arg Asn Gly
                 85                  90                  95

Ala Lys Val His Ser Asp Thr Arg Pro Thr Glu Lys Gln Tyr Glu Thr
                100                 105                 110

Leu Glu Asn Gln Leu Ala Phe Leu Cys Gln Gln Gly Phe Ser Leu Glu
```

```
            115                 120                 125
Asn Ala Leu Tyr Ala Leu Ser Ala Val Gly His Phe Thr Leu Gly Cys
        130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
                180                 185                 190

Ile Ile Cys Gly Leu Glu Lys Gln Leu Lys Cys Glu Ser Gly Ser Ala
                195                 200                 205

Tyr Ser Arg Ala Arg Thr Lys Asn Asn Tyr Gly Ser Thr Ile Glu Gly
210                 215                 220

Leu Leu Asp Leu Pro Asp Asp Ala Pro Glu Glu Ala Gly Leu Ala
225                 230                 235                 240

Ala Pro Arg Leu Ser Phe Leu Pro Ala Gly His Thr Arg Arg Leu Ser
                245                 250                 255

Thr Ala Pro Pro Thr Asp Val Ser Leu Gly Asp Glu Leu His Leu Asp
                260                 265                 270

Gly Glu Asp Val Ala Met Ala His Ala Asp Ala Leu Asp Asp Phe Asp
                275                 280                 285

Leu Asp Met Leu Gly Asp Gly Asp Ser Pro Gly Pro Gly Phe Thr Pro
290                 295                 300

His Asp Ser Ala Pro Tyr Gly Ala Leu Asp Met Ala Asp Phe Glu Phe
305                 310                 315                 320

Glu Gln Met Phe Thr Asp Pro Leu Gly Ile Asp Glu Tyr Gly Gly
                325                 330                 335

(2) INFORMATION FOR SEQ ID NO: 3:

(i) SEQUENCE CHARACTERISTICS:
        (A) LENGTH: 33 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO: 3:

GAC GCG CTA GAC GAT TTC GAT CTG GAC ATG TTG                      33
Asp Ala Leu Asp Asp Phe Asp Leu Asp Met Leu
1               5                   10

(2) INFORMATION FOR SEQ ID NO: 4:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 4:

Asp Ala Leu Asp Asp Phe Asp Leu Asp Met Leu
1               5                   10

(2) INFORMATION FOR SEQ ID NO: 5:

(i) SEQUENCE CHARACTERISTICS:
```

(A) LENGTH: 7 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 5:

Met Pro Lys Arg Pro Arg Pro
1               5

(2) INFORMATION FOR SEQ ID NO: 6:

(i) SEQUENCE CHARACTERISTICS:
        (A) LENGTH: 569 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO: 6:

GAATTCGGGG CCGCGGAGGC TGGATCGGTC CCGGTGTCTT CTATGGAGGT CAAAACAGCG      60

TGGATGGCGT CTCCAGGCGA TCTGACGGTT CACTAAACGA GCTCTGCTTA TATAGGTCG      120

GTTTACCACT CCCTATCAGT GATAGAGAAA AGTGAAAGTC GAGTTTACCA CTCCCTATC      180

GTGATAGAGA AAAGTGAAAG TCGAGTTTAC CACTCCCTAT CAGTGATAGA GAAAAGTGA      240

AGTCGAGTTT ACCACTCCCT ACCAGTGATA GAGAAAAGTG AAAGTCGAGT TTACCACTC      300

CTATCAGTGA TAGAGAAAAG TGAAAGTCGA GTTTACCACT CCCTATCAGT GATAGAGAA      360

AGTGAAAGTC GAGTTTACCA CTCCCTATCA GTGATAGAGA AAAGTGAAAG TCGAGCTCG      420

TACCCGGGTC GAGTAGGCGT GTACGGTGGG AGGCCTATAT AAGCAGAGCT CGTTTAGTG      480

ACCGTCAGAT CGCCTGGAGA CGCCATCCAC GCTGTTTTGA CCTCCATAGA AGACACCGG      540

ACCGATCCAG CCTCCGCGGC CCCGAATTC                                       569

(2) INFORMATION FOR SEQ ID NO: 7:

(i) SEQUENCE CHARACTERISTICS:
        (A) LENGTH: 520 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO: 7:

AGATCTGCAG GGTCGCTCGG TGTTCGAGGC CACACGCGTC ACCTTAATAT GCGAAGTGGA      60

CCGGATCTCG AGTTTACCAC TCCCTATCAG TGATAGAGAA AAGTGAAAGT CGAGTTTAC      120

ACTCCCTATC AGTGATAGAG AAAAGTGAAA GTCGAGTTTA CCACTCCCTA TCAGTGATA      180

AGAAAAGTGA AGTCGAGTT TACCACTCCC TATCAGTGAT AGAGAAAAGT GAAAGTCGA      240

TTACCACTC CCTATCAGTG ATAGAGAAAA GTGAAAGTCG AGTTTACCAC TCCCTATCA      300

TGATAGAGAA AAGTGAAAGT CGAGTTTACC ACTCCCTATC AGTGATAGAG AAAAGTGAA      360

GTCGAGCTCG GTACCCGGGT CGAGTAGGCG TGTACGGTGG GAGGCCTATA TAAGCAGAG      420

TCGTTTAGTG AACCGTCAGA TCGCCTGGAG ACGCCATCCA CGCTGTTTTG ACCTCCATA      480

AAGACACCGG GACCGATCCA GCCTCCGCGG CCCCGAATTC                           520

(2) INFORMATION FOR SEQ ID NO: 8:

(i) SEQUENCE CHARACTERISTICS:
    (A) LENGTH: 450 base pairs
    (B) TYPE: nucleic acid
    (C) STRANDEDNESS: double
    (D) TOPOLOGY: linear (ii) MOLECULE TYPE: DNA (genomic)

(vi) ORIGINAL SOURCE:
    (A) ORGANISM: Human cytomegalovirus
    (B) STRAIN: K12, Towne (ix) FEATURE:
    (A) NAME/KEY: mRNA
    (B) LOCATION: 382..450

(xi) SEQUENCE DESCRIPTION: SEQ ID NO: 8:

GAATTCCTCG AGTTTACCAC TCCCTATCAG TGATAGAGAA AAGTGAAAGT CGAGTTTACC        60

ACTCCCTATC AGTGATAGAG AAAAGTGAAA GTCGAGTTTA CCACTCCCTA TCAGTGATA       120

AGAAAAGTGA AAGTCGAGTT TACCACTCCC TATCAGTGAT AGAGAAAAGT GAAAGTCGA       180

TTTACCACTC CCTATCAGTG ATAGAGAAAA GTGAAAGTCG AGTTTACCAC TCCCTATCA       240

TGATAGAGAA AAGTGAAAGT CGAGTTTACC ACTCCCTATC AGTGATAGAG AAAAGTGAA       300

GTCGAGCTCG GTACCCGGGT CGAGTAGGCG TGTACGGTGG GAGGCCTATA TAAGCAGAG       360

TCGTTTAGTG AACCGTCAGA TCGCCTGGAG ACGCCATCCA CGCTGTTTTG ACCTCCATA       420

AAGACACCGG GACCGATCCA GCCTCCGCGG                                      450

(2) INFORMATION FOR SEQ ID NO: 9:

(i) SEQUENCE CHARACTERISTICS:
        (A) LENGTH: 450 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Human cytomegalovirus
        (B) STRAIN: Towne (ix) FEATURE:
        (A) NAME/KEY: mRNA
        (B) LOCATION: 382..450

(xi) SEQUENCE DESCRIPTION: SEQ ID NO: 9:

GAATTCCTCG ACCCGGGTAC CGAGCTCGAC TTTCACTTTT CTCTATCACT GATAGGGAGT        60

GGTAAACTCG ACTTTCACTT TTCTCTATCA CTGATAGGGA GTGGTAAACT CGACTTTCA       120

TTTTCTCTAT CACTGATAGG GAGTGGTAAA CTCGACTTTC ACTTTTCTCT ATCACTGAT       180

GGGAGTGGTA AACTCGACTT TCACTTTTCT CTATCACTGA TAGGGAGTGG TAAACTCGA       240

TTTCACTTTT CTCTATCACT GATAGGGAGT GGTAAACTCG ACTTTCACTT TTCTCTATC       300

CTGATAGGGA GTGGTAAACT CGAGTAGGCG TGTACGGTGG GAGGCCTATA TAAGCAGAG       360

TCGTTTAGTG AACCGTCAGA TCGCCTGGAG ACGCCATCCA CGCTGTTTTG ACCTCCATA       420

AAGACACCGG GACCGATCCA GCCTCCGCGG                                      450

(2) INFORMATION FOR SEQ ID NO: 10:

(i) SEQUENCE CHARACTERISTICS:
        (A) LENGTH: 398 base pairs
        (B) TYPE: nucleic acid
        (C) STRANDEDNESS: double (D) TOPOLOGY: linear (ii) MOLECULE TYPE: DNA (genomic)

(vi) ORIGINAL SOURCE:
        (A) ORGANISM: Herpes Simplex Virus
        (B) STRAIN: KOS (xi) SEQUENCE DESCRIPTION: SEQ ID NO: 10:

```
GAGCTCGACT TTCACTTTTC TCTATCACTG ATAGGGAGTG GTAAACTCGA CTTTCACTTT      60

TCTCTATCAC TGATAGGGAG TGGTAAACTC GACTTTCACT TTTCTCTATC ACTGATAGG      120

AGTGGTAAAC TCGACTTTCA CTTTTCTCTA TCACTGATAG GGAGTGGTAA ACTCGACTT      180

CACTTTTCTC TATCACTGAT AGGGAGTGGT AAACTCGACT TTCACTTTTC TCTATCACT      240

ATAGGGAGTG GTAAACTCGA CTTTCACTTT TCTCTATCAC TGATAGGGAG TGGTAAACT      300

GAGATCCGGC GAATTCGAAC ACGCAGATGC AGTCGGGGCG GCGCGGTCCG AGGTCCACT      360

CGCATATTAA GGTGACGCGT GTGGCCTCGA ACACCGAG                             398
```

(2) INFORMATION FOR SEQ ID NO: 11:

(i) SEQUENCE CHARACTERISTICS:
        (A) LENGTH: 38 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO: 11:

```
ACTTTATCAC TGATAAACAA ACTTATCAGT GATAAAGA                              38
```

(2) INFORMATION FOR SEQ ID NO: 12:

(i) SEQUENCE CHARACTERISTICS:
        (A) LENGTH: 38 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO: 12:

```
ACTCTATCAT TGATAGAGTT CCCTATCAGT GATAGAGA                              38
```

(2) INFORMATION FOR SEQ ID NO: 13:

(i) SEQUENCE CHARACTERISTICS:
        (A) LENGTH: 38 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO: 13:

```
AGCTTATCAT CGATAAGCTA GTTTATCACA GTTAAATT                              38
```

(2) INFORMATION FOR SEQ ID NO: 14:

(i) SEQUENCE CHARACTERISTICS:
        (A) LENGTH: 38 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO: 14:

ACTCTATCAT TGATAGGGAA CTCTATCAAT GATAGGGA                                38

(2) INFORMATION FOR SEQ ID NO: 15:

(i) SEQUENCE CHARACTERISTICS:
        (A) LENGTH: 38 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO: 15:

AATCTATCAC TGATAGAGTA CCCTATCATC GATAGAGA                                38

(2) INFORMATION FOR SEQ ID NO: 16:

(i) SEQUENCE CHARACTERISTICS:
        (A) LENGTH: 621 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 16:

```
ATG TCT AGA TTA GAT AAA AGT AAA GTG ATT AAC AGC GCA TTA GAG CTG       48
Met Ser Arg Leu Asp Lys Ser Lys Val Ile Asn Ser Ala Leu Glu Leu
 1               5                  10                  15

CTT AAT GAG GTC GGA ATC GAA GGT TTA ACA ACC CGT AAA CTC GCC CAG       96
Leu Asn Glu Val Gly Ile Glu Gly Leu Thr Thr Arg Lys Leu Ala Gln
             20                  25                  30

AAG CTA GGT GTA GAG CAG CCT ACA TTG TAT TGG CAT GTA AAA AAT AAG      144
Lys Leu Gly Val Glu Gln Pro Thr Leu Tyr Trp His Val Lys Asn Lys
         35                  40                  45

CGG GCT TTG CTC GAC GCC TTA GCC ATT GAG ATG TTA GAT AGG CAC CAT      192
Arg Ala Leu Leu Asp Ala Leu Ala Ile Glu Met Leu Asp Arg His His
     50                  55                  60

ACT CAC TTT TGC CCT TTA GAA GGG GAA AGC TGG CAA GAT TTT TTA CGT      240
Thr His Phe Cys Pro Leu Glu Gly Glu Ser Trp Gln Asp Phe Leu Arg
 65                  70                  75                  80

AAT AAG GCT AAA AGT TTT AGA TGT GCT CTA CTA AGT CAT CGC GAT GGA      288
Asn Lys Ala Lys Ser Phe Arg Cys Ala Leu Leu Ser His Arg Asp Gly
                 85                  90                  95

GCA AAA GTA CAT TTA GGT ACA CGG CCT ACA GAA AAA CAG TAT GAA ACT      336
Ala Lys Val His Leu Gly Thr Arg Pro Thr Glu Lys Gln Tyr Glu Thr
            100                 105                 110

CTC GAA AAT CAA TTA GCC TTT TTA TGC CAA CAA GGT TTT TCA CTA GAG      384
Leu Glu Asn Gln Leu Ala Phe Leu Cys Gln Gln Gly Phe Ser Leu Glu
        115                 120                 125

AAT GCA TTA TAT GCA CTC AGC GCT GTG GGG CAT TTT ACT TTA GGT TGC      432
Asn Ala Leu Tyr Ala Leu Ser Ala Val Gly His Phe Thr Leu Gly Cys
    130                 135                 140

GTA TTG GAA GAT CAA GAG CAT CAA GTC GCT AAA GAA GAA AGG GAA ACA      480
Val Leu Glu Asp Gln Glu His Gln Val Ala Lys Glu Glu Arg Glu Thr
145                 150                 155                 160

CCT ACT ACT GAT AGT ATG CCG CCA TTA TTA CGA CAA GCT ATC GAA TTA      528
Pro Thr Thr Asp Ser Met Pro Pro Leu Leu Arg Gln Ala Ile Glu Leu
                165                 170                 175

TTT GAT CAC CAA GGT GCA GAG CCA GCC TTC TTA TTC GGC CTT GAA TTG      576
Phe Asp His Gln Gly Ala Glu Pro Ala Phe Leu Phe Gly Leu Glu Leu
```

```
                  180                 185                 190
ATC ATA TGC GGA TTA GAA AAA CAA CTT AAA TGT GAA AGT GGG TCC           621
Ile Ile Cys Gly Leu Glu Lys Gln Leu Lys Cys Glu Ser Gly Ser
            195                 200                 205
```

(2) INFORMATION FOR SEQ ID NO: 17:

(i) SEQUENCE CHARACTERISTICS:
        (A) LENGTH: 207 amino acids
        (B) TYPE: amino acid
        (D) TOPOLOGY: linear (ii) MOLECULE TYPE: protein (xi) SEQUENCE DESCRIPTION: SEQ ID NO: 17:

```
Met Ser Arg Leu Asp Lys Ser Lys Val Ile Asn Ser Ala Leu Glu Leu
 1               5                  10                  15

Leu Asn Glu Val Gly Ile Glu Gly Leu Thr Thr Arg Lys Leu Ala Gln
                20                  25                  30

Lys Leu Gly Val Glu Gln Pro Thr Leu Tyr Trp His Val Lys Asn Lys
            35                  40                  45

Arg Ala Leu Leu Asp Ala Leu Ala Ile Glu Met Leu Asp Arg His His
        50                  55                  60

Thr His Phe Cys Pro Leu Glu Gly Glu Ser Trp Gln Asp Phe Leu Arg
 65                 70                  75                  80

Asn Lys Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser
        195                 200                 205
```

(2) INFORMATION FOR SEQ ID NO: 18:

(i) SEQUENCE CHARACTERISTICS:
        (A) LENGTH: 621 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 18:

```
ATG TCT AGA TTA GAT AAA AGT AAA GTG ATT AAC AGC GCA TTA GAG CTG    48
Met Ser Arg Leu Asp Lys Ser Lys Val Ile Asn Ser Ala Leu Glu Leu
 1               5                  10                  15

CTT AAT GAG GTC GGA ATC GAA GGT TTA ACA ACC CGT AAA CTC GCC CAG    96
Leu Asn Glu Val Gly Ile Glu Gly Leu Thr Thr Arg Lys Leu Ala Gln
                20                  25                  30

AAG CTA GGT GTA GAG CAG CCT ACA CTG TAT TGG CAT GTA AAA AAT AAG   144
```

```
Lys Leu Gly Val Glu Gln Pro Thr Leu Tyr Trp His Val Lys Asn Lys
         35                  40                  45

CGG GCT TTG CTC GAC GCC TTA GCC ATT GAG ATG TTA GAT AGG CAC CAT        192
Arg Ala Leu Leu Asp Ala Leu Ala Ile Glu Met Leu Asp Arg His His
 50                  55                  60

ACT CAC TTT TGC CCT TTA AAA GGG GAA AGC TGG CAA GAT TTT TTA CGC        240
Thr His Phe Cys Pro Leu Lys Gly Glu Ser Trp Gln Asp Phe Leu Arg
 65                  70                  75                  80

AAT AAG GCT AAA AGT TTT AGA TGT GCT TTA CTA AGT CAT CGC AAT GGA        288
Asn Lys Ala Lys Ser Phe Arg Cys Ala Leu Leu Ser His Arg Asn Gly
                 85                  90                  95

GCA AAA GTA CAT TCA GAT ACA CGG CCT ACA GAA AAA CAG TAT GAA ACT        336
Ala Lys Val His Ser Asp Thr Arg Pro Thr Glu Lys Gln Tyr Glu Thr
                100                 105                 110

CTC GAA AAT CAA TTA GCC TTT TTA TGC CAA CAA GGT TTT TCA CTA GAG        384
Leu Glu Asn Gln Leu Ala Phe Leu Cys Gln Gln Gly Phe Ser Leu Glu
            115                 120                 125

AAT GCA TTA TAT GCA CTC AGC GCT GTG GGG CAT TTT ACT TTA GGT TGC        432
Asn Ala Leu Tyr Ala Leu Ser Ala Val Gly His Phe Thr Leu Gly Cys
        130                 135                 140

GTA TTG GAA GAT CAA GAG CAT CAA GTC GCT AAA GAA GAA AGG GAA ACA        480
Val Leu Glu Asp Gln Glu His Gln Val Ala Lys Glu Glu Arg Glu Thr
145                 150                 155                 160

CCT ACT ACT GAT AGT ATG CCG CCA TTA TTA CGA CAA GCT ATC GAA TTA        528
Pro Thr Thr Asp Ser Met Pro Pro Leu Leu Arg Gln Ala Ile Glu Leu
                165                 170                 175

TTT GAT CAC CAA GGT GCA GAG CCA GCC TTC TTA TTC GGC CTT GAA TTG        576
Phe Asp His Gln Gly Ala Glu Pro Ala Phe Leu Phe Gly Leu Glu Leu
                180                 185                 190

ATC ATA TGC GGA TTA GAA AAA CAA CTT AAA TGT GAA AGT GGG TCC            621
Ile Ile Cys Gly Leu Glu Lys Gln Leu Lys Cys Glu Ser Gly Ser
            195                 200                 205

(2) INFORMATION FOR SEQ ID NO: 19:

(i) SEQUENCE CHARACTERISTICS:
        (A) LENGTH: 207 amino acids
        (B) TYPE: amino acid
        (D) TOPOLOGY: linear (ii) MOLECULE TYPE: protein (xi) SEQUENCE DESCRIPTION: SEQ ID NO: 19:

Met Ser Arg Leu Asp Lys Ser Lys Val Ile Asn Ser Ala Leu Glu Leu
 1               5                  10                  15

Leu Asn Glu Val Gly Ile Glu Gly Leu Thr Thr Arg Lys Leu Ala Gln
                20                  25                  30

Lys Leu Gly Val Glu Gln Pro Thr Leu Tyr Trp His Val Lys Asn Lys
         35                  40                  45

Arg Ala Leu Leu Asp Ala Leu Ala Ile Glu Met Leu Asp Arg His His
 50                  55                  60

Thr His Phe Cys Pro Leu Lys Gly Glu Ser Trp Gln Asp Phe Leu Arg
 65                  70                  75                  80

Asn Lys Ala Lys Ser Phe Arg Cys Ala Leu Leu Ser His Arg Asn Gly
                 85                  90                  95

Ala Lys Val His Ser Asp Thr Arg Pro Thr Glu Lys Gln Tyr Glu Thr
                100                 105                 110

Leu Glu Asn Gln Leu Ala Phe Leu Cys Gln Gln Gly Phe Ser Leu Glu
            115                 120                 125
```

```
Asn Ala Leu Tyr Ala Leu Ser Ala Val Gly His Phe Thr Leu Gly Cys
        130                 135                 140

Val Leu Glu Asp Gln Glu His Gln Val Ala Lys Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
                180                 185                 190

Ile Ile Cys Gly Leu Glu Lys Gln Leu Lys Cys Glu Ser Gly Ser
            195                 200                 205
```

(2) INFORMATION FOR SEQ ID NO: 20:

(i) SEQUENCE CHARACTERISTICS:
        (A) LENGTH: 192 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 20:

```
GAC ATG GAA AAA GCG ACA CCG GAG ACG ATG GTC CAT TGG ATT TGT CTG      48
Asp Met Glu Lys Ala Thr Pro Glu Thr Met Val His Trp Ile Cys Leu
 1               5                  10                  15

AAG ATG GAG CCA GCT CTG TGG ATG GCC ATT ACA GCA ACA TCG CAC GGC      96
Lys Met Glu Pro Ala Leu Trp Met Ala Ile Thr Ala Thr Ser His Gly
                20                  25                  30

GCA AGG CAC AGG ACA TTC GTC GGG TTT TCC GGC TGC CTC CAC CGC AAA     144
Ala Arg His Arg Thr Phe Val Gly Phe Ser Gly Cys Leu His Arg Lys
            35                  40                  45

TCC CTC ACG TAC CCA GTG ATA TGC CTG AGC AAA CCG AGC CAG AGG ATT     192
Ser Leu Thr Tyr Pro Val Ile Cys Leu Ser Lys Pro Ser Gln Arg Ile
        50                  55                  60
```

(2) INFORMATION FOR SEQ ID NO: 21:

(i) SEQUENCE CHARACTERISTICS:
        (A) LENGTH: 64 amino acids
        (B) TYPE: amino acid
        (D) TOPOLOGY: linear (ii) MOLECULE TYPE: protein (xi) SEQUENCE DESCRIPTION: SEQ ID NO: 21:

```
Asp Met Glu Lys Ala Thr Pro Glu Thr Met Val His Trp Ile Cys Leu
 1               5                  10                  15

Lys Met Glu Pro Ala Leu Trp Met Ala Ile Thr Ala Thr Ser His Gly
                20                  25                  30

Ala Arg His Arg Thr Phe Val Gly Phe Ser Gly Cys Leu His Arg Lys
            35                  40                  45

Ser Leu Thr Tyr Pro Val Ile Cys Leu Ser Lys Pro Ser Gln Arg Ile
        50                  55                  60
```

(2) INFORMATION FOR SEQ ID NO: 22:

(i) SEQUENCE CHARACTERISTICS:
        (A) LENGTH: 816 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 22:

```
CTG GAC GAC TCG AAG CGC GTA GCC AAG CGG AAG CTG ATC GAG GAG AAC      48
Leu Asp Asp Ser Lys Arg Val Ala Lys Arg Lys Leu Ile Glu Glu Asn
 1               5                  10                  15

CGG GAG CGG CGA CGC AAG GAG GAG ATG ATC AAA TCC CTG CAG CAC CGG      96
Arg Glu Arg Arg Arg Lys Glu Glu Met Ile Lys Ser Leu Gln His Arg
                20                  25                  30

CCC AGC CCC AGC GCA GAG GAG TGG GAG CTG ATC CAC GTG GTG ACC GAG     144
Pro Ser Pro Ser Ala Glu Glu Trp Glu Leu Ile His Val Val Thr Glu
            35                  40                  45

GCG CAC CGC AGC ACC AAC GCG CAG GGC AGC CAC TGG AAG CAG AGG AGG     192
Ala His Arg Ser Thr Asn Ala Gln Gly Ser His Trp Lys Gln Arg Arg
        50                  55                  60

AAA TTC CTG CTC GAA GAT ATC GGT CAG TCG CCC ATG GCC TCC ATG CTT     240
Lys Phe Leu Leu Glu Asp Ile Gly Gln Ser Pro Met Ala Ser Met Leu
 65                  70                  75                  80

GAC GGG GAC AAA GTG GAC CTG GAG GCG TTC AGC GAG TTT ACA AAA ATC     288
Asp Gly Asp Lys Val Asp Leu Glu Ala Phe Ser Glu Phe Thr Lys Ile
                85                  90                  95

ATC ACG CCG GCC ATC ACC CGC GTG GTC GAC TTT GCC AAA AAC CTG CCC     336
Ile Thr Pro Ala Ile Thr Arg Val Val Asp Phe Ala Lys Asn Leu Pro
                100                 105                 110

ATG TTC TCG GAG CTG CCG TGC GAG GAT CAG ATC ATC CTG CTG AAG GGC     384
Met Phe Ser Glu Leu Pro Cys Glu Asp Gln Ile Ile Leu Leu Lys Gly
            115                 120                 125

TGC TGC ATG GAG ATC ATG TCG CTG CGC GCC GCC GTG CGC TAC GAC CCC     432
Cys Cys Met Glu Ile Met Ser Leu Arg Ala Ala Val Arg Tyr Asp Pro
        130                 135                 140

GAG AGC GAA ACG CTG ACG CTG AGC GGG GAA ATG GCC GTC AAA CGC GAG     480
Glu Ser Glu Thr Leu Thr Leu Ser Gly Glu Met Ala Val Lys Arg Glu
145                 150                 155                 160

CAG TTG AAG AAC GGA GGG CTG GGG GTC GTG TCT GAT GCC ATC TTC GAC     528
Gln Leu Lys Asn Gly Gly Leu Gly Val Val Ser Asp Ala Ile Phe Asp
                165                 170                 175

CTC GGC AAG TCG CTG TCT GCC TTC AAC CTG GAC GAC ACC GAG GTG GCC     576
Leu Gly Lys Ser Leu Ser Ala Phe Asn Leu Asp Asp Thr Glu Val Ala
            180                 185                 190

CTG CTG CAG GCC GTG CTC CTC ATG TCC TCA GAC CGG ACG GGG CTG ATC     624
Leu Leu Gln Ala Val Leu Leu Met Ser Ser Asp Arg Thr Gly Leu Ile
        195                 200                 205

TGC GTG GAT AAG ATA GAG AAG TGC CAG GAG TCG TAC CTG CTG GCG TTC     672
Cys Val Asp Lys Ile Glu Lys Cys Gln Glu Ser Tyr Leu Leu Ala Phe
210                 215                 220

GAG CAC TAC ATC AAC TAC CGC AAA CAC AAC ATT CCC CAC TTC TGG TCC     720
Glu His Tyr Ile Asn Tyr Arg Lys His Asn Ile Pro His Phe Trp Ser
225                 230                 235                 240

AAG CTG CTG ATG AAG GTG GCG GAC CTG CGC ATG ATC GGC GCC TAC CAC     768
Lys Leu Leu Met Lys Val Ala Asp Leu Arg Met Ile Gly Ala Tyr His
                245                 250                 255

GCC AGC CGC TTC CTG CAC ATG AAG GTG GAG TGC CCC ACC GAG CTC TCC     816
Ala Ser Arg Phe Leu His Met Lys Val Glu Cys Pro Thr Glu Leu Ser
            260                 265                 270
```

(2) INFORMATION FOR SEQ ID NO: 23:

(i) SEQUENCE CHARACTERISTICS:
        (A) LENGTH: 272 amino acids
        (B) TYPE: amino acid
        (D) TOPOLOGY: linear (ii) MOLECULE TYPE: protein (xi) SEQUENCE DESCRIPTION: SEQ ID NO: 23:

Leu Asp Asp Ser Lys Arg Val Ala Lys Arg Lys Leu Ile Glu Glu Asn
1               5                   10                  15

Arg Glu Arg Arg Arg Lys Glu Glu Met Ile Lys Ser Leu Gln His Arg
                20                  25                  30

Pro Ser Pro Ser Ala Glu Glu Trp Glu Leu Ile His Val Val Thr Glu
            35                  40                  45

Ala His Arg Ser Thr Asn Ala Gln Gly Ser His Trp Lys Gln Arg Arg
        50                  55                  60

Lys Phe Leu Leu Glu Asp Ile Gly Gln Ser Pro Met Ala Ser Met Leu
65                  70                  75                  80

Asp Gly Asp Lys Val Asp Leu Glu Ala Phe Ser Glu Phe Thr Lys Ile
                85                  90                  95

Ile Thr Pro Ala Ile Thr Arg Val Val Asp Phe Ala Lys Asn Leu Pro
            100                 105                 110

Met Phe Ser Glu Leu Pro Cys Glu Asp Gln Ile Ile Leu Leu Lys Gly
            115                 120                 125

Cys Cys Met Glu Ile Met Ser Leu Arg Ala Ala Val Arg Tyr Asp Pro
        130                 135                 140

Glu Ser Glu Thr Leu Thr Leu Ser Gly Glu Met Ala Val Lys Arg Glu
145                 150                 155                 160

Gln Leu Lys Asn Gly Gly Leu Gly Val Val Ser Asp Ala Ile Phe Asp
                165                 170                 175

Leu Gly Lys Ser Leu Ser Ala Phe Asn Leu Asp Asp Thr Glu Val Ala
            180                 185                 190

Leu Leu Gln Ala Val Leu Leu Met Ser Ser Asp Arg Thr Gly Leu Ile
        195                 200                 205

Cys Val Asp Lys Ile Glu Lys Cys Gln Glu Ser Tyr Leu Leu Ala Phe
        210                 215                 220

Glu His Tyr Ile Asn Tyr Arg Lys His Asn Ile Pro His Phe Trp Ser
225                 230                 235                 240

Lys Leu Leu Met Lys Val Ala Asp Leu Arg Met Ile Gly Ala Tyr His
                245                 250                 255

Ala Ser Arg Phe Leu His Met Lys Val Glu Cys Pro Thr Glu Leu Ser
            260                 265                 270

(2) INFORMATION FOR SEQ ID NO: 24:

(i) SEQUENCE CHARACTERISTICS:
        (A) LENGTH: 25 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO: 24:

TCCCCGGGTA ACTAAGTAAG GATCC                                             25

(2) INFORMATION FOR SEQ ID NO: 25:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO: 25:

AGTGGGTCCC CGGGTGACAT GGAA                                              24

(2) INFORMATION FOR SEQ ID NO: 26:

(i) SEQUENCE CHARACTERISTICS:
            (A) LENGTH: 8 amino acids
            (B) TYPE: amino acid
            (D) TOPOLOGY: linear (ii) MOLECULE TYPE: polypeptide (v) FRAGMENT TYPE: internal (xi) SEQUENCE DESCRIPTION: SEQ ID NO: 26:

Ser Gly Ser Pro Gly Asp Met Glu
 1               5

(2) INFORMATION FOR SEQ ID NO: 27:

(i) SEQUENCE CHARACTERISTICS:
            (A) LENGTH: 24 base pairs
            (B) TYPE: nucleic acid
            (C) STRANDEDNESS: double
            (D) TOPOLOGY: linear (ii) MOLECULE TYPE: DNA (xi) SEQUENCE DESCRIPTION: SEQ ID NO: 27:

AGTGGGTCCC CGGGTCTGGA CGAC                                              24

(2) INFORMATION FOR SEQ ID NO: 28:

(i) SEQUENCE CHARACTERISTICS:
            (A) LENGTH: 8 amino acids
            (B) TYPE: amino acid
            (D) TOPOLOGY: linear (ii) MOLECULE TYPE: polypeptide (v) FRAGMENT TYPE: internal (xi) SEQUENCE DESCRIPTION: SEQ ID NO: 28:

Ser Gly Ser Pro Gly Leu Asp Asp
 1               5

(2) INFORMATION FOR SEQ ID NO: 29:

(i) SEQUENCE CHARACTERISTICS:
            (A) LENGTH: 207 amino acids
            (B) TYPE: amino acid
            (D) TOPOLOGY: linear (ii) MOLECULE TYPE: protein (xi) SEQUENCE DESCRIPTION: SEQ ID NO: 29:

Met Ser Arg Leu Asp Lys Ser Lys Val Ile Asn Ser Ala Leu Glu Leu
 1               5                  10                  15

Leu Asn Glu Val Gly Ile Glu Gly Leu Thr Thr Arg Lys Leu Ala Gln
                20                  25                  30

Lys Leu Gly Val Glu Gln Pro Thr Leu Tyr Trp His Val Lys Asn Lys
            35                  40                  45

Arg Ala Leu Leu Asp Ala Leu Ala Ile Glu Met Leu Asp Arg His His
        50                  55                  60

Thr His Phe Cys Pro Leu Glu Gly Glu Ser Trp Gln Asp Phe Leu Arg

```
                    65                  70                  75                  80
Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
            115                 120                 125

Asn Ala Leu Tyr Ala Leu Ser Ala Val Gly His Phe Thr Leu Gly Cys
            130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
                180                 185                 190

Ile Ile Cys Gly Leu Glu Lys Gln Leu Lys Cys Glu Ser Gly Ser
                195                 200                 205
```

(2) INFORMATION FOR SEQ ID NO: 30:

(i) SEQUENCE CHARACTERISTICS:
        (A) LENGTH: 218 amino acids
        (B) TYPE: amino acid
        (D) TOPOLOGY: linear (ii) MOLECULE TYPE: protein (xi) SEQUENCE DESCRIPTION: SEQ ID NO: 30:

```
Met Ala Arg Leu Asn Arg Glu Ser Val Ile Asp Ala Ala Leu Gly Leu
1                   5                  10                  15

Leu Asn Glu Thr Gly Ile Asp Glu Leu Thr Thr Arg Lys Leu Ala Gln
                20                  25                  30

Lys Leu Gly Ile Glu Gln Pro Thr Leu Tyr Trp His Val Lys Asn Lys
            35                  40                  45

Arg Ala Leu Leu Asp Ala Leu Ala Val Glu Ile Leu Ala Arg His His
50                  55                  60

Asp Tyr Ser Leu Pro Ala Ala Gly Glu Ser Trp Gln Ser Phe Leu Arg
65                  70                  75                  80

Asn Asn Ala Met Ser Phe Arg Arg Ala Leu Leu Arg Tyr Arg Asp Gly
                85                  90                  95

Ala Lys Val His Leu Gly Thr Arg Pro Asp Glu Lys Gln Tyr Asp Thr
            100                 105                 110

Val Glu Thr Gln Leu Arg Phe Met Thr Glu Asn Gly Phe Ser Leu Arg
            115                 120                 125

Asp Gly Leu Tyr Ala Ile Ser Ala Val Ser His Phe Thr Leu Gly Ala
            130                 135                 140

Val Leu Glu Gln Gln Glu His Thr Ala Ala Leu Thr Asp Arg Pro Ala
145                 150                 155                 160

Ala Pro Asp Glu Asn Leu Pro Pro Leu Leu Arg Glu Ala Leu Gln Ile
                165                 170                 175

Met Asp Ser Asp Asp Gly Glu Gln Ala Phe Leu His Gly Leu Glu Ser
            180                 185                 190

Leu Ile Arg Gly Phe Glu Val Gln Leu Thr Ala Leu Leu Gln Ile Val
            195                 200                 205

Gly Gly Asp Lys Leu Ile Ile Pro Phe Cys
210                 215
```

(2) INFORMATION FOR SEQ ID NO: 31:

(i) SEQUENCE CHARACTERISTICS:
        (A) LENGTH: 216 amino acids
        (B) TYPE: amino acid
        (D) TOPOLOGY: linear (ii) MOLECULE TYPE: protein (xi) SEQUENCE DESCRIPTION: SEQ ID NO: 31:

```
Met Thr Lys Leu Gln Pro Asn Thr Val Ile Arg Ala Ala Leu Asp Leu
 1               5                  10                  15

Leu Asn Glu Val Gly Val Asp Gly Leu Thr Thr Arg Lys Leu Ala Glu
                20                  25                  30

Arg Leu Gly Val Gln Gln Pro Ala Leu Tyr Trp His Phe Arg Asn Lys
             35                  40                  45

Arg Ala Leu Leu Asp Ala Leu Ala Glu Ala Met Leu Ala Glu Asn His
         50                  55                  60

Thr His Ser Val Pro Arg Ala Asp Asp Trp Arg Ser Phe Leu Ile
 65                  70                  75                  80

Gly Asn Ala Arg Ser Phe Arg Gln Ala Leu Leu Ala Tyr Arg Asp Gly
                 85                  90                  95

Ala Arg Ile His Ala Gly Thr Arg Pro Gly Ala Pro Gln Met Glu Thr
                100                 105                 110

Ala Asp Ala Gln Leu Arg Phe Leu Cys Glu Ala Gly Phe Ser Ala Gly
             115                 120                 125

Asp Ala Val Asn Ala Leu Met Thr Ile Ser Tyr Phe Thr Val Gly Ala
130                 135                 140

Val Leu Glu Glu Gln Ala Gly Asp Ser Glu Ser Gly Glu Arg Gly Gly
145                 150                 155                 160

Thr Val Glu Gln Ala Pro Leu Ser Pro Leu Leu Arg Ala Ala Ile Asp
                165                 170                 175

Ala Phe Asp Glu Ala Gly Pro Asp Ala Ala Phe Glu Gln Gly Leu Ala
                180                 185                 190

Val Ile Val Asp Gly Leu Ala Lys Arg Arg Leu Val Val Arg Asn Val
                195                 200                 205

Glu Gly Pro Arg Lys Gly Asp Asp
210                 215
```

(2) INFORMATION FOR SEQ ID NO: 32:

(i) SEQUENCE CHARACTERISTICS:
        (A) LENGTH: 219 amino acids
        (B) TYPE: amino acid
        (D) TOPOLOGY: linear (ii) MOLECULE TYPE: protein (xi) SEQUENCE DESCRIPTION: SEQ ID NO: 32:

```
Met Asn Lys Leu Gln Arg Glu Ala Val Ile Arg Thr Ala Leu Gly Leu
 1               5                  10                  15

Leu Asn Asp Val Gly Met Glu Gly Leu Thr Thr Arg Arg Leu Ala Glu
                20                  25                  30

Arg Leu Gly Val Gln Gln Pro Ala Leu Tyr Trp His Phe Lys Asn Lys
             35                  40                  45

Arg Ala Leu Leu Asp Ala Leu Ala Glu Ala Met Leu Thr Ile Asn His
         50                  55                  60
```

```
Thr His Ser Thr Pro Arg Asp Asp Asp Trp Arg Ser Phe Leu Lys
 65                  70                  75                  80

Gly Asn Ala Cys Ser Phe Arg Arg Ala Leu Leu Ala Tyr Arg Asp Gly
                 85                  90                  95

Ala Arg Ile His Ala Gly Thr Arg Pro Ala Ala Pro Gln Met Glu Lys
                100                 105                 110

Ala Asp Ala Gln Leu Arg Phe Leu Cys Asp Ala Gly Phe Ser Ala Gly
                115                 120                 125

Asp Ala Thr Tyr Ala Leu Met Ala Ile Ser Tyr Phe Thr Val Gly Ala
    130                 135                 140

Val Leu Glu Gln Gln Ala Ser Glu Ala Asp Ala Glu Glu Arg Gly Glu
145                 150                 155                 160

Asp Gln Leu Thr Thr Ser Ala Ser Thr Met Pro Ala Arg Leu Gln Ser
                165                 170                 175

Ala Met Lys Ile Val Tyr Glu Ala Gly Pro Asp Ala Ala Phe Glu Arg
                180                 185                 190

Gly Leu Ala Leu Ile Ile Gly Gly Leu Glu Lys Met Arg Leu Thr Thr
                195                 200                 205

Asn Asp Ile Glu Val Leu Lys Asn Val Asp Glu
    210                 215
```

(2) INFORMATION FOR SEQ ID NO: 33:

(i) SEQUENCE CHARACTERISTICS:
        (A) LENGTH: 210 amino acids
        (B) TYPE: amino acid
        (D) TOPOLOGY: linear (ii) MOLECULE TYPE: protein (xi) SEQUENCE DESCRIPTION: SEQ ID NO: 33:

```
Met Thr Lys Leu Asp Lys Gly Thr Val Ile Ala Ala Gly Leu Glu Leu
 1               5                  10                  15

Leu Asn Glu Val Gly Met Asp Ser Leu Thr Thr Arg Lys Leu Ala Glu
                20                  25                  30

Arg Leu Lys Val Gln Gln Pro Ala Leu Tyr Trp His Phe Gln Asn Lys
                35                  40                  45

Arg Ala Leu Leu Asp Ala Leu Pro Glu Ala Met Leu Arg Glu Arg His
    50                  55                  60

Thr Arg Ser Leu Pro Glu Glu Asn Glu Asp Trp Arg Val Phe Leu Lys
 65                  70                  75                  80

Glu Asn Ala Leu Ser Phe Arg Thr Ala Leu Leu Ser Tyr Arg Asp Gly
                 85                  90                  95

Ala Arg Ile His Ala Gly Thr Arg Pro Thr Glu Pro Asn Phe Gly Thr
                100                 105                 110

Ala Glu Thr Gln Ile Arg Phe Leu Cys Ala Glu Gly Phe Cys Pro Lys
                115                 120                 125

Arg Ala Val Trp Ala Leu Arg Ala Val Ser His Tyr Val Val Gly Ser
    130                 135                 140

Val Leu Glu Gln Gln Ala Ser Asp Ala Asp Glu Arg Val Pro Asp Arg
145                 150                 155                 160

Pro Asp Val Ser Glu Gln Ala Pro Ser Ser Phe Leu His Val Leu Phe
                165                 170                 175

His Glu Leu Glu Thr Asp Gly Met Asp Ala Ala Phe Asn Phe Gly Leu
                180                 185                 190

Asp Ser Leu Ile Ala Gly Phe Glu Arg Leu Arg Ala Ala Val Leu Ala
```

195             200             205

Thr Asp
210

(2) INFORMATION FOR SEQ ID NO: 34:

(i) SEQUENCE CHARACTERISTICS:
        (A) LENGTH: 211 amino acids
        (B) TYPE: amino acid
        (D) TOPOLOGY: linear (ii) MOLECULE TYPE: protein (xi) SEQUENCE DESCRIPTION: SEQ ID NO: 34:

Met Ala Arg Leu Ser Leu Asp Asp Val Ile Ser Met Ala Leu Thr Leu
1               5                   10                  15

Leu Asp Ser Glu Gly Leu Glu Gly Leu Thr Thr Arg Lys Leu Ala Gln
            20                  25                  30

Ser Leu Lys Ile Glu Gln Pro Thr Leu Tyr Trp His Val Arg Asn Lys
        35                  40                  45

Gln Thr Leu Met Asn Met Leu Ser Glu Ala Ile Leu Ala Lys His His
    50                  55                  60

Thr Arg Ser Ala Pro Leu Pro Thr Glu Ser Trp Gln Gln Phe Leu Gln
65                  70                  75                  80

Glu Asn Ala Leu Ser Phe Arg Lys Ala Leu Leu Val His Arg Asp Gly
                85                  90                  95

Ala Arg Leu His Ile Gly Thr Ser Pro Thr Pro Gln Phe Glu Gln
            100                 105                 110

Ala Glu Ala Gln Leu Arg Cys Leu Cys Asp Ala Gly Phe Ser Val Glu
        115                 120                 125

Glu Ala Leu Phe Ile Leu Gln Ser Ile Ser His Phe Thr Leu Gly Ala
    130                 135                 140

Val Leu Glu Glu Gln Ala Thr Asn Gln Ile Glu Asn Asn His Val Ile
145                 150                 155                 160

Asp Ala Ala Pro Pro Leu Leu Gln Glu Ala Phe Asn Ile Gln Ala Arg
                165                 170                 175

Thr Ser Ala Glu Met Ala Phe His Phe Gly Leu Lys Ser Leu Ile Phe
            180                 185                 190

Gly Phe Ser Ala Gln Leu Asp Glu Lys Lys His Thr Pro Ile Glu Asp
        195                 200                 205

Gly Asn Lys
    210

(2) INFORMATION FOR SEQ ID NO: 35:

(i) SEQUENCE CHARACTERISTICS:
        (A) LENGTH: 819 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 35:

AGTTCTATGT CTAGATTAGA TAAAAGTAAA GTGATTAACA GCGCATTAGA GCTGCTTAAT    60

GAGGTCGGAA TCGAAGGTTT AACAACCCGT AAACTCGCCC AGAAGCTAGG TGTAGAGCA    120

CCTACATTGT ATTGGCATGT AAAAAATAAG CGGGCTTTGC TCGACGCCTT AGCCATTGA    180

ATGTTAGATA GGCACCATAC TCACTTTTGC CCTTTAGAAG GGGAAAGCTG GCAAGATTT    240

```
TTACGTAATA AGGCTAAAAG TTTTAGATGT GCTTTACTAA GTCATCGCGA TGGAGCAAA      300

GTACATTTAG GTACACGGCC TACAGAAAAA CAGTATGAAA CTCTCGAAAA TCAATTAGC      360

TTTTTATGCC AACAAGGTTT TCACTAGAG AATGCATTAT ATGCACTCAG CGCTGTGGG       420

CATTTTACTT TAGGTTGCGT ATTGGAAGAT CAAGAGCATC AAGTCGCTAA AGAAGAAAG     480

GAAACACCTA CTACTGATAG TATGCCGCCA TTATTACGAC AAGCTATCGA ATTATTTGA     540

CACCAAGGTG CAGAGCCAGC CTTCTTATTC GGCCTTGAAT TGATCATATG CGGATTAGA    600

AAACAACTTA AATGTGAAAG TGGGTCCGAC ATGGAAAAAG CGACACCGGA GACGATGGT    660

CATTGGATTT GTCTGAAGAT GGAGCCAGCT CTGTGGATGG CCATTACAGC AACATCGCA    720

GGCGCAAGGC ACAGGACATT CGTCGGGTTT TCCGGCTGCC TCCACCGCAA ATCCCTCAC    780

TACCCAGTGA TATGCCTGAG CAAACCGAGC CAGAGGATT                           819

(2) INFORMATION FOR SEQ ID NO: 36:

(i) SEQUENCE CHARACTERISTICS:
        (A) LENGTH: 652 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 36:

ATGTCTATGT CTAGATTAGA TAAAAGTAAA GTGATTAACA GCGCATTAGA GCTGCTTAAT     60

GAGGTCGGAA TCGAAGGTTT AACAACCCGT AAACTCGCCC AGAAGCTAGG TGTAGAGCA     120

CCTACATTGT ATTGGCATGT AAAAAATAAG CGGGCTTTGC TCGACGCCTT AGCCATTGA    180

ATGTTAGATA GGCACCATAC TCACTTTTGC CCTTTAGAAG GGGAAAGCTG GCAAGATTT     240

TTACGTAATA AGGCTAAAAG TTTTAGATGT GCTTTACTAA GTCATCGCGA TGGAGCAAA    300

GTACATTTAG GTACACGGCC TACAGAAAAA CAGTATGAAA CTCTCGAAAA TCAATTAGC    360

TTTTTATGCC AACAAGGTTT TCACTAGAG AATGCATTAT ATGCACTCAG CGCTGTGGG    420

CATTTTACTT TAGGTTGCGT ATTGGAAGAT CAAGAGCATC AAGTCGCTAA AGAAGAAAG   480

GAAACACCTA CTACTGATAG TATGCCGCCA TTATTACGAC AAGCTATCGA ATTATTTGA   540

CACCAAGGTG CAGAGCCAGC CTTCTTATTC GGCCTTGAAT TGATCATATG CGGATTAGA  600

AAACAACTTA AATGTGAAAG TGGGTCCTCC CCGGGTAACT AAGTAAGGAT CC           652

(2) INFORMATION FOR SEQ ID NO: 37:

(i) SEQUENCE CHARACTERISTICS:
        (A) LENGTH: 1443 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 37:

ATGTCTATGT CTAGATTAGA TAAAAGTAAA GTGATTAACA GCGCATTAGA GCTGCTTAAT     60

GAGGTCGGAA TCGAAGGTTT AACAACCCGT AAACTCGCCC AGAAGCTAGG TGTAGAGCA    120

CCTACATTGT ATTGGCATGT AAAAAATAAG CGGGCTTTGC TCGACGCCTT AGCCATTGA   180

ATGTTAGATA GGCACCATAC TCACTTTTGC CCTTTAGAAG GGGAAAGCTG GCAAGATTT    240

TTACGTAATA AGGCTAAAAG TTTTAGATGT GCTTTACTAA GTCATCGCGA TGGAGCAAA   300
```

-continued

| | | | | | |
|---|---|---|---|---|---|
| GTACATTTAG | GTACACGGCC | TACAGAAAAA | CAGTATGAAA | CTCTCGAAAA | TCAATTAGC | 360 |
| TTTTTATGCC | AACAAGGTTT | TTCACTAGAG | AATGCATTAT | ATGCACTCAG | CGCTGTGGG | 420 |
| CATTTTACTT | TAGGTTGCGT | ATTGGAAGAT | CAAGAGCATC | AAGTCGCTAA | AGAAGAAAG | 480 |
| GAAACACCTA | CTACTGATAG | TATGCCGCCA | TTATTACGAC | AAGCTATCGA | ATTATTTGA | 540 |
| CACCAAGGTG | CAGAGCCAGC | CTTCTTATTC | GGCCTTGAAT | TGATCATATG | CGGATTAGA | 600 |
| AAACAACTTA | AATGTGAAAG | TGGGTCCCTG | GACGACTCGA | AGCGCGTAGC | CAAGCGGAA | 660 |
| CTGATCGAGG | AGAACCGGGA | GCGGCGACGC | AAGGAGGAGA | TGATCAAATC | CCTGCAGCA | 720 |
| CGGCCCAGCC | CCAGCGCAGA | GGAGTGGGAG | CTGATCCACG | TGGTGACCGA | GGCGCACCG | 780 |
| AGCACCAACG | CGCAGGGCAG | CCACTGGAAG | CAGAGGAGGA | AATTCCTGCT | CGAAGATAT | 840 |
| GGTCAGTCGC | CCATGGCCTC | CATGCTTGAC | GGGGACAAAG | TGGACCTGGA | GGCGTTCAG | 900 |
| GAGTTTACAA | AAATCATCAC | GCCGGCCATC | ACCCGCGTGG | TCGACTTTGC | CAAAAACCT | 960 |
| CCCATGTTCT | CGGAGCTGCC | GTGCGAGGAT | CAGATCATCC | TGCTGAAGGG | CTGCTGCA | 1020 |
| GAGATCATGT | CGCTGCGCGC | CGCCGTGCGC | TACGACCCCG | AGAGCGAAAC | GCTGACGC | 1080 |
| AGCGGGGAAA | TGGCCGTCAA | ACGCGAGCAG | TTGAAGAACG | GAGGGCTGGG | GGTCGTGT | 1140 |
| GATGCCATCT | TCGACCTCGG | CAAGTCGCTG | TCTGCCTTCA | ACCTGGACGA | CACCGAGG | 1200 |
| GCCCTGCTGC | AGGCCGTGCT | GCTCATGTCC | TCAGACCGGA | CGGGGCTGAT | CTGCGTGG | 1260 |
| AAGATAGAGA | AGTGCCAGGA | GTCGTACCTG | CTGGCGTTCG | AGCACTACAT | CAACTACC | 1320 |
| AAACACAACA | TTCCCCACTT | CTGGTCCAAG | CTGCTGATGA | AGGTGGCGGA | CCTGCGCA | 1380 |
| ATCGGCGCCT | ACCACGCCAG | CCGCTTCCTG | CACATGAAGG | TGGAGTGCCC | CACCGAGC | 1440 |
| TCC | | | | | | 1443 |

What is claimed is:

1. A fusion protein which activates transcription comprising a first polypeptide which binds to a test operator sequence in the presence of tetracycline or a tetracycline analogue operatively linked to a second polypeptide which activates transcription in eukaryotic cells.

2. The protein of claim 1, wherein the first polypeptide is a mutated Tet repressor.

3. The protein of claim 2, wherein the mutated Tet repressor has at least one amino acid substitution compared to a wild-type Tet repressor.

4. The protein of claim 2, wherein the mutated Tet repressor has at least one amino acid addition or deletion compared to a wild-type Tet repressor.

5. The protein of claim 2, wherein the mutated Tet repressor is a mutated Tn10-derived Tet repressor having an amino acid substitution at at least one amino acid position selected from the group consisting of position 71, position 95, position 101, and position 102.

6. The protein of claim 5, wherein the mutated Tn10-derived Tet repressor comprises an amino acid sequence shown in positions 1 to 207 of SEQ ID NO: 2.

7. The protein of claim 2, wherein the second polypeptide comprises a transcription activation domain of herpes simplex virion protein 16.

8. The protein of claim 7, wherein the transcription activation domain comprises a C-terminal amino acid region of herpes simplex virus virion protein 16 comprising an amino acid sequence shown in positions 208 to 335 of SEQ ID NO: 2.

9. The protein of claim 7, wherein the transcription activation domain comprises at least one copy of a C-terminal region of herpes simplex virus virion protein 16 comprising an amino acid sequence shown in SEQ ID NO: 4.

10. The protein of claim 2, wherein the second polypeptide comprises a transcription activation domain selected from the group consisting of: an acidic transcription activation domain, a proline-rich transcription activation domain, a serine/threonine-rich transcription activation domain, and a glutamine-rich transcription activation domain.

11. The protein of claim 2, wherein the fusion protein further comprises an operatively linked third polypeptide which promotes transport of the fusion protein to a cell nucleus.

* * * * *